US011517645B2

(12) United States Patent
Ker et al.

(10) Patent No.: US 11,517,645 B2
(45) Date of Patent: *Dec. 6, 2022

(54) BONE-TENDON GRAFT BIOMATERIAL, USE AS A MEDICAL DEVICE AND METHOD OF MAKING SAME

(71) Applicant: The Board of Trustees of the Leland Stanford Junior University, Stanford, CA (US)

(72) Inventors: Dai Fei Elmer Ker, Tai Po (HK); Yunzhi Yang, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 16/722,788

(22) Filed: Dec. 20, 2019

(65) Prior Publication Data
US 2020/0254141 A1   Aug. 13, 2020

Related U.S. Application Data

(62) Division of application No. 15/447,948, filed on Mar. 2, 2017, now Pat. No. 10,668,183.

(60) Provisional application No. 62/302,508, filed on Mar. 2, 2016.

(51) Int. Cl.
*A61L 27/18* (2006.01)
*A61L 27/54* (2006.01)
*C08G 18/73* (2006.01)
*C08G 18/32* (2006.01)
*C08G 18/67* (2006.01)
*C08L 75/16* (2006.01)
*C09J 175/14* (2006.01)

(52) U.S. Cl.
CPC ............... *A61L 27/18* (2013.01); *A61L 27/54* (2013.01); *C08G 18/3284* (2013.01); *C08G 18/6755* (2013.01); *C08G 18/73* (2013.01); *C08L 75/16* (2013.01); *C09J 175/14* (2013.01); *A61L 2300/414* (2013.01); *A61L 2430/02* (2013.01); *A61L 2430/10* (2013.01)

(58) Field of Classification Search
CPC combination set(s) only.
See application file for complete search history.

(56) References Cited

U.S. PATENT DOCUMENTS

| 4,373,057 | A | * | 2/1983 | Hammond | C08G 18/08 |
| | | | | | 524/700 |
| 5,178,952 | A | * | 1/1993 | Yamamoto | C08G 18/4216 |
| | | | | | 428/425.8 |
| 5,179,186 | A | * | 1/1993 | Muller | C08G 18/673 |
| | | | | | 528/49 |
| 5,910,536 | A | * | 6/1999 | Kydonieus | C08G 18/10 |
| | | | | | 524/590 |
| 2003/0149127 | A1 | * | 8/2003 | Jansen | C08G 18/285 |
| | | | | | 522/178 |
| 2010/0032090 | A1 | | 2/2010 | Myung et al. | |

OTHER PUBLICATIONS

Desmodur W data sheet, Feb. 12, 2014. (Year: 2014).*
Al-Jassir et al., "In vitro assessment of function graded (fg) artificial hip joint stem in terms of bone/cement stresses: 3d finite element (fe) study," Biomedical engineering online 12, 5, 17 pages (2013).
Alexander, "Elastic Energy Stores in Running Vertebrates," American Zoologist 24, pp. 85-94 (1984).
Andarawis-Puri et al., "Tendon basic science: Development, repair, regeneration, and healing," Journal of orthopaedic research 33, pp. 780-784 (2015).
Anderson et al., "Foreign body reaction to biomaterials," Seminars in Immunology 20, pp. 86-100 (2008).
Androjna et al., "Mechanical conditioning of cell-seeded small intestine submucosa: A potential tissue-engineering strategy for tendon repair," Tissue engineering 13, pp. 233-243 (2007).
Aristizabal et al., Adverse Events Associated with Biodegradable Lactide-Containing Suture Anchors. Arthroscopy 30, pp. 555-560 (2014).
Asonova et al., "use of masson's trichrome method for staining decalcified bone tissue," Arkhiv patologii 58, 66-67, (1996).
Barber, "Biodegradable Shoulder Anchors Have Unique Modes of Failure," Arthroscopy 23, pp. 316-320, (2007).
Bartlett et al., "A 3D-printed, functionally graded soft robot powered by combustion," Science 349, pp. 161-165 (2015).
Beason et al. "Fiber-aligned polymer scaffolds for rotator cuff repair in a rat model," Journal of shoulder and elbow surgery 21, pp. 245-250 (2012).
Belcher et al., "Adverse effect of porcine collagen interposition after trapeziectomy: A compartive study," Journal of hand surgery: British and European vol. 26, 159-164, (2001).
Benjamin et al., "Where tendons and ligaments meet bone: Attachment sites ('entheses') in relation to exercise and/or mechanical load," Journal of anatomy 208, pp. 471-490 (2006).
Benjamin et al., "Fibrocartilage in tendons and ligaments—an adaptation to compressive load," Journal of Anatomy, 193, pp. 481-494 (1998).
Blau et al., "Plasticity of the Differentiated State," Science 230, pp. 758-766 (1985).
Blumer et al., "Role of tartrate-resistant acid phosphatase (TRAP) in long bone development," Mechanisms of development 129, pp. 162-176 (2012).

(Continued)

*Primary Examiner* — Christopher M Rodd
(74) *Attorney, Agent, or Firm* — Venable LLP; Keith G. Haddaway

(57) ABSTRACT

The invention relates to a polyurethane bone-tendon graft biomaterial and method of making the bone-tendon graft biomaterial. The biomaterial has a gradient of mechanical properties through photocrosslinking such that a first end of the biomaterial is crosslinked at a higher degree than a second end, and the first end of the biomaterial has mechanical properties of bone and the second end of the biomaterial has mechanical properties of tendon.

16 Claims, 52 Drawing Sheets
(52 of 52 Drawing Sheet(s) Filed in Color)

(56) References Cited

OTHER PUBLICATIONS

Bogy, "The plane solution for joined dissimilar elastic semistrips under tension," Journal of applied mechanics 42, 93-98, (1975).
Bostman, "Adverse tissue reactions to bioabsorbable fixation devices," Clinical orthopaedics and related research 371, 216-227, (2000).
Brent, "FGF acts directly on the somitic tendon progenitors through the ets transcription factors pea3 and erm to regulate scleraxis expression," Development 131, 3885-3896, (2004).
Bromage et al., "Circularly Polarized Light Standards for Investigations of Collagen Fiber Orientation in Bone," Anatomical record Part B 274B, pp. 157-168 (2003).
Bruin et al., "Autoclavable highly cross-linked polyurethane networks in ophthalmology," Biomaterials, vol. 14, pp. 1089-1097 (1993).
Cai et al., "Inkjet printing of laminin gradient to investigate endothelial cellular alignment," Colloids and surfaces B 72, 230-235, (2009).
Caliari et al., "Structural and Biochemical Modification of a Collagen Scaffold to Selectively Enhance MSC Tenogenic, Chondrogenic, and Osteogenic Differentiation," Advanced Healthcare Materials, 3, pp. 1-11 (2014).
Caliari et al., "The effect of anisotropic collagen-gag scaffolds and growth factor supplementation on tendon cell recruitment, alignment, and metabolic activity," Biomaterials 32, 5330-5340, pp. 1-11 (2011).
Campbell et al., "Engineered spatial patterns of FGF-2 immobilized on fibrin direct cell organization," Biomaterials 26, pp. 6762-6770 (2005).
Chaudhury et al., "Tensile and shear mechanical properties of rotator cuff repair patches," Journal of shoulder and elbow surgery 21, pp. 1-9 (2011).
Chen et al., "Scleraxis-Overexpressed Human Embryonic Stem Cell-Derived Mesenchymal Stem Cells for Tendon Tissue Engineering with Knitted Silk-Collagen Scaffold," Tissue Engineering Part A 20, pp. 1583-1592 (2013).
Chen et al., "Tissue Engineering of Tendons: A Comparison of Muscle-Derived Cells, Tenocytes, and Dermal Fibroblasts as Cell Sources," Plastic and reconstructive surgery 137, pp. 536e-544e (2016).
Chin et al., "Characterization of and host response to tyramine substituted-hyaluronan enriched fascia extracellular matrix," Journal of materials science. 22, 23 pages, (2011).
Cooper et al., "Inkjet-Based Biopatterning of Bone Morphogenetic Protein-2 to Spatially Control Calvarial Bone Formation," Tissue Engineering. Part A 16, 1749-1759, (2010).
Cserjesi et al., "Scleraxis: A basic helix-loop-helix protein that prefigures skeletal formation during mouse embryogenesis," Development 121, pp. 1099-1110 (1995).
Deakin et al., "Suture strength and angle of load application in a suture anchor eyelet," Arthroscopy 21, 1447-1451, (2005).
Derwin et al., "Commercial extracellular matrix scaffolds for rotator cuff tendon repair," Biomechanical, biochemical, and cellular properties. Journal of bone and joint surgery 88, pp. 2665-2672 (2006).
Edom-Vovard et al., "Fgf4 positively regulates scleraxis and tenascin expression in chick limb tendons," Developmental biology 247, 351-366, (2002).
Engler et al., "Matrix elasticity directs stem cell lineage specification," Cell 126, 677-689, (2006).
Fukubayash et al., "Follow-up study of gore-tex artificial ligament-special emphasis on tunnel osteolysis," Journal of long-term effects of medical implants 10, 267-277, (2000).
Galatz et al., "Tendon Regeneration and Scar Rormation: The Concept of Scarless Healing," Journal of Orthopaedic Research, 33 pages (2015).
Gartsman, Shoulder arthroscopy. 2nd Ed. (W.B. Saunders, 2009).
Genin et al., "Functional Grading of Mineral and Collagen in the Attachment of Tendon to Bone," Biophysical journal 97, pp. 976-985 (2009).
Glueck et al., "Extensive Osteolysis After Rotator Cuff Repair With a Bioabsorbable Suture Anchor: A Case Report," American Journal of Sports Medicine 33, pp. 742-744 (2005).
Gulotta et al., "Bone marrow-derived mesenchymal stem cells transduced with scleraxis improve rotator cuff healing in a rat model," American Journal of Sports Medicine 39, 1282-1289, (2011).
Guo et al., "Mechanical strain promotes osteoblast ecm formation and improves its osteoinductive potential," Biomedical Engineering Online 11, 80, (2012).
Hersche et al., "Passive tension in the supraspinatus musculotendinous unit after long-standing rupture of its tendon: A preliminary report," Journal of Shoulder and Elbow Surgery 7, 393-396, (1998).
Hoffmann et al. "Neotendon formation induced by manipulation of the smad8 signalling pathway in mesenchymal stem cells." Journal of Clinical Investigation 116, 940-952, (2006).
Huard et al., "Human myoblast transplantation: Preliminary results of 4 cases," Muscle and Nerve 15, 550-560, (1992).
Inui et al., "Application of layered poly (l-lactic acid) cell free scaffold in a rabbit rotator cuff defect model," Sports Medicine, Arthroscopy, Rehabilitation, Therapy and Technology 3, 29, (2011).
Inui et al., "Regeneration of rotator cuff tear using electrospun poly(d,l-lactide-co-glycolide) scaffolds in a rabbit model," Arthroscopy 28, 1790-1799, (2012).
Itoi et al., "Tensile properties of the supraspinatus tendon," Journal of Orthopaedic Research 13, pp. 578-584 (1995).
Kabuto et al, "Stimulation of rotator cuff repair by sustained release of bone morphogenetic protein 7 using a gelatin hydrogel sheet-,"Tissue Engineering Part A 21, pp. 1-31 (2015).
Ker et al., "Bioprinting of growth factors onto aligned sub-micron fibrous scaffolds for simultaneous control of cell differentiation and alignment," Biomaterials 32, pp. 8097-8107 (2011).
Ker et al., "Engineering spatial control of multiple differentiation fates within a stem cell population," Biomaterials 32, pp. 3413-3422 (2011).
Ker, "Dynamic Tensile Properties of the Plantaris Rendon of Sheep (*Ovis aries*)," Journal of Experimental Biology 93, pp. 283-302 (1981).
Kim et al., "Arthroscopic repair of massive contracted rotator cuff tears: Aggressive release with anterior and posterior interval slides do not improve cuff healing and integrity," Journal of Bone and Joint Surgery 95, pp. 1482-1488 (2013).
Kim et al., "In vitro evaluation of photo-crosslinkable chitosan-lactide hydrogels for bone tissue engineering," Journal of Biomedical Materials Research Part B 102, 1393-1406, (2014).
Kim et al., "The Effect of Platelet Rich Plasma from Bone Marrow Aspirate with Added Bone Morphogenetic Protein-2 on the Achilles Tendon-Bone Junction in Rabbits," Clinics in Orthopedic Surgery 3, pp. 325-331 (2011).
Kovacevic et al., "Calcium-phosphate matrix with or without tgf-beta3 improves tendon-bone healing after rotator cuff repair," American Journal of Sports Medicine 39, 811-819, (2011).
Lamplot et al., "Distinct effects of platelet-rich plasma and bmp13 on rotator cuff tendon injury healing in a rat model," American Journal of Sports Medicine 42, pp. 2877-2887 (2014).
Lee et al., "BMP-12 treatment of adult mesenchymal stem cells in vitro augments tendon-like tissue formation and defect repair in vivo," PLoS One 6, e17531, (2011).
Lee et al., "Tendon-bone interface healing using an injectable rhbmp-2-containing collagen gel in a rabbit extra-articular bone tunnel model," Journal of Tissue Engineering and Regenerative Medicine, In Press, (2015).
Li et al., "Nanofiber Scaffolds with Gradations in Mineral Content for Mimicking the Tendon-to-Bone Insertion Site," Nano Letters, vol. 9, No. 7, pp. 2763-2768 (2009).
Lichtwark et al., "Is Achilles tendon compliance optimised for maximum muscle efficiency during locomotion?" Journal of Biomechanics 40, 1768-1775, (2007).
Lichtwark et al., "Optimal muscle fascicle length and tendon stiffness for maximising gastrocnemius efficiency during human walking and running," Journal of Theoretical Biology 252, pp. 662-673 (2008).
Lipner et al., "In vivo evaluation of adipose derived stromal cells delivered with a nanofiber scaffold for tendon-to-bone repair," Tissue Engineering Part A 21, pp. 1-30 (2015).

(56) References Cited

OTHER PUBLICATIONS

Liu et al., "Generation of Electrospun Nanofibers with Controllable Degrees ofCrimping Through a Simple, Plasticizer-Based Treatment," Advanced Materials, pp. 1-6 (2015).
Liu et al., "Mechanisms of Bimaterial Attachment at the Interface of Tendon to Bone," Journal of Engineering Materials and Technology 133, 22 pages (2011).
Longo et al., "Histopathology of rotator cuff tears," Sports Medicine and Arthroscopy 19, 227-236, (2011).
Longo et al., "Histopathology of the supraspinatus tendon in rotator cuff tears," American Journal of Sports Medicine 36, 533-538, (2008).
Lu et al., "Functional attachment of soft tissues to bone: Development, healing, and tissue engineering," Annual Review of Biomedical Engineering 15, 201-226, (2013).
Lu et al., "Tissue engineering strategies for the regeneration of orthopedic interfaces," Annals of Biomedical Engineering 38, 2142-2154, (2010).
Makris et al., "Developing functional musculoskeletal tissues through hypoxia and lysyl oxidase-induced collagen cross-linking," Proceedings of the National Academy of Sciences USA 111, pp. 1-10 (2014).
Malcarney et al., "Early inflammatory reaction after rotator cuff repair with a porcine small intestine submucosal implant: A report of 4 cases," American Journal of Sports Medicine 33, 907-911, (2005).
Manolagas et al., "1,25-dihydroxyvitamin d3 stimulates the alkaline phosphatase activity of osteoblast-like cells," Journal of Biological Chemistry 256, 7115-7117, (1981).
Manolagas et al., "Mechanism of action of 1,25-dihydroxyvitamin d3-induced stimulation of alkaline phosphatase in cultured osteoblast-like cells," Molecular and Cellular Endocrinology 33, 27-36, (1983).
Marieb, "Human anatomy and physiology," 5th Ed. (Benjamin Cummings, 1999).
Mather et al., "The Societal and Economic Value of Rotator Cuff Repair," Journal of Bone and Joint Surgery 95, 8 pages (2013).
Matsuhashi et al., "Tensile Properties of a Morphologically Split Supraspinatus Tendon," Clinical Anatomy 27, pp. 702-706 (2014).
McCarron et al., "Improved time-zero biomechanical properties using poly-l-lactic acid graft augmentation in a cadaveric rotator cuff repair model," Journal of Shoulder and Elbow Surgery 19, pp. 688-696 (2010).
Mehrali et al., "Dental implants from functionally graded materials," Journal of Biomedical Materials Research Part A 101, pp. 3046-3057 (2013).
Mercado-Pagan, et al. "Synthesis and characterization of novel elastomeric poly(d,l-lactide urethane) maleate composites for bone tissue engineering," European Polymer Journal 49, pp. 3337-3349 (2013).
Meyer et al., "Structure and contractile force of the supraspinatus muscle is correlated with the results of rotator cuff reconstruction," Journal of Bone and Joint Surgery, British vol. 90-B, 293, (2008).
Mihara et al., "Rotator cuff repair using an original iliotibial ligament with a bone block patch: Preliminary results with a 24-month follow-up period," Journal of Shoulder and Elbow Surgery, In Press, pp. 1-8 (2016).
Miller et al., "Dose-dependent cell growth in response to concentration modulated patterns of fgf-2 printed on fibrin," Biomaterials 27, 2213-2221, (2006).
Miller et al., "Inkjet Printing of Growth Factor Concentration Gradients and Combinatorial Arrays Immobilized on Biologically-Relevant Substrates," Combinatorial Chemistry and High Throughput Screening 12, pp. 604-618 (2009).
Miller et al., "Spatially Directed Guidance of Stem Cell Population Migration by Immobilized Patterns of Growth Factors," Biomaterials 32, pp. 1-24 (2011).
Moffat et al., "Characterization of the structure-function relationship at the ligament-to-bone interface," Proceedings of the National Academy of Sciences USA 105, pp. 7947-7952 (2008).
Moffat et al., "Orthopedic interface tissue engineering for the biological fixation of soft tissue grafts," Clinical Sports Medicine 28, pp. 157-176 (2009).
Morais et al., "Current Approaches and Future Trends to Promote Tendon Repair," Annals of Biomedical Engineering, 11 pages (2015).
Murphy, "The return of photoelastic stress measurements: Utilizing birefringence to monitor damage and repair in healable materials," Journal of Materials Chemistry 21, pp. 1438-1446 (2011).
Nagasawa et al., "Static and dynamic biomechanical properties of the regenerating rabbit achilles tendon," Clinical Biomechanics (Bristol, Avon) 23, pp. 832-838 (2008).
Oh et al., "Two cases of biodegradable suture anchor displacement diagnosed with ultrasonography following arthroscopic rotator cuff repair," Clinics in Shoulder and Elbow, In Press, 7 pages (2015).
Otabe et al., "Transcription factor mohawk controls tenogenic differentiation of bone marrow mesenchymal stem cells in vitro and in vivo," Journal of Orthopaedic Research 33, pp. 1-8 (2014).
Pelled et al., "Smad8/BMP2-Engineered Mesenchymal Stem Cells Induce Accelerated Recovery of the Biomechanical Properties of the Achilles Tendon," Journal of Orthopaedic Research 30, pp. 1932-1939 (2012).
Peterson et al., "Evaluation of a collagen-coated, resorbable fiber scaffold loaded with a peptide basic fibroblast growth factor mimetic in a sheep model of rotator cuff repair," Journal of Shoulder and Elbow Surgery, 24, pp. 1-10 (2015).
Phillippi et al., "Microenvironments engineered by inkjet bioprinting spatially direct adult stem cells toward muscle- and bone-like subpopulations," Stem Cells 26, 127-134, (2008).
Phillips et al., "Engineering graded tissue interfaces," Proceedings of the national academy of sciences USA 105, 12170-12175, (2008).
Phillips et al., "Retroviral-mediated gene therapy for the differentiation of primary cells into a mineralizing osteoblastic phenotype," Methods in Molecular Biology 433, 333-354, (2008).
Popov et al., "Mechanical stimulation of human tendon stem/progenitor cells results in upregulation of matrix proteins, integrins and mmps, and activation of p38 and erk1/2 kinases," Biomed Central Molecular Biology 16, 6, pp. 1-11 (2015).
Puchtler et al., "Demonstration of phosphates in calcium deposits: A modification of von kossa's reaction," Histochemistry 56, pp. 177-185 (1978).
Qin et al., "Impact tolerance in mussel thread networks by heterogeneous material distribution," Nature Communications 4, 2187, (2013).
Qu et al., "Engineering Complex Orthopaedic Tissues via Strategic Biomimicry," Annals of Biomedical Engineering 43, 21 pages (2014).
Ramalingam et al., "Nanofiber scaffold gradients for interfacial tissue engineering," Journal of Biomaterials Applications, 27(6), pp. 695-705 (2013).
Randelli et al., "State of the art in rotator cuff repair," Knee Surgery, Sports Traumatology, Arthroscopy 23, pp. 341-343 (2015).
Riley et al., "Tenascin-C and Human Tendon Degeneration," American Journal of Pathology 149, pp. 933-943 (1996).
Sano et al., "Degeneration at the insertion weakens the tensile strength of the supraspinatus tendon: A comparative mechanical and histologic study of the bone-tendon complex," Journal of Orthopaedic Research 15, 719-726, (1997).
Schneider et al., "Influence of ph on wound-healing: A new perspective for wound-therapy?" Archives of Dermatological Research 298, 413-420, (2007).
Schwartz et al., "Mineral distributions at the developing tendon enthesis," PLoS one 7, e48630, pp. 1-11 (2012).
Sclamberg et al., "Six-month magnetic resonance imaging follow-up of large and massive rotator cuff repairs reinforced with porcine small intestinal submucosa," Journal of shoulder and elbow surgery 13, 538-541, (2004).
Seeherman et al., "rhBMP-12 Accelerates Healing of Rotator Cuff Repairs in a Sheep Model," Journal of Bone and Joint Surgery 90, pp. 2206-2219 (2008).
Shen et al., "BMP12 induces tenogenic differentiation of adipose-derived stromal cells," PLoS One 8, e77613, pp. 1-14 (2013).

(56) References Cited

OTHER PUBLICATIONS

Shukunami et al., "Scleraxis positively regulates the expression of tenomodulin, a differentiation marker of tenocytes," Developmental Biology 298, pp. 234-247 (2006).
Silverstein et al., "Spectrometric identification of organic compounds," 7th Ed. (John Wiley & Sons, 2005).
Smith et al., "Comparison of a novel bone-tendon allograft with a human dermis-derived patch for repair of chronic large rotator cuff tears using a canine model," Arthroscopy 28, 169-177, (2012).
Smith et al., "Precise Control of Osteogenesis for Craniofacial Defect Repair: The Role of Direct Osteoprogenitor Contact in BMP-2-Based Bioprinting," Annals of Plastic Surgery, vol. 69, No. 4, pp. 485-488 (2012).
Soler et al., "Early complications from the use of porcine dermal collagen implants (permacol) as bridging constructs in the repair of massive rotator cuff tears," A report of 4 cases. Acta orthopaedica Belgica 73, p. 432-436 (2007).
Spalazzi et al., "In vivo Evaluation of a multiphased scaffold designed for orthopaedic interface tissue engineering and soft tissue-to-bone integration," Young Investigator's Award, 8th World Biomaterials Congress, Amsterdam RAI, The Netherlands, May 28-Jun. 1, 2008. (12 pages).
Spalazzi et al., "In Vivo Evaluation of a Tri-Phasic Composite Scaffold for Anterior Cruciate Llgament-to-Bone Integration," Proceedings of the 28th IEEE Embs Annual International Conveference, In Annual International Conference Proceedings of the IEEE Engineering in Medicine and Biology Society, pp. 525-528 (2006).
Spalazzi, J. P., Doty, S. B., Moffat, K. L., Levine, W. N. & Lu, H. H. Development of controlled matrix heterogeneity on a triphasic scaffold for orthopedic interface tissue engineering. Tissue engineering 12, 3497-3508, (2006).
Spencer, Jr. et al., "Interobserver agreement in the classification of rotator cuff tears using magnetic resonance imaging," American Journal of Sports Medicine 36, 99-103, (2008).
St. John, "The use of polyurethane materials in the surgery of the spine: A review," Spine Journal, vol. 14, pp. 3038-3047 (2014).
Szycher, Szycher's handbook of polyurethanes, 2nd Ed. (CRC Press, 2012).
Taipale et al., "Growth factors in the extracellular matrix," Federation of American Societies for Experimental Biology Journal 11, 51-59, (1997).
Tan et al., "Mechanical properties of functionally graded hierarchical bamboo structures," Acta Biomaterialia 7, pp. 3796-3803 (2011).
Tang et al., "Fetal and adult fibroblasts display intrinsic differences in tendon tissue engineering and regeneration," Scientific Reports 4, 5515, (2014).
Tang et al., "Regulatory effects of introduction of an exogenous fgf2 gene on other growth factor genes in a healing tendon," Wound Repair and Regeneration 22, 111-118, (2014).
Theiss et al., "Use of biomimetic microtissue spheroids and specific growth factor supplementation to improve tenocyte differentiation and adaptation to a collagen-based scaffold in vitro," Biomaterials 69, 99-109, (2015).
Tokunaga et al., "FGF-2 Stimulates the Growth of Tenogenic Progenitor Cells to Facilitate the Generation of Tenomodulin-Positive Tenocytes in a Rat Rotator Cuff Healing Model," American Journal of Sports Medicine 43, pp. 1-12 (2015).
Tokunaga et al., "Local Application of Gelatin Hydrogel Sheets Impregnated With Platelet-Derived Growth Factor BB Promotes Tendon-To-Bone Healing After Rotator Cuff Repair in Rats," Arthroscopy: The Journal of Anthroscopic and Related Surgery, pp. 1-10 (2015).
Uquillas et al., "Genipin crosslinking elevates the strength of electrochemically aligned collagen to the level of tendons," Journal of the Mechanical Behavior of Biomedical Materials 15C, 176-189, (2012).
Van der Biest et al., Advanced biomaterials 323-356 (John Wiley & Sons, Inc., 2010).
Wall et al., "Age-Related Changes in the Density and Tensile Strength of Human Femoral Cortical Bone," Calcified Tissue International 27, pp. 105-108 (1979).
Walton et al., "Restore Orthobiologic Implant: Not Recommended for Augmentation of Rotator Cuff Repairs," Journal of Bone and Joint Surgery 89, pp. 786-791 (2007).
Wang et al., "Induction of transient tenogenic phenotype of high density cultured human dermal fibroblasts," Connective Tissue Research 56, 288-299, (2015).
Wang et al., "Self-initiated photopolymerization and photografting of acrylic monomers," Macromolecular Rapid Communications 25, pp. 1095-1099 (2004).
Wen et al., "Interplay of matrix stiffness and protein tethering in stem cell differentiation," Nature Materials 13, pp. 1-9 (2014).
Wildemann et al., "Quantification of growth factors in allogenic bone grafts extracted with three different methods," Cell and Tissue Banking 8, pp. 107-114 (2007).
Wolfman et al., "Ectopic induction of tendon and ligament in rats by growth and differentiation factors 5, 6, and 7, members of the tgf-beta gene family," Journal of Clinical Investigation 100, 321-330, (1997).
Wright et al., "Myogenin, a Factor Regulating Myogenesis, Has a Domain Homologous to MyoD," Cell 56, pp. 607-617 (1989).
Xie et al., "'Aligned-to-random' nanofiber scaffolds for mimicking the structure of the tendon-to-bone insertion site," Nanoscale 2, pp. 923-926 (2010).
Xie et al., "Fabrication of Nanofiber Scaffolds With Gradations in Fiber Organizaiton and Their Potential Applications," Macromolecular Bioscience 12, pp. 1336-1341 (2012).
Xu et al., "Dissimilar Material Joints With and Without Free-edge Stress Singularities: Part I. A Biologically Inspired Design," Society for Experimental Mechanics, vol. 44, No. 6, pp. 608-615 (2004).
Xu et al., "Dissimilar Material Joints With and Without Free-edge Stress Singularities: Part II. A an Integrated Numerical Analysis," Society for Experimental Mechanics, vol. 44, No. 6, pp. 616-621 (2004).
Yang et al., "Engineering Orthopedic Tissue Interfaces," Tissue Engineering Part B 15, 127-141, (2009).
Yang et al., "Mechanical memory and dosing influence stem cell fate," Nature Materials 13, pp. 645-652 (2014).
Younesi et al., "Tenogenic induction of human mscs by anisotropically aligned collagen biotextiles," Advanced Functional Materials 24, 5762-5770, (2014).
Yuehuei et al., in Mechanical testing of bone and the bone-implant interface (CRC Press, 1999).
Zhang et al., "Bfgf- and capp-loaded fibrin clots enhance the bioactivity of the tendon-bone interface to augment healing," American Journal of Sports Medicine, In Press, (2016).
Zhang et al., "Well-aligned chitosan-based ultrafine fibers committed teno-lineage differentiation of human induced pluripotent stem cells for achilles tendon regeneration," Biomaterials 53, 716-730, (2015).
Zhao et al., "Effect of the Interposition of Calcium Phosphate Materials on Tendon-Bone Healing During Repair of Chronic Rotator Cuff Tear," American Journal of Sports Medicine, 42, pp. 1-10 (2014).
Zhao et al., "Spontaneous and specific myogenic differentiation of human mesenchymal stem cells on polyethylene glycol-linked multi-walled carbon nanotube films for skeletal muscle engineering," Nanoscale 7, pp. 18239-18249 (2015).

* cited by examiner

BONE-TENDON GRAFT BIOMATERIAL, USE AS A MEDICAL DEVICE AND METHOD OF MAKING SAME

CROSS-REFERENCE OF RELATED APPLICATION

This application is a divisional of U.S. application Ser. No. 15/447,948, filed Mar. 2, 2017, which claims priority to U.S. Provisional Application No. 62/302,508 filed Mar. 2, 2016; the entire contents of each of which are hereby incorporated by reference.

This invention was made with Government support under contract W81XWH-10-1-0966 awarded by the Department of Defense and under contracts AR057837 and DE021468 awarded by the National Institutes of Health. The Government has certain rights in the invention.

BACKGROUND

1. Technical Field

The field of the currently claimed embodiments of this invention relates to a UV-crosslinkable, polyurethane biomedical device. Specifically, the embodiments of this invention relates to a bone-tendon graft biomaterial.

2. Discussion of Related Art

The native bone-tendon interface is highly anisotropic, consisting of a compositionally- and mechanically-graded structure with bone- and tendon-like properties maintained by multiple musculoskeletal cell types. Specialized extracellular matrices secreted by musculoskeletal cells including osteoblasts and tenocytes enable this functionally-graded structure to fulfill its biomechanically-demanding role of simultaneously attaching compliant tendon to stiff bone while reducing stress concentrations during musculoskeletal movement[1,2]. Upon injury, however, the bone-tendon interface often heals incompletely, resulting in disorganized and biomechanically-inferior scar tissue[3,4] prone to re-tear. In rotator cuff injuries, high re-tear rates ranging from 21% to 91%[5,6] persist after surgical intervention, and in severe cases where massive tears are present, the damage is deemed irreparable[7]. Although natural and synthetic grafts are commercially-available, they reportedly have poor clinical outcomes[5,8]. While reasons for their lack of efficacy vary, materials that better mimic features of bone-tendon tissues, including native biomechanical properties and re-establishment of resident cells are expected to be vital for successful reattachment and regeneration of stiff bone to compliant tendon after injury[1,2,9].

Critical considerations in engineering biomaterials for bone-tendon repair include mimicking native tissue mechanical properties, spatially-regulating cell differentiation and possessing physicochemical characteristics favorable for graft-host integration. Accordingly, research efforts have focused on developing materials with bone- and tendon-like mechanical properties to sustain physiological loading as well as administering biological cues to direct multi-tissue healing. Efforts to sustain physiological loading include using non-graded materials[10-14] to engineer tendon substitutes or graded, bone-tendon substitutes that reduce stress concentrations via mechanical-gradation[15-17]. Such materials aim to facilitate musculoskeletal movement at pre-injury levels while minimizing material failure. Efforts to improve multi-tissue healing with biologics include delivering bone- and tendon-promoting growth factors as well as extracellular matrices[15,18-22], unmodified[21] or genetically-engineered stem cells[23-27] and platelet-rich plasma[20]. Such biological cues aim to re-establish native bone and tendon cells for regenerating and maintaining tissue phenotypes. In addition to these efforts, it is vital for materials to possess physicochemical characteristics favorable for clinical translation including physical features for musculoskeletal attachment and slow degradation[28]. Such physicochemical features aim to establish graft-host tissue continuity while maintaining adequate graft integrity to support both physiological loading and tissue healing. However, at this time, there are no materials that simultaneously attain bone- and tendon-like mechanical properties, spatially control musculoskeletal cell differentiation and possess characteristics favorable for eventual graft-host integration[1,2,9].

To engineer a bioactive material with spatially-controlled bone- and tendon-like properties, we developed a mechanically-graded, growth factor-biopatterned polymer. To achieve the mechanically-demanding properties of bone- and tendon-like tissues while allowing for gradation and slow degradation, a combination of chemical-crosslinking, photo-crosslinking and heat-curing were utilized to fabricate a highly-crosslinked, phototunable polyurethane network with slow hydrolysable bonds. To direct musculoskeletal differentiation, we utilized an inkjet-based bioprinter that previously spatially patterned and immobilized growth factors at physiologically-relevant concentrations to direct cell differentiation in vitro[18,19,29,30] and in vivo[31,32] in spatial registration to printed patterns. Here, quadrol (Q), hexamethylene diisocyanate (H) and methacrylic anhydride (M) were used to develop solvent-, catalyst- and photoinitiator-free, UV-crosslinkable polyurethane (QHM polymers) that: 1) possessed phototunable bone- and tendon-like mechanical properties as well as reduced stress concentrations via stiffness gradation; 2) achieved spatial control of osteoblast and tenocyte differentiation via substrate stiffness and growth factor-biopatterning; and, 3) exhibited slow degradation profiles with minimal cytotoxicity and could be fashioned as a hybrid suture anchor-tendon graft.

An inkjet-based bioprinter was used to spatially biopattern and immobilize growth factors at physiologically-relevant concentrations to direct cell differentiation in vitro [23, 24, 33, 34] and in vivo [35, 36] in spatial registration to printed patterns. The present invention relates to UV-crosslinkable, polyurethane polymers biomedical device. The biomedical device of the present invention possessed 1) phototunable mechanical properties that approximated bone and tendon as well as reduced stress concentrations via mechanical gradation, 2) achieved spatial control of osteoblast and tenocyte differentiation via substrate stiffness and growth factor-biopatterning, and 3) is fashioned as a slowly-degrading, synthetic hybrid suture anchor-graft. The present invention may be use in studying musculoskeletal biology and treating bone-tendon injuries.

SUMMARY

An embodiment of the present invention relates to a mechanically-graded and growth factor-biopatterned polyurethane having bone- and tendon-like mechanical properties, spatial control of musculoskeletal differentiation and physicochemical characteristics favorable for bone-tendon repair.

The inventive biomedical device is made with an inventive polyurethane material according to an embodiment of the present invention. In an embodiment, the biomedical device has mechanically-graded bone- and tendon-like properties and may be fashioned to connect to bone and tendon for treating bone-tendon injuries. In an embodiment, the biomedical device may be a hybrid of devices, such as a suture anchor and a tendon-like graft, used for repairing bone-tendon injuries where bone and tendon are connected. In yet another embodiment, the biomedical device may have a tensile strength in a range of from about 20 to about 74 MPa, a tensile modulus in a range of from about 0.6 to about 2.7 GPa, a compressive strength in a range of from about 58 to about 121 MPa, and a compressive modulus in a range of from about 1.5 to about 3.1 GPa. These ranges may be achieved by varying the amount of UV- and heat-exposure to the material. The tendon-like biomaterial may be able to withstand physiological tensile loading force of 3 MPa for at least 10,000 cycles. In an embodiment, biomedical device has two ends, a suture anchor end and a tendon-like end. The suture anchor end and the tendon-like end may have different mechanical properties. For example, the suture anchor end may be more rigid or less flexible than the tendon-like end.

In an embodiment, the inventive polyurethane biomaterial may be a product of a polyol, a polyisocyanate, and an acrylate. Through controlled photocrosslinking, the polyurethane may have a gradient of mechanical properties. For example, one end of the polyurethane may have bone-like mechanical properties, the opposite end may have tendon-like mechanical properties, and the area in between the two opposing end may have a gradual variant of mechanical bone-/tendon-like properties. In an embodiment of the present invention, the polyol comprises N,N,N',N'-tetrakis(2-hydroxyethyl)ethylenediamine, the polyisocyanate comprises hexamethylene diisocyanate, and the photocrosslinkable acrylate comprises methacrylic anhydride.

The bone-tendon graft biomaterial of the present invention may be made by mixing a polyol, a polyisocyanate, and an acrylate to form a polyurethane pre-mixture. The polyurethane pre-mixture is transferred to a mold, degassed under vacuum or in an inert atmosphere, in the presence or absence of solvent, catalyst, and photoinitiator to form an intermediate material. At least when the reaction is among N,N,N',N'-tetrakis(2-hydroxyethyl)ethylenediamine, hexamethylene diisocyanate and methacrylic anhydride, there is no requirement for a solvent, catalyst or photoinitiator during the degassing. The intermediate material may be cured by exposure to UV light and further reactions may be allowed to proceed under pressure in an inert atmosphere. Then the intermediate material may be heat-cured to form the bone-tendon graft biomaterial. Although cells are able to bind to the virgin material, the bone-tendon graft biomaterial may subsequently be coated with an extracellular matrix such as fibrin to create a more physiologically-relevant environment conducive for cell growth as well as growth factor immobilization.

In another embodiment, the biomedical device may be used as musculoskeletal repair of bone-tendon or bone-ligament or bone-ligament-bone interfaces such as rotator cuff repair, Achilles tendon repair, or other part of the body. The biomedical device may degrade by slowly absorbing and integrating into the body. For example, the biomedical device may slowly be replaced by the body without drastic loss of mechanical properties.

An embodiment of the present invention relates to a polyurethane comprising a reaction product of a polyol, a polyisocyanate, and an acrylate.

Another embodiment of the present invention relates to a bone-tendon graft biomaterial comprising the inventive polyurethane, wherein the biomaterial has a gradient of mechanical properties through photocrosslinking such that a first end of the biomaterial is crosslinked at a higher degree than a second end, and the first end of the biomaterial has mechanical properties of bone and the second end of the biomaterial has mechanical properties of tendon.

Another embodiment of the present invention relates to a method of making a bone-tendon graft biomaterial, comprising mixing a polyol, a polyisocyanate, and an acrylate to form a polyurethane pre-mixture; degassing the polyurethane pre-mixture under vacuum; transferring the polyurethane pre-mixture to a mold; reacting the polyurethane pre-mixture under vacuum or in an inert atmosphere to form an intermediate material; UV-curing the intermediate material by exposure to UV light; placing the intermediate material under pressure in an inert atmosphere; and heat-curing the intermediate material to form the bone-tendon graft biomaterial.

Another embodiment of the present invention relates to a bone-tendon graft biomedical device comprising the inventive biocompatible polyurethane, wherein the biomedical device comprises a first end having mechanical properties of bone and an elongated second end, such that the first end is crosslinked at a higher degree than the elongated second end, and the first end of the biomaterial has mechanical properties of bone and the second end of the biomaterial has mechanical properties of tendon.

Another embodiment of the present invention relates to a bone-tendon graft biomedical device comprising the inventive biocompatible polyurethane material forming a structure having a first end that has mechanical properties adapted for attachment to bone and a second end that has mechanical properties adapted for attachment to at least one of tendon or muscle, the polyurethane comprises a reaction product of a polyol, a polyisocyanate, and an acrylate, and the polyurethane is crosslinked at a higher degree at the first end than at the second end.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objectives and advantages will become apparent from a consideration of the description, drawings, and examples.

FIG. 1A is a hypothetical reaction scheme showing synthesis of QHM polymer. FIG. 1B shows $^1$H-NMR spectra of individual QHM polymer components and QHM pre-polymer. $^1$H-NMR peaks indicated by letters were assigned to their respective protons in the chemical structures. FIG. 1C shows FTIR-ATR spectra of individual QHM polymer components and QHM pre-polymer. Regions of interest 1 and 2 are indicated by orange and magenta dashed boxes, respectively.

FIG. 2A shows FTIR-ATR spectra of quadrol and hexamethylene diisocyanate. FIG. 2B shows FTIR-ATR spectra of quadrol and methacrylic anhydride. FIG. 2C shows FTIR-ATR spectra of hexamethylene diisocyanate and methacrylic anhydride. FIG. 2D shows $^1$H-NMR spectra of UV-exposed QHM polymers.

FIG. 3A shows uniaxial tensile testing of QHM polymers (n=6; 3 independent experiments). Y indicates that sample yield value was reported whereas F indicates that sample failure value was reported. FIG. 3B shows uniaxial compressive testing of QHM polymers (n=6; 3 independent experiments). FIG. 3C shows static creep tensile testing (3 MPa) of 0 s UV QHM polymer (n=3). FIG. 3D shows cyclic tensile testing (10,000 cycles from 0.2 MPa to 3 MPa) of 0 s UV QHM polymer (n=3). Error bars indicate standard error of mean. Statistical significance (p≤0.05) as indicated.

FIG. 4A shows differential scanning calorimetry thermogram of QHM polymers. FIG. 4B shows glass-liquid transition temperature of QHM polymers.

FIG. 5A shows a graph of the effect of cyclic tensile loading (100,000 cycles) on 0 s UV QHM polymer. 0 s UV QHM polymer was loaded between 0.2 MPa and 3 MPa for 100,000 cycles at 1 Hz (n=1). FIG. 5B shows photographs of before cyclic loading (6.593) and after cyclic loading and recovery (6.691). The readings show that the polymer does not tear even when subjected to many cycles of loading and unloading.

FIG. 6A shows finite element analysis of uniform or mechanically-graded quarter models with gradually- and steeply-graded interfaces subjected to 10 MPa tensile stress. A Poisson's ratio of 0.3 was used for top and bottom halves of each model. Peak values of concentrated stress not presented in color plot. FIG. 6B shows representative images of photoelastic tensile analysis for mechanically-graded specimens with gradually- and steeply-graded interfaces from 3 independent experiments. Dashed boxes indicate photoelastic specimens.

FIG. 9A shows the experimental set up and statistical legends for the effect of blebbistain on ALP activity. FIG. 9B shows the effect of UV-exposed QHM polymers on C2C12 osteoblast differentiation after 4 days culture in the presence or absence of 25 μm blebbistatin (n=3; 1 independent experiment). FIG. 9C shows the effect of UV-exposed QHM polymers on C2C12 osteoblast differentiation after 8 days culture in the presence or absence of 25 μm blebbistatin (n=3; 1 independent experiment). FIG. 9D shows effect of UV-exposed QHM polymers on C2C12 osteoblast differentiation after 14 days culture in the presence or absence of 25 μm blebbistatin (n=3; 1 independent experiment). ALP-positive regions stained blue. Scale bars 8 mm. Error bars indicate standard error of mean. Statistical significance (p≤0.05) as indicated.

FIG. 10A shows a graph of average porosity of QHM polymers (n=3). FIG. 10B shows a graph of average pore diameter of QHM polymers (n=3). Error bars indicate standard error of mean. Statistically significance (p≤0.05) as indicated.

FIG. 12A shows a graph of C3H10T1/2 cell attachment on QHM polymers, tissue culture-grade polystyrene (TCPS) and low cell attachment polystyrene (PS) 2 h post-seeding (n=12). FIG. 12B shows a graph of C3H10T1/2 cell viability on QHM polymers after 5 days culture (n=6). Scale bars 250 μm. Error bars indicate standard error of mean. * indicates statistical significance (p≤0.05) relative to TCPS.

FIG. 13A shows images of cell viability of C2C12 cells on QHM polymers after 5 days culture (n=6). FIG. 13B shows graph of cell proliferation of C2C12 cells on TCPS, QHM polymers and TCPS (Ethanol-treated 1 day-post seeding) after 5 days culture (n=6). Scale bars 400 μm. Error bars indicate standard error of mean.

FIG. 14A shows a schematic of mechanically-graded 0 s UV and 300 s UV QHM polymer (Left panel). Effect of mechanically-graded 0 s UV and 300 s UV QHM polymer on C2C12 osteoblast differentiation (Middle panel; n=1) and tenocyte differentiation of C2C12 cells after 3 days culture (Right panel; n=2). ALP-positive regions stained blue. SCX-positive regions are shown in white. Green arrowheads indicate interface. Scale bars 2 mm. FIG. 14B shows effect of uniform QHM polymers on osteoblast differentiation (n=6). RUNX2- and OCN-positive regions are shown in white. Scale bars 200 μm.

FIG. 15A shows effect of BMP-2 administration (6 days with BMP-2 versus 4 days with BMP-2) on osteoblast differentiation after 6 days culture (n=6). FIG. 15B Effect of BMP-2 dosage on osteoblast differentiation after 4 days culture (n=6). ALP-positive regions stained blue. Scale bars 8 mm. Error bars indicate standard error of mean. Statistical significance (p≤0.05) as indicated.

FIG. 19A shows experimental setup and statistical legend for in vitro studies. FIG. 19B. shows effect of BMP-2 biopatterning on spatial control of C2C12 osteoblast differentiation after 6 days culture (n=6; 1 independent experiment). ALP-positive regions stained blue. FIG. 19C. shows effect of FGF-2 biopatterning on spatial control of C2C12 tenocyte differentiation after 3 days culture (n=6; 1 independent experiment). SCX-positive regions are shown in white. FIG. 19D. shows experimental setup for in vivo studies. FIG. 19E. shows effect of BMP-2, FGF-2 and GDF-7 biopatterning on spatial control of bone- and tendon-like differentiation after 14 days subcutaneous implantation in mice (n=9 for no pattern, n=9 for FGF-2 patterns, n=9 for GDF-7 patterns and n=18 for BMP-2 patterns; 2 independent experiments). Nuclei stained blue/purple while cytoplasmic regions, extracellular structures and QHM polymers stained pink/red after H&E-staining. Nuclei and SCX-positive regions are shown in blue and red, respectively, after SCX-staining. TRAP-positive regions stained red after TRAP-staining. Collagen stained green after Trichrome-staining (Tri). Birefringent materials showed increased signal intensity in polarized microscopy images (Pol). Trichrome and polarized microscopy images shown were obtained from the same specimen. Scale bars as indicated. Error bars indicate standard error of mean. Statistical significance (p≤0.05) as indicated.

FIG. 22A BMP-2 immobilization on fibrin-coated QHM polymers (n=3). FIG. 22B FGF-2 immobilization on fibrin-coated QHM polymers (n=3). Representative fluorescence images and fluorescence quantification are shown. Error bars indicate standard error of mean.

FIG. 26A shows representative images of mechanically-graded QHM polymer. FIG. 26B shows representative images of mechanically-graded QHM polymer fabricated as a hybrid suture anchor-tendon graft. FIG. 26C is a scheme showing experimental setup for degradation studies. FIG. 26D shows degradation of QHM polymers under alkaline (5 N NaOH), acidic (2 N HCl), oxidizing (30% $H_2O_2$) and aqueous (HBSS) conditions at 37° C. over 8 weeks (n=6; 2 independent experiments). FIG. 26E shows swelling ratio of QHM polymers under alkaline (5 N NaOH), acidic (2 N HCl), oxidizing (30% $H_2O_2$) and aqueous (HBSS) conditions after 4 h at 37° C. (n=6; 2 independent experiments). FIG. 26F shows proliferation of C2C12 cells in 8-week HBSS degradation products (diluted 1:9 in media) of various QHM polymers during 5 days of culture (n=6; 2 independent experiments). FIG. 26G shows spontaneous differentiation of C2C12 cells into myotubes (red arrows) after 5 days of proliferation in 8-week HBSS degradation products (diluted 1:9 in media). Scale bars as indicated. Error bars indicate standard error of mean. FIG. 26H shows a graphical depiction of experimental methods of creating a mimic bone-tendon interface.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background, Detailed Description sections and Examples, are incorporated by reference into this disclosure as if each had been individually incorporated.

Rotator cuff tears are a common shoulder injury that have a large economic burden [41] which can be mitigated by bioengineered materials that provide adequate biomechanical function and promote bone-tendon healing. In the United States alone, over 200,000 surgeries are performed annually to treat rotator cuff injuries, costing an estimated $3.44 billion USD [41]. Engineering biomaterials that provide adequate biomechanical function and promote bone-tendon healing holds great promise to mitigate this burden. The present invention is a solvent-, catalyst- and photoinitiator-free UV-crosslinkable polyurethane (QHM polymers) with phototunable bone- and tendon-like tensile and compressive properties, including the capability to withstand 10,000 cycles of physiologic tensile loading and reduce stress concentrations via stiffness gradients. Spatial control of cell differentiation was demonstrated via substrate stiffness and growth factor-biopatterning whereby increased substrate stiffness enhanced and reduced growth factor-mediated osteoblast and tenocyte differentiation in vitro, respectively, while growth factor-biopatterning directed bone- and tendon-like differentiation in vitro and in vivo in spatial registration to printed patterns. Physicochemical studies showed slow degradation profiles and little-to-no cytotoxicity from degradation products in vitro. This work demonstrates a unique approach for engineering bioactive materials with spatially-controlled bone- and tendon-like properties and holds promise for addressing challenges in bone-tendon repair.

An embodiment of the present invention is a UV-crosslinkable, bioengineered material (FIGS. 1A-1C) that recapitulated major features of bone-tendon tissues, however, to reduce material complexity and facilitate clinical translation. The features of the bone-tendon issues include: 1) phototunable bone- and tendon-like mechanical properties (FIGS. 3A-3D, FIGS. 5A-5B and FIGS. 6A-6B); 2) spatial control of musculoskeletal differentiation (FIGS. 9A-9D, FIG. 14A, FIGS. 15A-15B, FIG. 17, FIG. 18, FIGS. 19A-19E, FIG. 23 and FIG. 24); and 3) physicochemical characteristic favorable for clinical translation (FIGS. 26A-26H).

Figure 27:
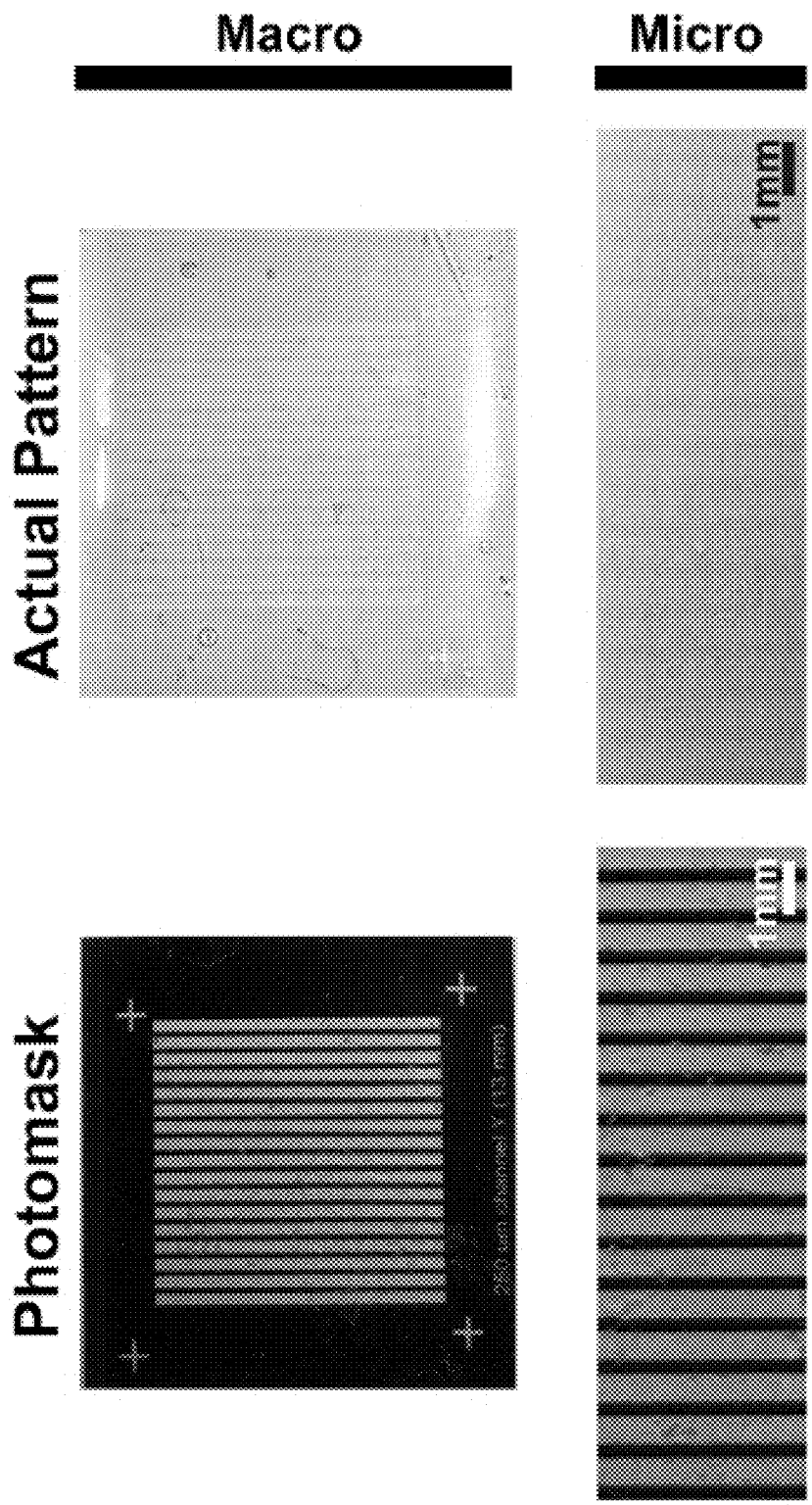
FIG. 27 shows effect of UV-Patterning on QHM Polymer. Macroscopic and microscopic images of QHM polymer (Right) patterned by 300 s UV-exposure using a photomask (Left). Scale bars 1 mm.
Figure 28:
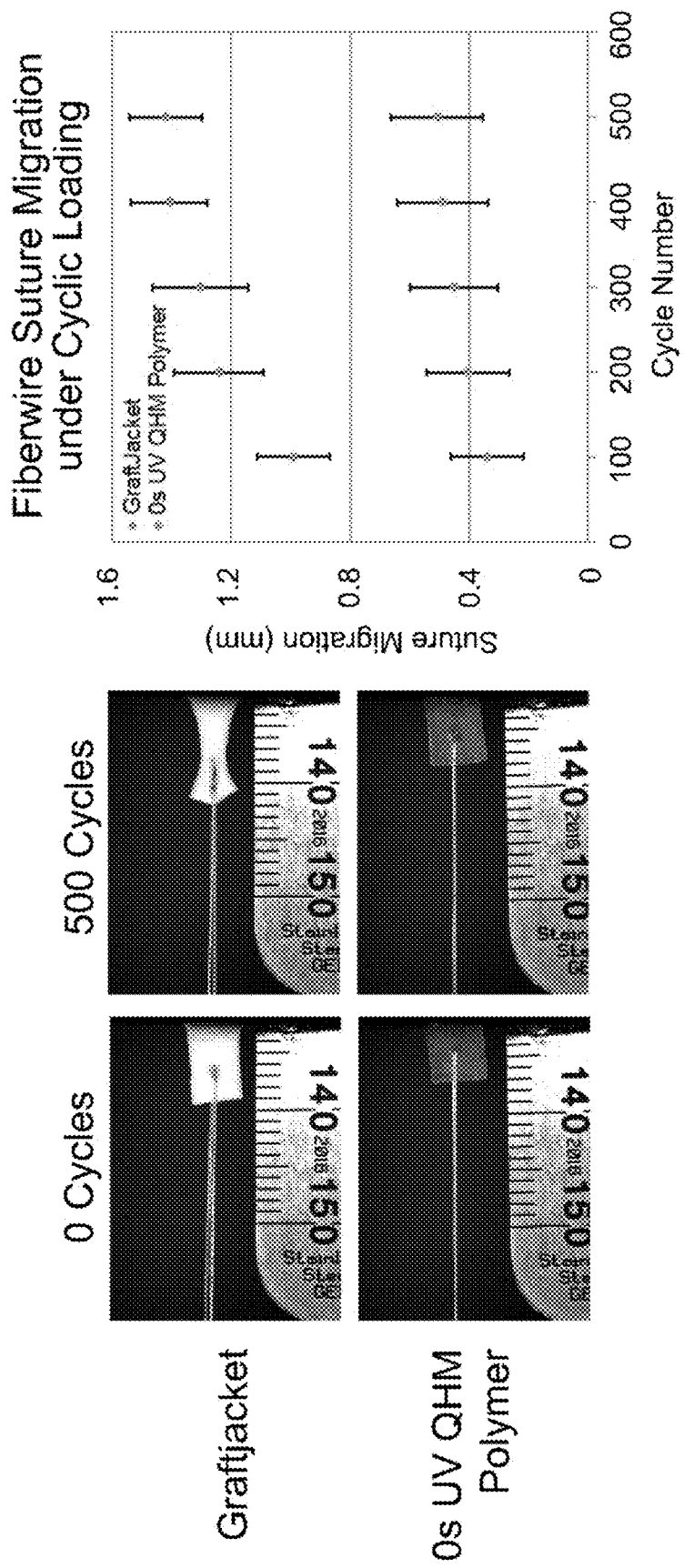
FIG. 28 shows GraftJacket and 0 s UV QHM polymer were loaded for 500 cycles and suture migration was measured. The data demonstrates that 0 s UV QHM polymer has better suture retention qualities than GraftJacket, an existing clinical material during 500 cycles of loading.
Figure 29:
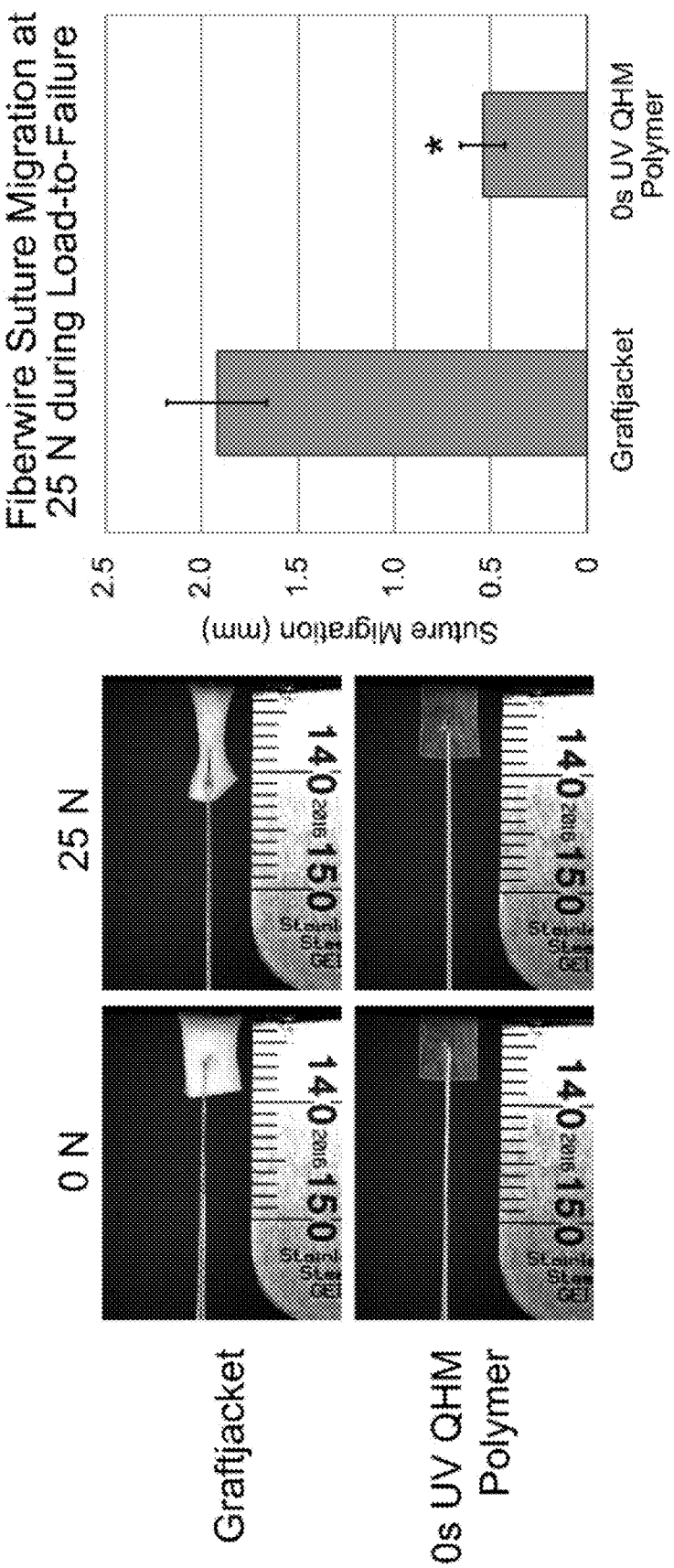
FIG. 29 shows GraftJacket and 0 s UV QHM polymer were loaded to failure and suture migration was measured. Results show suture migration at 25 N (Exceeds tensile strength of rat supraspinatus tendon). The data demonstrates that 0 s UV QHM polymer has better suture retention qualities than GraftJacket, an existing clinical material during load-to-failure.

Fabricating a biomaterial with native tissue-like mechanical properties is vital to restoring biomechanical function. Specifically, human supraspinatus tendon and cortical bone have reported tensile strengths of 4-22 MPa[39,40] and 66.0-170.0 MPa[41,42], respectively, as well as tensile moduli of 0.2-0.6 GPa[39,40] and 11.0-29.0 GPa[41,42], respectively. By combining chemical- and photo-crosslinking as well as heat-curing, QHM polymers were fabricated with tensile strength (12-74 MPa) and moduli (0.6-2.7 GPa) that approximated bone and tendon tissues (FIGS. 3A-3D, FIGS. 4A-4B, and FIGS. 5A-5B). This represents a marked improvement over commercially-available grafts and prior research efforts. Q is a tetrafunctional monomer with hydroxyl groups that react with the isocyanate and anhydride groups of H and M, respectively, producing a highly crosslinked polyurethane network with high mechanical properties. The phototunable capability arises from vinyl methine groups of M that participate in UV-crosslinking. No solvents, catalysts or photoinitators were required as monomer(s) were miscible, able to pseudo-catalyze polyurethane reactions[43] and self-initiate photopolymerization[44]. Also, 0 s UV QHM polymer withstood at least 10,000 cycles of physiologic cyclic loading[39,40,45,46], demonstrating robust, tensile properties that approximated the dynamic modulus and tan δ of tendon tissues (FIGS. 3A-3D and FIGS. 5A-5B). Approaches to reducing stress concentrations in native musculoskeletal tissues include varying mineral content and collagen fiber orientation along the bone-tendon interface[1,2,9]. These features presumably facilitate efficient load transfer between compliant tendon and stiff bone while minimizing tissue tearing[1,2,9]. Indeed, bone-tendon repairs that fail to restore native tissue mechanical properties show little-to-no regeneration of its graded fibrocartilaginous transition[1-4]. Since QHM polymers are phototunable and current photolithography techniques can achieve nanometer-scale resolutions, stiffness gradients can be fabricated at physiologically-relevant lengths (FIG. 27). FEA and photoelastic tensile testing of QHM polymers showed that gradual stiffness gradients reduced stress concentrations (FIGS. 6A-6B, FIG. 7, and FIG. 8). Reducing stress concentrations could minimize material failure to facilitate bone-tendon healing. Thus, QHM polymers possessed bone- and tendon-like mechanical properties with the capability to reduce stress concentrations via gradual gradation.

Re-establishing resident musculoskeletal cells at appropriate locations is vital for bone-tendon regeneration because musculoskeletal cells, including osteoblasts and tenocytes, secrete mineralized and unmineralized collagen matrices essential to maintaining bone-tendon tissues[1-4]. QHM polymers achieved spatial patterning of musculoskeletal differentiation by providing biomechanical and biochemical cues via substrate stiffness (FIGS. 9A-9D, FIG. 14A, FIGS. 15A-15B, FIG. 17 and FIG. 18) and growth factor-biopatterning (FIGS. 19A-19E, FIG. 23 and FIG. 24), respectively. Substrate stiffness imparts biomechanical cues[37] and was achieved by varying UV exposure to effect musculoskeletal differentiation at physiologically-relevant stiffness. Stiffer QHM polymers increased and decreased growth factor-mediated osteoblast and tenocyte differentiation, respectively (FIGS. 9A-9D, FIG. 14A, FIGS. 15A-15B, FIG. 17 and FIG. 18). Growth factor biopatterning imparts biochemical cues and was achieved by depositing growth factor(s) onto QHM polymers to effect musculoskeletal differentiation in registration to printed patterns. Biopatterned BMP-2[18,19,29-32] increased osteoblast differentiation in vitro and promoted bone-like formation in vivo (FIGS. 19A-19E, FIG. 23 and FIG. 24). Biopatterned FGF-2[18,19,36] increased tenocyte differentiation in vitro while biopatterned FGF-2 or GDF-7[21,22] promoted tendon-like formation in vivo (FIGS. 19A-19E, FIG. 23 and FIG. 24). Although not addressed here, incorporating additional cues including geometric features and mechanical conditioning may further regulate musculoskeletal differentiation. Thus, substrate stiffness and growth factor-biopatterning spatially controlled bone- and tendon-like differentiation.

Possessing favorable physicochemical characteristics including features for musculoskeletal attachment and slow degradation is vital for eventual graft-host integration. To facilitate clinical translation, QHM polymers were fabricated into a continuous bone-tendon graft (FIGS. 26A-26H). This continuous design innovates upon suture anchors, whose role has not changed since their introduction in 1905. Although optimal degradation rates are patient- and injury-dependent, slow degradation rates are ideal given that rotator cuff injuries heal slowly[7]. Premature, accelerated degradation would compromise the graft's ability to sustain physiological loading and facilitate tissue healing due to rapid loss of graft integrity, the graded interface and growth factor-biopatterned surfaces. Highly crosslinked polyurethanes undergo hydrolysis slowly[43] and explain the slow degradation profile of QHM polymers (FIGS. 26A-26H). Also, in vitro and in vivo studies indicate that QHM polymers or their degradation products exhibited little-to-no cytotoxicity (FIGS. 12A-12B, 13A-13B, 19D-19E, and 26F-26G). Thus, QHM polymers possessed physicochemical characteristics favorable for bone-tendon repair.

An embodiment of the invention relates to a polyurethane comprising a reaction product of a polyol, a polyisocyanate, and an acrylate.

Some embodiments of the invention relates to the polyurethane above, where the polyol is selected from a group consisting of glycerol, erythritol, threitol, arabitol, xylitol, ribitol, pentaerythritol, dipentaerythritol, mannitol, sorbitol, galactitol, iditol, volemitol, fucitol, inositol, maltitol, lactitol, isomalt, maltotritol, maltotetraitol, polyglycitol, polymeric triols, ethylene oxide triols, polycaprolactone triols, polycarbonate triols, polymeric tetrols, polycaprolactone tetrols, 1,1,1-tris(hydroxymethyl)ethane and 1,1,1-tris(hydroxymethyl)propane.

Some embodiments of the invention relates to the polyurethane above, where the polyol further comprises a tertiary amine.

Some embodiments of the invention relates to the polyurethane above, where the polyol is selected from a group consisting of N,N,N',N'-tetrakis(2-hydroxyethyl)ethylenediamine, triethanol amine, triisopropanolamine, 1-[N,N-bis(2-hydroxyethyl)amino]-2-propanol, and 4-[N,N-bis(2-hydroxyethyl)amino]benzaldehyde.

Some embodiments of the invention relates to the polyurethane above, where the polyisocyanate is selected from a group consisting of isophorone diisocyanate, methylene dicyclohexyl diisocyanate, 2,4-diisocyanatotoluene, 4,4'-methylene bis-(cyclohexylisocyanate), hexamethylene diisocyanate, biuret of hexamethylene diisocyanate, hexamethylene diisocyanate isocyanurate trimer, hexamethylene diisocyanate uretdione, poly(hexamethylene diisocyanate), isophorone diisocyanate trimer, 1,3 cyclohexane bis(methylisocyanate), and 2,2,4,-trimethylhexamethylene diisocyanate.

Some embodiments of the invention relates to the polyurethane above, where the acrylate is selected from the group consisting of methyl acrylate, ethyl acrylate, methyl methacrylate, acrylic anhydride, acrylamide, methacrylamide, acrylic acid, and methacrylic acid.

Some embodiments of the invention relates to the polyurethane above, where the polyol and the acrylate are combined as a single compound.

Some embodiments of the invention relates to the polyurethane above, where the compound is selected from pentaerythritol triacrylate or glycerol 1,3-diglycerolate diacrylate.

Some embodiments of the invention relates to the polyurethane above, where the polyol comprises N,N,N',N'-tetrakis(2-hydroxyethyl)ethylenediamine, the polyisocyanate comprises hexamethylene diisocyanate, and the photocrosslinkable acrylate comprises methacrylic anhydride.

Another embodiment of the invention relates to a bone-tendon graft biomaterial comprising the polyurethane above, where the biomaterial has a gradient of mechanical properties through photocrosslinking such that a first end of the biomaterial is crosslinked at a higher degree than a second end, and the first end of the biomaterial has mechanical properties of bone and the second end of the biomaterial has mechanical properties of tendon.

Some embodiments of the invention relates to the bone-tendon graft biomaterial above, where the first end is shaped to constitute a bone anchor adapted to connect to a bone. the first end and the second end having a tensile strength in a range of from about 4.0 to about 170.0 MPa, a tensile modulus in a range of from about 0.6 to about 29.0 GPa, a compressive strength in a range of from about 58 to about 213 MPa, and a compressive modulus in a range of from about 1.5 to about 34.3 GPa.

Some embodiments of the invention relates to the bone-tendon graft biomaterial above, where the first end is shaped to constitute a bone anchor adapted to connect to a bone. the first end and the second end having a tensile strength in a range of from about 12 to about 74 MPa, a tensile modulus in a range of from about 0.6 to about 2.7 GPa, a compressive strength in a range of from about 58 to about 121 MPa, and a compressive modulus in a range of from about 1.5 to about 3.1 GPa.

Some embodiments of the invention relates to the bone-tendon graft biomaterial above, where the first end is shaped to constitute a bone anchor adapted to connect to a bone. the first end having a tensile strength of from about 66 to about 170.0 MPa, a tensile modulus of from about 11 to about 29.0 GPa, a compressive strength of from about 167 to about 213 MPa, and a compressive modulus of from about 14.7 to about 34.3 GPa.

Some embodiments of the invention relates to the bone-tendon graft biomaterial above, where the first end is shaped to constitute a bone anchor adapted to connect to a bone. the second end having a tensile strength of from about 4 to about 22 MPa and a tensile modulus of from about 0.2 to about 0.6 GPa.

Some embodiments of the invention relates to the bone-tendon graft biomaterial above, further comprising one or more growth factor.

Some embodiments of the invention relates to the bone-tendon graft biomaterial above, wherein the growth factors is selected from a group consisting of bone morphogenetic proteins (BMPs), fibroblast growth factors (FGFs), growth and differentiation factors (GDFs), platelet-derived growth factor, transforming growth factor-beta (TGF-betas), platelet-rich plasma, other connective tissue growth factors, as well as other known bone- and tendon-promoting growth factors and biological agents.

Some embodiments of the invention relates to bone-tendon graft biomaterial above, wherein the BMPs includes BMP-2 and BMP-7, the FGFs includes FGF-2, FGF-4, and the GDFs includes GDF-5/BMP-14/CDMP-1, GDF-6/BMP-13/CDMP-2 and GDF-7/BMP-12. Transforming growth factor-betas include TGF-$\beta$1, TGF-$\beta$2 and TGF-$\beta$2

Another embodiment of the invention relates to a method of making a bone-tendon graft biomaterial, comprising mixing a polyol, a polyisocyanate, and an acrylate to form a polyurethane pre-mixture; degassing the polyurethane pre-mixture under vacuum; transferring the polyurethane pre-mixture to a mold; reacting the polyurethane pre-mixture under vacuum or in an inert atmosphere to form an intermediate material; UV-curing the intermediate material by exposure to UV light; placing the intermediate material under pressure in an inert atmosphere; and heat-curing the intermediate material to form the bone-tendon graft biomaterial.

Some embodiments of the invention relates to the method above, further comprising applying a mask to control the exposure to UV light when forming the intermediate material, wherein the mask comprises a translucent/semi-transparent material.

Some embodiments of the invention relates to the method above, further comprising moving the mask gradually along a length of the polyurethane pre-mixture during the curing.

Some embodiments of the invention relates to the method above, where the mask provides levels of shade during the curing to allow varying a degree of exposure to UV light to the polyurethane pre-mixture to create a gradient of mechanical properties similar to bone at one end of the biomaterial and similar to tendon at another end of the biomaterial.

Some embodiments of the invention relates to the method above, further comprising coating at least one extracellular matrix material onto the bone-tendon graft biomaterial.

Some embodiments of the invention relates to the method above, further comprising incorporating at least one growth factor in the bone-tendon graft biomaterial.

Some embodiments of the invention relates to the method above, where the incorporating is selected from biopatterning, pipetting, brushing, inkjet printing, jetting, dipping, or acoustic droplet ejecting.

Some embodiments of the invention relates to the method above, where the degassing is in the absence of a solvent, catalyst or photoinitiator.

Another embodiment of the invention relates to a bone-tendon graft biomedical device comprising a biocompatible polyurethane material formed in a structure having a first end that has mechanical properties adapted for attachment to bone and a second end that has mechanical properties adapted for attachment to at least one of tendon or muscle, wherein said polyurethane comprises a reaction product of a polyol, a polyisocyanate, and an acrylate, and wherein said polyurethane is crosslinked at a higher degree at the first end than at the second end.

Some embodiments of the invention relates to the bone-tendon graft biomedical device above, where the first end is shaped to constitute a bone anchor adapted to connect to a bone.

Some embodiments of the invention relates to the bone-tendon graft biomedical device above, where the first end is shaped to constitute a bone anchor adapted to connect to a bone. The bone anchor is adapted for placement in a bone.

Some embodiments of the invention relates to the bone-tendon graft biomedical device above, where the first end is shaped to constitute a bone anchor adapted to connect to a bone. The bone anchor may be shaped in any form such that the bone anchor can be adapted to the bone. For example, the bone anchor may have an end that is flat, pierced, pointed or barbed. In other embodiments, the bone anchor can be shaped like a non-threaded nail, or taper nail which can be hammed into the bone. The bone anchor may be a sharp nail-liked lip. The bone anchor may also have a smooth tapered stem.

Some embodiments of the invention relates to the bone-tendon graft biomedical device above, where the first end is shaped to constitute a bone anchor adapted to connect to a bone. The bone anchor includes screw threads to screw the bone anchor into bone. The bone screw may contain one or more penetrating holes to facilitate the connection between the bone anchor and the host bone or the bone anchor and the host bone tissue. In other embodiments, the bone anchor may be hollowed.

Some embodiments of the invention relates to the bone-tendon graft biomedical device above, wherein the bone anchor may have a combination of threaded and sharp end.

Some embodiments of the invention relates to the bone-tendon graft biomedical device above, where the first end is shaped to constitute a bone anchor adapted to connect to a bone. The second end extending from the first end having mechanical properties of a tendon and suitable for placement of a suture.

Some embodiments of the invention relates to the bone-tendon graft biomedical device above, where the first end is shaped to constitute a bone anchor adapted to connect to a bone. the polyol is selected from a group consisting of glycerol, erythritol, threitol, arabitol, xylitol, ribitol, pentaerythritol, dipentaerythritol, mannitol, sorbitol, galactitol, iditol, volemitol, fucitol, inositol, maltitol, lactitol, isomalt, maltotritol, maltotetraitol, polyglycitol, polymeric triols, ethylene oxide triols, polycaprolactone triols, polycarbonate triols, polymeric tetrols, polycaprolactone tetrols, 1,1,1-tris(hydroxymethyl)ethane and 1,1,1-tris(hydroxymethyl)propane.

Some embodiments of the invention relates to the bone-tendon graft biomedical device above, where the first end is shaped to constitute a bone anchor adapted to connect to a bone. The polyol further comprises a tertiary amine.

Some embodiments of the invention relates to the bone-tendon graft biomedical device above, where the first end is shaped to constitute a bone anchor adapted to connect to a bone. the polyol is selected from a group consisting of N,N,N',N'-tetrakis(2-hydroxyethyl)ethylenediamine, triethanol amine, triisopropanolamine, 1-[N,N-bis(2-hydroxyethyl)amino]-2-propanol, and 4-[N,N-bis(2-hydroxyethyl)amino]benzaldehyde.

Some embodiments of the invention relates to the bone-tendon graft biomedical device above, where the first end is shaped to constitute a bone anchor adapted to connect to a bone. the polyisocyanate is selected from a group consisting of isophorone diisocyanate, methylene dicyclohexyl diisocyanate, 2,4-diisocyanatotoluene, 4,4'-methylene bis-(cyclohexylisocyanate), hexamethylene diisocyanate, biuret of hexamethylene diisocyanate, hexamethylene diisocyanate isocyanurate trimer, hexamethylene diisocyanate uretdione, poly(hexamethylene diisocyanate), isophorone diisocyanate trimer, 1,3 cyclohexane bis(methylisocyanate), and 2,2,4,-trimethylhexamethylene diisocyanate.

Some embodiments of the invention relates to the bone-tendon graft biomedical device above, where the first end is shaped to constitute a bone anchor adapted to connect to a bone. The acrylate is selected from the group consisting of methyl acrylate, ethyl acrylate, methyl methacrylate, acrylic anhydride, acrylamide, methacrylamide, acrylic acid, and methacrylic acid.

Some embodiments of the invention relates to the bone-tendon graft biomedical device above, where the first end is shaped to constitute a bone anchor adapted to connect to a bone. The polyol and the acrylate are combined as a single compound.

Some embodiments of the invention relates to the bone-tendon graft biomedical device above, where the first end is shaped to constitute a bone anchor adapted to connect to a bone. The compound is selected from pentaerythritol triacrylate or glycerol 1,3-diglycerolate diacrylate.

Some embodiments of the invention relates to the bone-tendon graft biomedical device above, where the first end is shaped to constitute a bone anchor adapted to connect to a bone. The polyol comprises N,N,N',N'-tetrakis(2-hydroxyethyl)ethylenediamine, the polyisocyanate comprises hexamethylene diisocyanate, and the photocrosslinkable acrylate comprises methacrylic anhydride.

Some embodiments of the invention relates to the bone-tendon graft biomedical device above, where the first end is shaped to constitute a bone anchor adapted to connect to a bone. the first end and the second end having a tensile strength in a range of from about 4.0 to about 170.0 MPa, a tensile modulus in a range of from about 0.6 to about 29.0 GPa, a compressive strength in a range of from about 58 to about 213 MPa, and a compressive modulus in a range of from about 1.5 to about 34.3 GPa.

Some embodiments of the invention relates to the bone-tendon graft biomedical device above, where the first end is shaped to constitute a bone anchor adapted to connect to a bone. the first end and the second end having a tensile strength in a range of from about 12 to about 74 MPa, a tensile modulus in a range of from about 0.6 to about 2.7 GPa, a compressive strength in a range of from about 58 to about 121 MPa, and a compressive modulus in a range of from about 1.5 to about 3.1 GPa.

Some embodiments of the invention relates to the bone-tendon graft biomedical device above, where the first end is shaped to constitute a bone anchor adapted to connect to a bone. the first end having a tensile strength of from about 66 to about 170.0 MPa, a tensile modulus of from about 11 to about 29.0 GPa, a compressive strength of from about 167 to about 213 MPa, and a compressive modulus of from about 14.7 to about 34.3 GPa.

Some embodiments of the invention relates to the bone-tendon graft biomedical device above, where the first end is shaped to constitute a bone anchor adapted to connect to a bone. the second end having a tensile strength of from about 4 to about 22 MPa and a tensile modulus of from about 0.2 to about 0.6 GPa.

Some embodiments of the invention relates to the bone-tendon graft biomedical device above, where the first end is shaped to constitute a bone anchor adapted to connect to a bone comprising a growth factor.

Some embodiments of the invention relates to the biomedical device above, where the first end is shaped to constitute a bone anchor adapted to connect to a bone.

Some embodiments of the invention relates to the biomedical device above, where the bone anchor is adapted for placement in a bone.

Some embodiments of the invention relates to the biomedical device above, where the bone anchor has an end that is flat, pierced, pointed or barbed.

Some embodiments of the invention relates to the biomedical device above, where the bone anchor includes screw threads to screw the bone anchor into bone.

Some embodiments of the invention relates to the biomedical device above, where the second end extending from the first end having mechanical properties of a tendon and suitable for placement of a suture.

EXAMPLE

In the following example, it is demonstrated that the inventive polyurethane may be used as a bone-tendon graph biomaterial. The bone-tendon graft biomaterial has mechanical properties in gradient that allows it to have mechanical properties of bone on one end and tendon properties on the opposite end.

Musculoskeletal tissues are multi-functional materials whose structural and architectural compositions optimally fulfill their mechanical and biological functions within local anatomical and material constraints. The bone-tendon interface is a prime example where it must attach compliant tendon to stiff bone in a manner that withstands physiological loading despite severe mismatches in mechanical properties. The stiff nature of bone is a consequence of its role in mineral storage, which protects and houses internal tissues while providing levers for muscles to act on[52]. The compliant nature of tendon is a consequence of its unmineralized collagen matrix, which facilitates transmission of muscular contractile force to bone and elastic energy storage during musculoskeletal movement[52,53]. This attachment of dissimilar materials is challenging because high levels of localized stress may develop at their interfaces. The bone-tendon interface arrives at an elegant solution to this problem by using a gradual transition in extracellular matrix (ECM) composition and structure[54-56] across its interface, effectively minimizing stress concentrations to reduce tearing[54,57-59]. Indeed, variations on this theme are found in nature as well as various engineering applications including bamboo[60], mussels[61], dental implants[62], hip implants[63,64] and soft robotics[65]. Although bone-tendon interfaces are classically categorized as four distinct regions comprising of bone, mineralized fibrocartilage, unmineralized fibrocartilage and tendon, this classification does not fully reflect the gradual transition in mineral accumulation[54-56] and orientation of collagen fibers[54] across this interface, which is achieved via the collective actions of musculoskeletal cells including osteoblasts and tenocytes[1,54-59,66-68]. Thus, engineering a mechanically-graded material with bone- and tendon-like mechanical properties including the ability to off-set stress concentrations as well as re-establish resident musculoskeletal cells is crucial for successful reattachment and regeneration of stiff bone to compliant tendon following injury.

To engineer biomaterials that sustain physiologically-relevant loading, at least three criteria inherent in the mechanical properties of bone-tendon tissues must be achieved. First, human supraspinatus tendon has a tensile strength of 4-22 MPa[39,40] and a tensile modulus of 0.2-0.6 GPa[40] while cortical bone has a tensile strength of 66.0-170.0 MPa, a tensile modulus of 11.0-29.0 GPa, a compressive strength of 167-213 MPa and a compressive modulus of 14.7-34.3 GPa[41,42]. These properties are important since bone tissues are often subjected to compressive and tensile forces while tendon tissues, particularly at locations they wrap around bony or fibrous pulleys as well as the fibrocartilaginous transitional regions experience both tensile and compressive stress[57,58]. Second, human supraspinatus tendon itself is not a homogenous material and can be divided into at least two[40] or three[39] distinct regions, each with individual mechanical properties. As such, biomaterial fabrication and/or processing techniques must enable material inhomogeneity to be tailored with relative ease. Third, gradation of humeral bone-supraspinatus tendon interface is presumed to reduce stress concentrations and minimize tissue tearing[1-4,9,54-59,66-69]. The importance of possessing physiological mechanical properties has been demonstrated in studies[70,71] which show that tendon stiffness influences musculoskeletal efficiency and performance. Also, degeneration of the bone-tendon interface has been correlated with decreased supraspinatus tendon tensile strength[72]. Thus, biomaterials lacking these attributes are not expected to sustain physiological loading.

In order to support physiologically-relevant loading, commercially-available grafts and research efforts must approximate the mechanical properties of bone-tendon tissues. Commercially-available grafts possess tensile strengths that approximate or exceed tendon tissue (11.9-32.7 MPa)[10], however, their tensile modulus (14-71 MPa)[10] are approximately 3-42 times lower than native supraspinatus tendon (0.2-0.6 GPa)[40]. In addition, commercially-available grafts to date are not mechanically-tunable[8,10,73-77] and lack the means to approximate the inhomogenous nature of human supraspinatus tendon or bone-tendon interface as well as reduce stress concentrations via mechanical-gradation. Research efforts thus far have yielded promising outcomes with the fabrication of tendon-like materials including anisotropically-aligned collagen biotextiles[78,79], layered poly(L-lactic acid) scaffolds[80,81], electrospun nanofibers with crimped morphology[12], collagen scaffolds crosslinked via hypoxia and lysyl oxidase[13], woven poly(L-lactic acid) scaffolds[14] as well as graded materials including multi-phased scaffolds[17,82,83], "aligned-to-random" nanofiber scaffolds[84,85], bone-tendon allografts[86], poly(lactic-co-glycolic Acid) or polycaprolactone nanofibers with mineral gradients[16,87]. However, the resulting material(s) from these studies lacked adequate tensile properties[16,17,79,82-88] or stiffness gradients that reduced stress concentrations[12-14,78-81]. For example, several studies fabricated a gradient of calcium phosphate across electrospun nanofibers[16,87], producing tensile moduli that ranged between 40-120 MPa[16]. These moduli fall short of physiologically-relevant tendon and bone values by 5-15 and 92-242 fold, respectively[39-42]. In addition, current approaches[12-14,16,78-83,87,89] may be challenged to mimic the individual mechanical properties of distinct supraspinatus tendon regions as their fabrication techniques do not allow for variations in mechanical properties to be easily introduced in a spatially-defined manner at physiologically-relevant length scales. Thus, further efforts are required to engineer biomaterials with bone- and tendon-like mechanical properties.

Polyurethanes are polymers linked by carbamate groups with well suited characteristics for biomaterial applications. The diverse array of polyurethane molecular structures and intermolecular interactions including the formation of hard and soft segments has resulted in numerous material categories including flexible foams, rigid foams, elastomers and coatings[90]. As such, polyurethane polymers have found broad clinical use in spinal devices, pacemaker leads, neurological leads, peritoneal dialysis catheters, cardiovascular catheters and antimicrobial wound dressings[90,91]. QHM polymers are UV-crosslinkable polyurethanes (FIGS. 1A-1C and FIGS. 2A-2D) that do not require solvent, catalyst or photoinitiator for fabrication. A solvent was not required as Q, H and M were miscible. In addition, neither a catalyst or photoinitator was required since Q is a tertiary amine that can function as a pseudo catalyst in polyurethane reactions[43,90] whereas M is an acrylic monomer that can undergo self-initiated photopolymerization[44]. The polyurethane carbamate group was formed by the reaction between hydroxyl groups of Q and isocyanate groups of H while the UV-crosslinkable component was formed by the reaction between hydroxyl groups of Q and anhydride carbonyl groups of M (FIGS. 1A-1C and FIGS. 2A-2D). Since Q is a polyol with four hydroxyl groups, its reaction with H and M produced a highly-crosslinked network of polymer chains. Although the reaction of Q and M caused polymer chain termination, additional crosslinks were introduced via UV-exposure of M's vinyl methine groups. In general, highly-crosslinked polymers possess increased molecular weights and mechanical properties[90]. By selecting a desired ratio of Q, H and M monomers as well as varying UV-exposure, the desired level of chemical- and photo-crosslinking within QHM polymer chains were attained. Post-processing of QHM polymers by heat-curing likely promoted physical chain entanglements that contributed further to increased mechanical properties (Data not shown). Ultimately, these two modes of crosslinking together with heat-curing allowed QHM polymers to achieve high, phototunable mechanical properties.

Figure 3A:
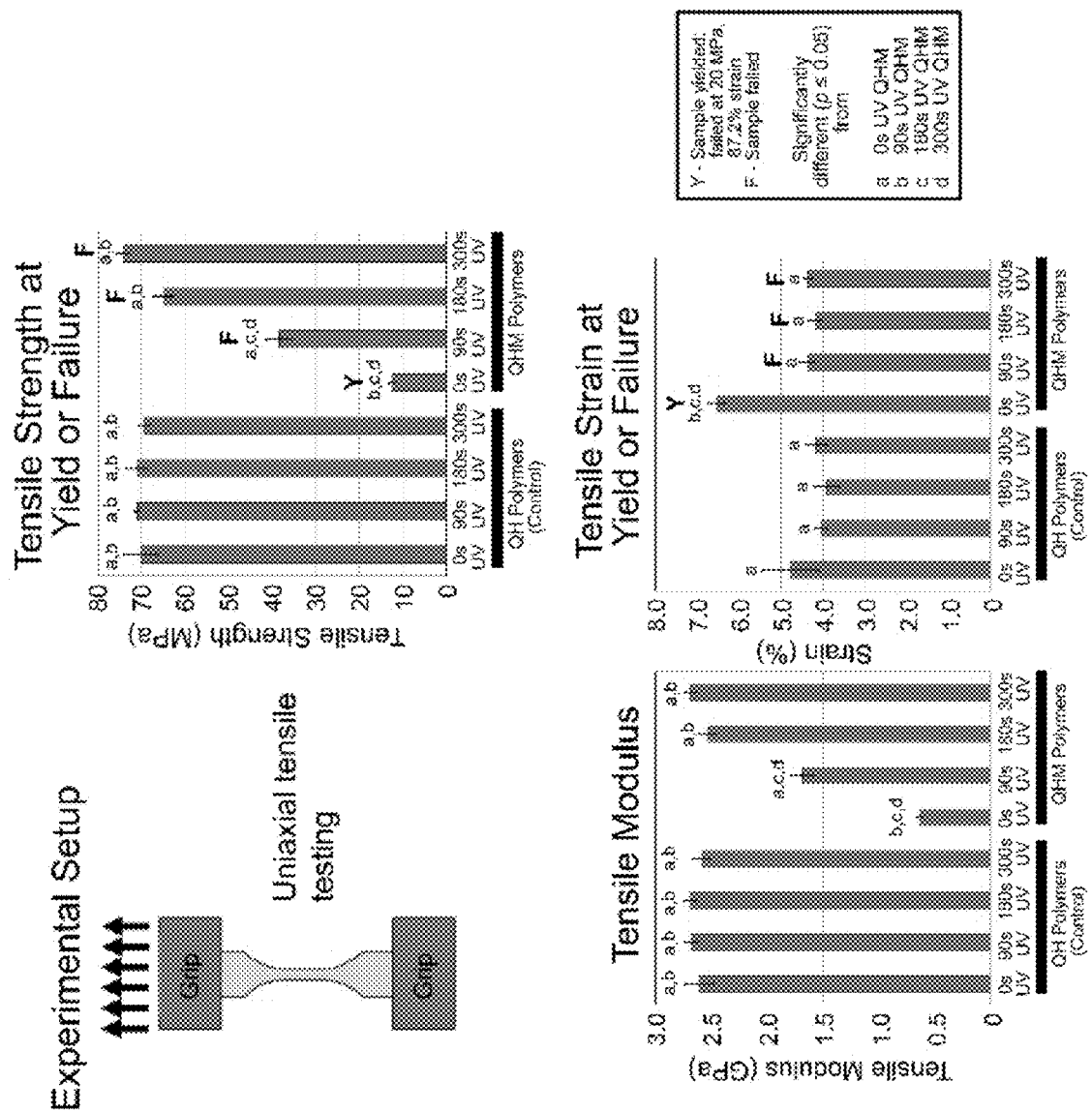
FIGS. 3A-3D show mechanical properties of QHM polymers.
Figure 3B:
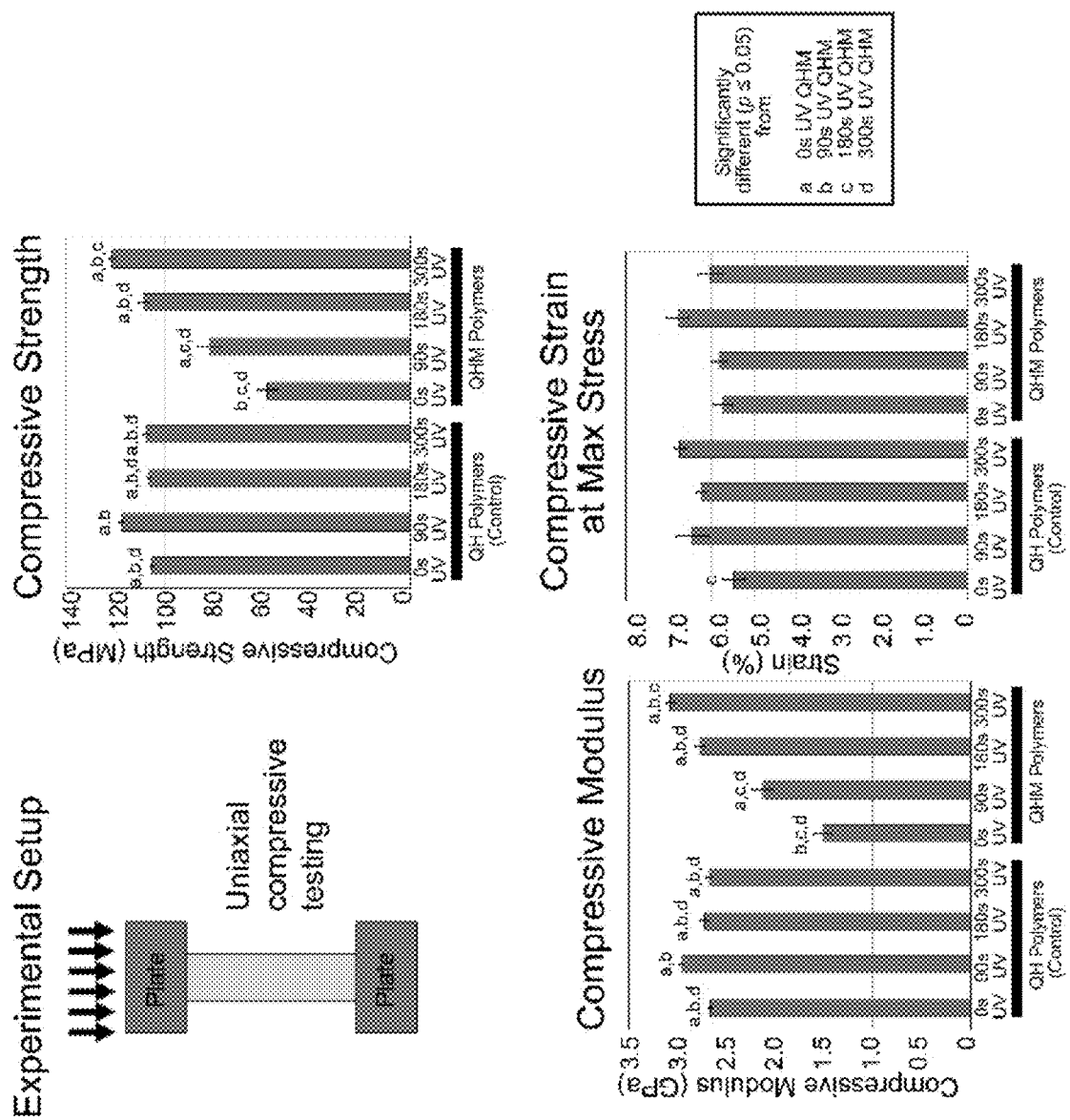
Figure 3C:
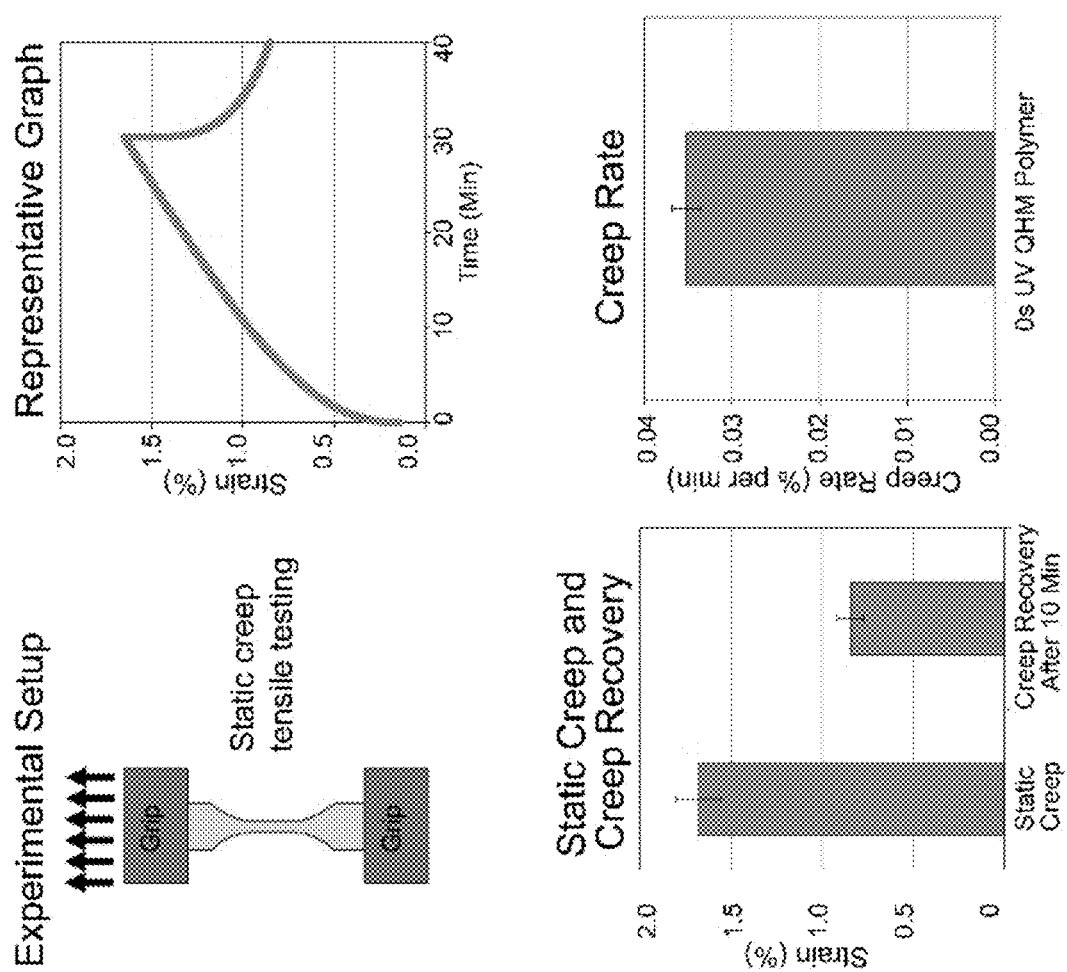
Figure 4A:
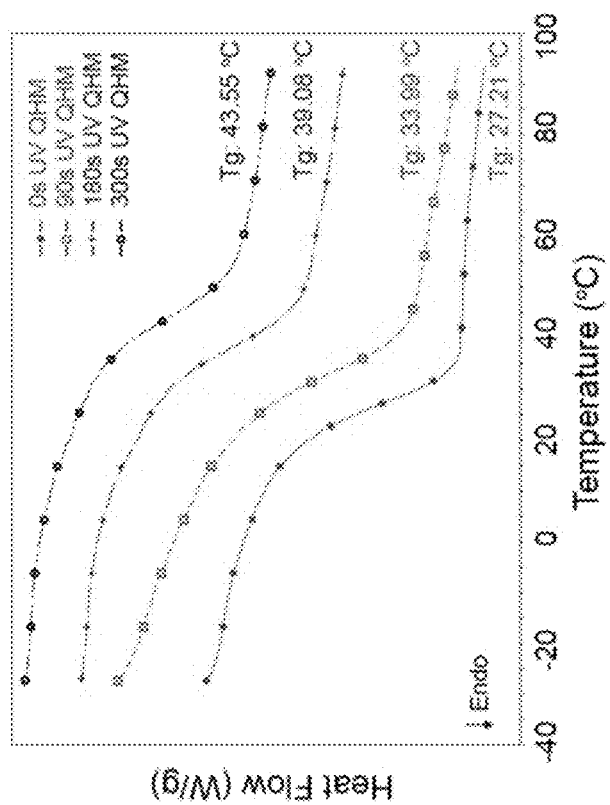
FIGS. 4A and 4B show effect of UV-exposure on glass transition temperature of QHM polymers.
Figure 4B:
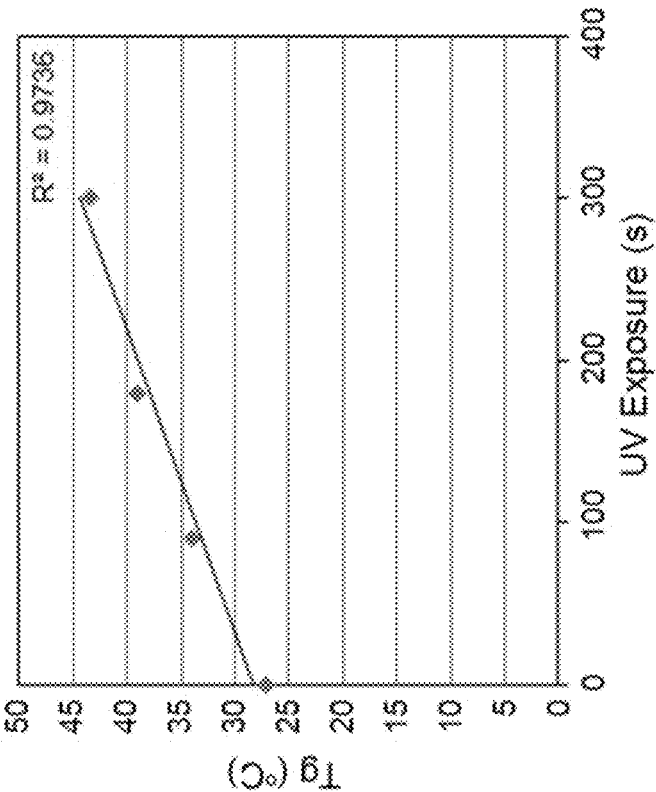
Figure 5A:
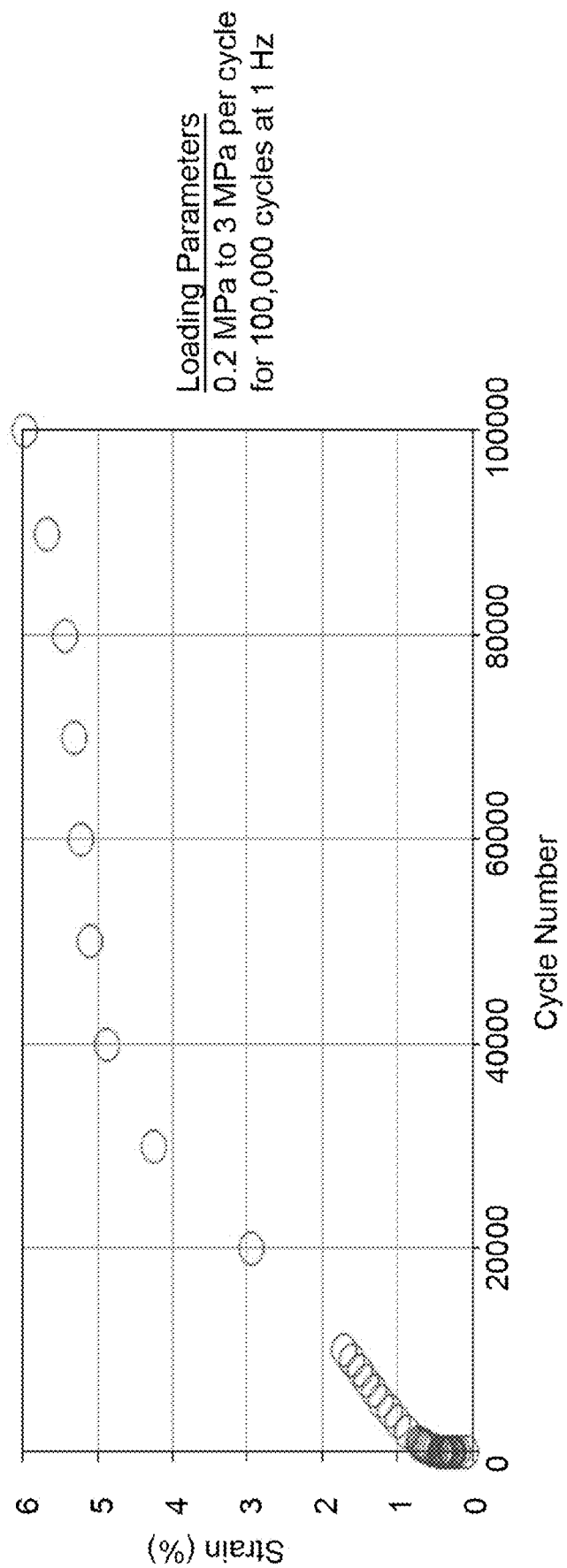
FIGS. 5A and 5B show a graph of cyclic loading and photos of before and after loading measurements.
Figure 5B:
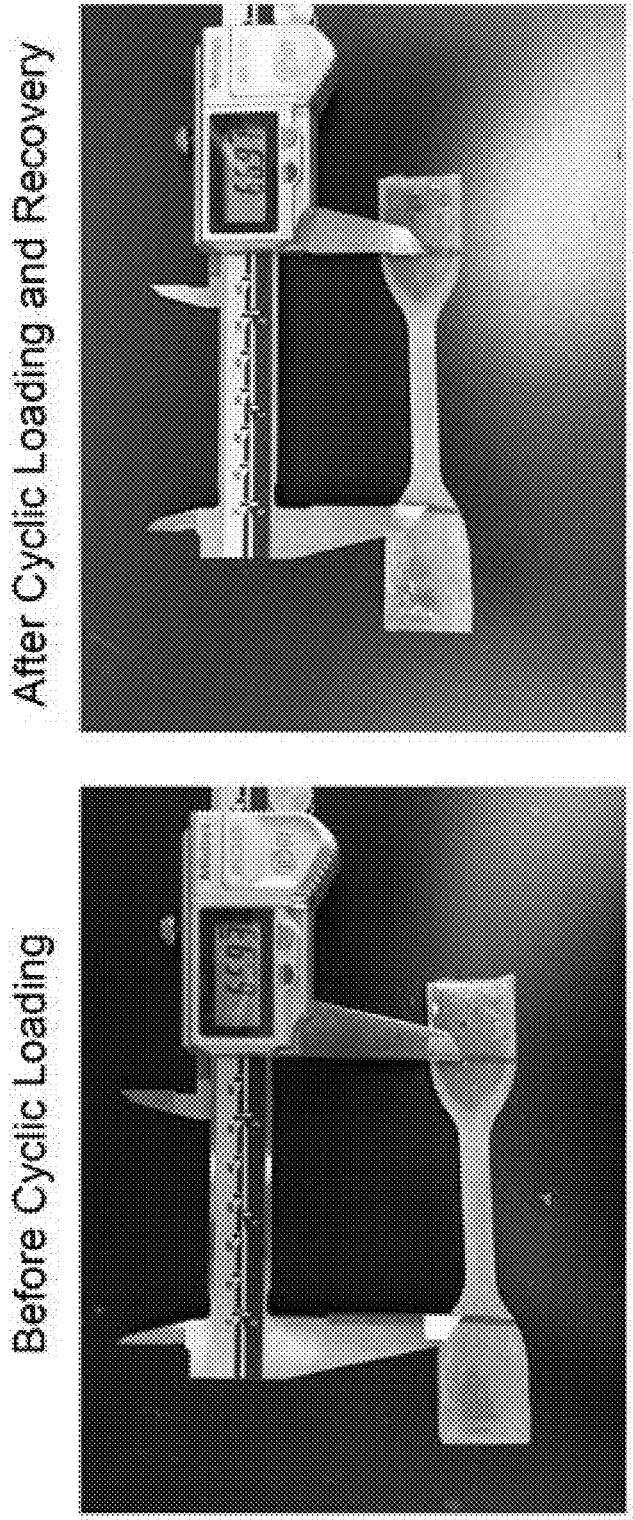

In order to support physiologically-relevant loading, QHM polymers must approximate the mechanical properties of bone-tendon tissues. First, QHM polymer synthesis and processing enabled its mechanical properties to be tunable. These include a tensile strength of 12-74 MPa, a tensile modulus of 0.6-2.7 GPa, a compressive strength of 58-121 MPa and a compressive modulus of 1.5-3.1 GPa (FIGS. 3A-3D), which approximated the mechanical properties of human supraspinatus tendon[39,40] and cortical bone[41,42]. DSC studies showed that the glass transition temperature of 0 s UV, 90 s UV, 180 s UV and 300 s UV QHM polymers were 27.21° C., 33.99° C., 39.08° C. and 43.55° C., (FIGS. 4A-4B). As such, 0 s UV and 90 s UV QHM polymers will exhibit compliance while 180 s UV and 300 s UV QHM polymers will remain stiff at body temperature. Static and cyclic tensile testing showed that 0 s UV QHM polymer exhibited creep behavior and could withstand physiologically-relevant (0.2-3 MPa)[39,40,45,46], tendon-like loading for at least 10,000 cycles without failing (FIGS. 3A-3D). Also, a single specimen loaded for 100,000 cycles creeped 5.7% and did not fail (FIGS. 5A-5B). In addition, the dynamic modulus (1.5-1.8 GPa) and tan δ (0.18-0.20) of 0 s UV QHM polymer approximated the dynamic modulus of sheep plantaris tendon (1.37-1.99 GPa)[92] as well as the tan δ for rabbit Achilles tendon (0.108-0.180)[93]. As such, 0 s UV QHM polymer mimics the dynamic tensile properties of tendon tissue. Second, QHM polymer synthesis and processing (FIGS. 1A-1C, FIGS. 3A-3D and Data not shown) potentially allow the inhomogenous nature of human supraspinatus tendon to be recapitulated. For example, local application of UV-light and heat on QHM polymers may enable distinct human supraspinatus tendon regions[39,40] to be specified in a spatially controlled manner. Third, QHM polymer can be mechanically-graded to reduce stress concentrations. Both finite element analysis and photoelastic tensile testing demonstrated that gradually-graded specimens possessed less stress concentrations than steeply-graded specimens at their interface (FIGS. 6A-6B, FIG. 7, and FIG. 8). These studies also showed that stress increases were concentrated primarily near the interface of the specimen's bottom, stronger/stiffer half whereas stress decreases were concentrated primarily near the interface of the specimen's top, weaker/more compliant half. Mathematical calculations[94-96] and our studies show that the magnitude of this stress concentration can be much higher than the applied stress (FIGS. 6A-6B, FIG. 7, and FIG. 8) and could result in musculoskeletal tissue degeneration or failure, particularly in compromised medical populations such as the osteoporotic and elderly. Furthermore, these results indicate that whether a graded specimen subjected to tensile forces failed at the interface or in the bulk of the specimen's top, weaker/more compliant half was dependent on both the magnitude of the increased stress and the tensile strength of the specimen's individual halves. For example, the specimen's bottom, stronger/stiffer (300 s UV) half had a tensile strength of 74 MPa whereas the specimen's top, weaker/more compliant (90 s UV) had a tensile strength of 38 MPa. If the magnitude of stress concentration exceeded 38 MPa but not 74 MPa, this could explain why graded specimens subjected to tensile testing all failed in the bulk region of the top, weaker/more compliant half as opposed to failing at the interface (Data not shown). Ultimately, such stress concentration reduction is vital for fabricating a continuous bone-tendon graft to minimize further musculoskeletal degeneration and tears for facilitating bone-tendon healing[1,54-59,66-68]. Together, these results demonstrated that QHM polymers possessed bone- and tendon-like mechanical properties.

In addition to sustaining physiologically-relevant loading, prior studies also supplemented biological cues to direct healing of bone-tendon tissues. In particular, re-establishing osteoblasts and tenocytes is important since they are involved in regulating turnover of bone and tendon ECM in response to mechanical loading[97-99]. Biological cues are often provided in the form of scaffolds, growth factors, cells or various combinations thereof. While this categorization is not all-inclusive and the approaches vary, the goal of supplementing such cues is to promote tissue repair[100]. Scaffold-based approaches include anisotropic collagen-glycosaminoglycan scaffolds[15,101], calcium phosphate scaffolds[102,103] and bone-tendon grafts[86,104]. Growth factor-based approaches include bone morphogenetic proteins (BMPs) such as BMP-2[105,106] and BMP-7[107], fibroblast growth factors (FGFs) such as FGF-2[108-111], growth and differentiation factors (GDFs) such as GDF-5[22], GDF-6[22] and GDF-7[21,22,112,113], platelet-derived growth factor[114], transforming growth factor-beta[102,115], and platelet-rich plasma[20,105]. Cell-based approaches include adipose-derived stem cells[113,116], induced pluripotent stem cells[117], mesenchymal stem cells[21], mkx-engineered mesenchymal stem cells[26], runx2-engineered cells[27,118], smad8/bmp-2-engineered mesenchymal stem cells[25,119], scaffold-free tissue spheroids[120] and scx-engineered stem cells[23,24]. These studies[15,20-27,86,101-120] have yielded promising outcomes but further improvements are required. For example, superior re-cellularization and graft-host integration was achieved using a canine bone-tendon allograft compared to commercially-available GraftJacket, however, mechanical stiffness of the repaired infraspinatus muscle-tendon-bone complex was still inferior to native canine shoulder[86]. Also, simultaneous spatial control of osteoblast and tenocyte differentiation, which is vital for regenerating injured bone-tendon tissues[1,54-59,66-68] was not demonstrated in several of these studies[15,20-27,86,101-120]. Thus, further efforts are required to engineer biomaterials with bone- and tendon-promoting cues in a spatially defined manner.

Prior to determining if QHM polymers could spatially direct multi-tissue phenotypes, several study considerations and methodological criteria were contemplated. C3H10T1/2 and C2C12 cells were utilized as musculoskeletal progenitor models given their similar differentiation capabilities to mesenchymal and muscle stem cells, respectively[18,19,29,30,121], which highlighted their potential for musculoskeletal tissue engineering. For example, a recent study compared tenocytes, dermal fibroblasts and muscle-derived cells for engineering tendon-like tissue[121]. Muscle-derived cells proliferated faster than dermal fibroblasts or tenocytes, shared closer gene expression profiles with tenocytes compared to dermal fibroblasts and formed engineered tendon constructs with stronger tensile properties compared to either dermal fibroblast- or tenocyte-based constructs[121]. In addition, given that mesenchymal and muscle-derived cells can differentiate into myocytes[122-125], these cells show promise for treating fatty-degenerated muscle, which often accompanies severely-compromised rotator cuff tissues[7]. BMP-2 was used to promote osteoblast differentiation as well as bone-like formation[18,19,29-32], which were assessed by staining for ALP activity[126,127], RUNX2, OCN, collagen (Trichrome and polarized light microscopy)[128,129], mineralization[130] and TRAP activity[131]. FGF-2[18,19,36] and GDF-7[21,22] were used to promote tenocyte differentiation as well as tendon-like formation, which were assessed by staining for SCX[36,132,133], TENOMODULIN[134], TENASCIN C (FIG. 17)[135] and collagen (Trichrome and polarized light microscopy)[136]. QHM polymer substrates (0-300 s UV-exposure) were used since their mechanical properties (FIGS. 3A-3D) approximated those of human supraspinatus tendon[39,40] and cortical bone[41,42]. Fibrochondrocytes, although present in the bone-tendon interface, were not spatially patterned as this study sought to recapitulate major features of bone-tendon tissues only. Reproducing a native bone-tendon interface in its entirety would increase material complexity to burden clinical translation and regulatory approval. Also, massive tendon tears that may benefit from grafting are typically several centimeters in size whereas the bone-tendon interface is only several hundred microns in length. Since such injuries are several orders of magnitude larger than the transitional region and stress concentrations can be reduced by mechanical-gradation, fibrochondrocyte patterning was not considered at this time. In addition, fibrochondrocyte transitional regions in the mouse shoulder develop and mineralize postnatally but both processes are impaired when mechanical loading is disrupted[1]. This raises the possibility that fibrochondrocyte regions may be patterned following restoration of physiological shoulder movement with a continuous, graded scaffold containing bone- and tendon-like cells. Together, these study and methodological considerations facilitated investigations on the effect of substrate stiffness and growth factor-biopatterning on osteoblast and tenocyte differentiation in QHM polymers.

Figure 13B:
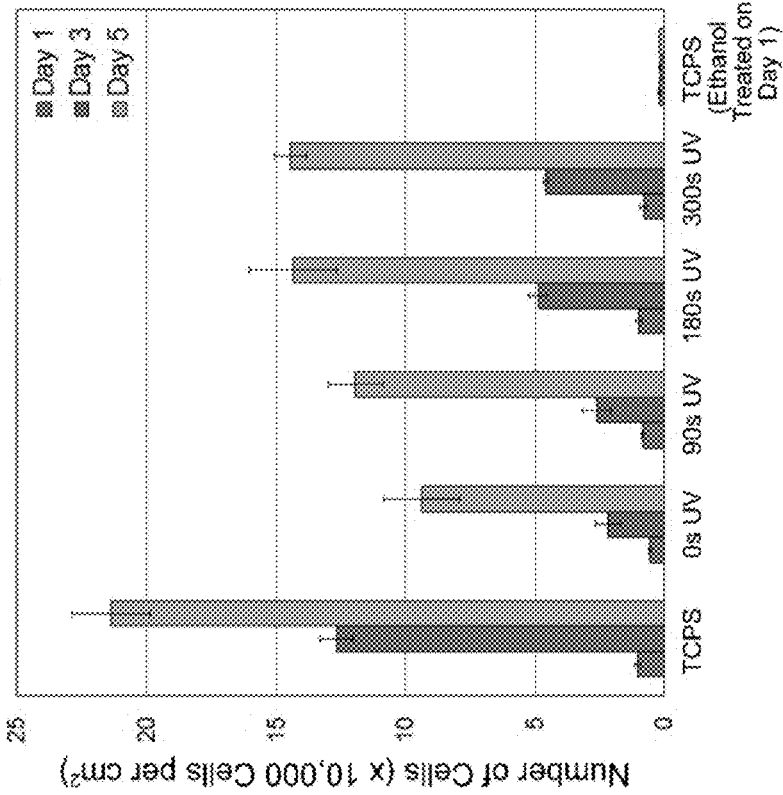
FIGS. 13A and 13B show images and a graph of cell viability and cell proliferation of C2C12 cells on QHM polymers and tissue culture-treated.
Figure 13A:
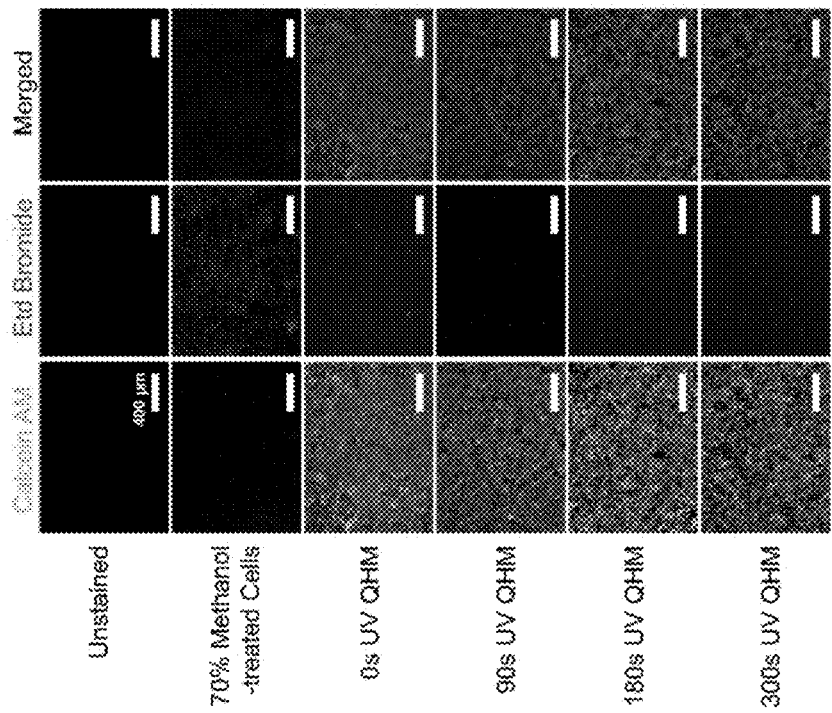
Figure 14A:
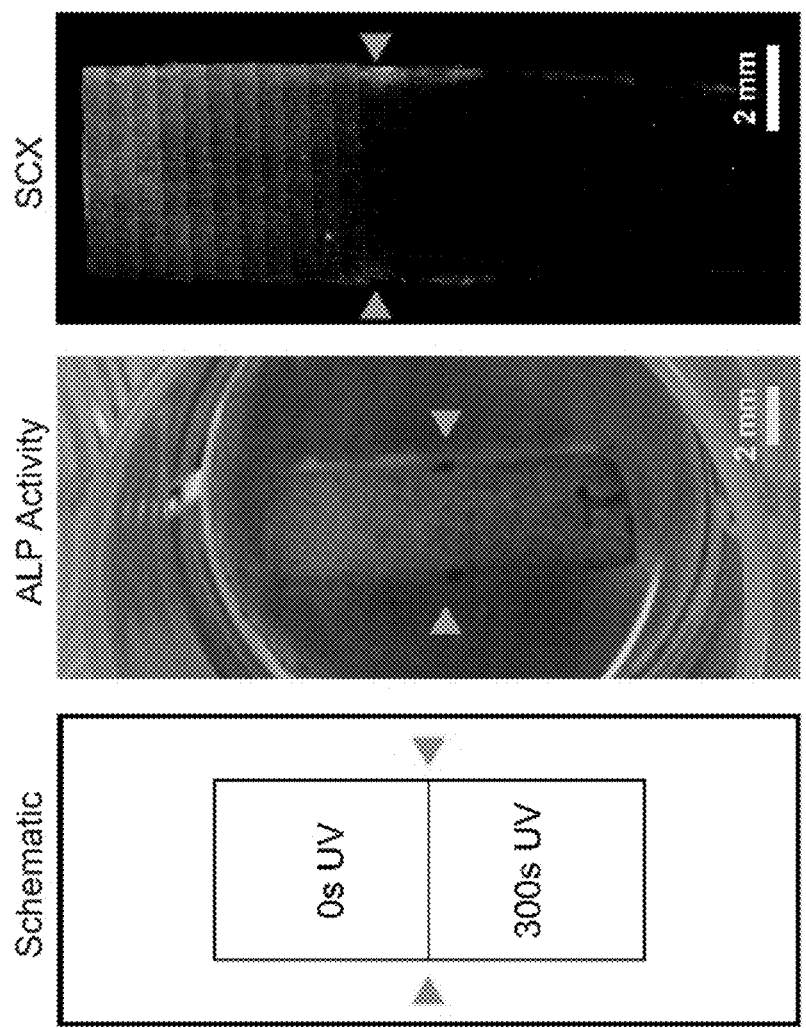
FIGS. 14A and 14B show effect of mechanically-graded (0 s and 300 s UV) and uniform QHM polymers on C2C12 osteoblast and tenocyte differentiation.
Figure 14B:
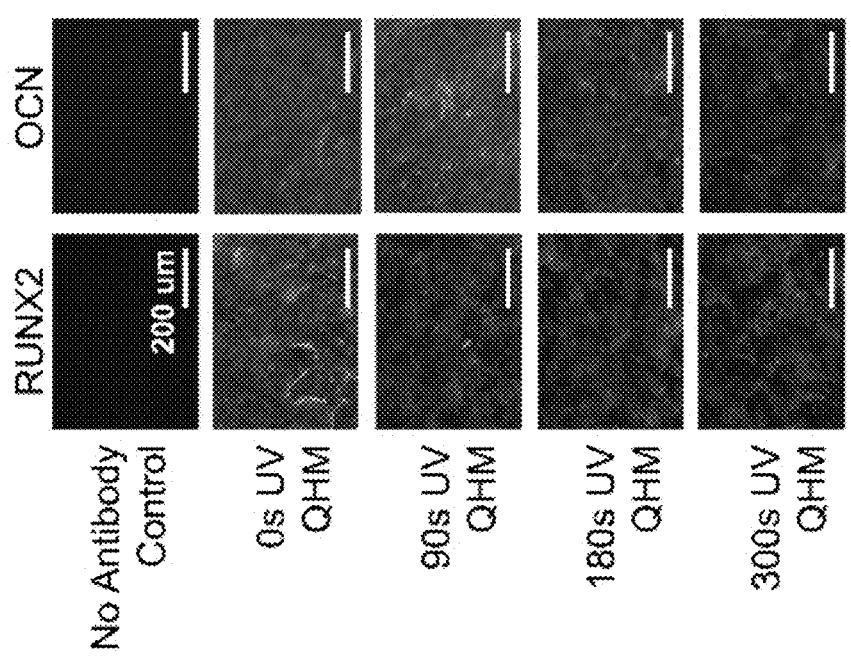
Figure 15A:
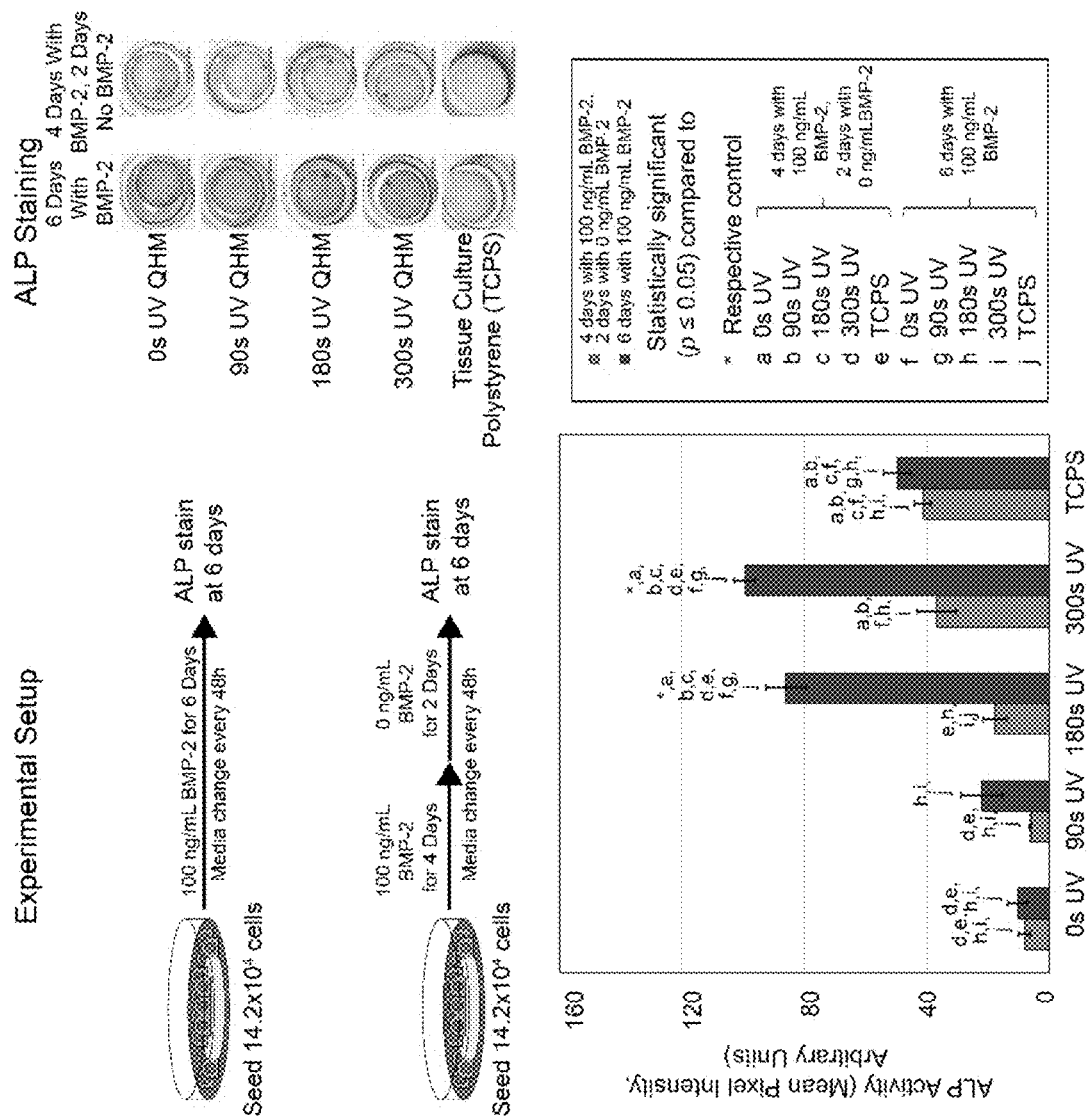
FIGS. 15A and 15B show effect of BMP-2 administration and dose on C2C12 osteogenic differentiation on QHM polymers.
Figure 15B:
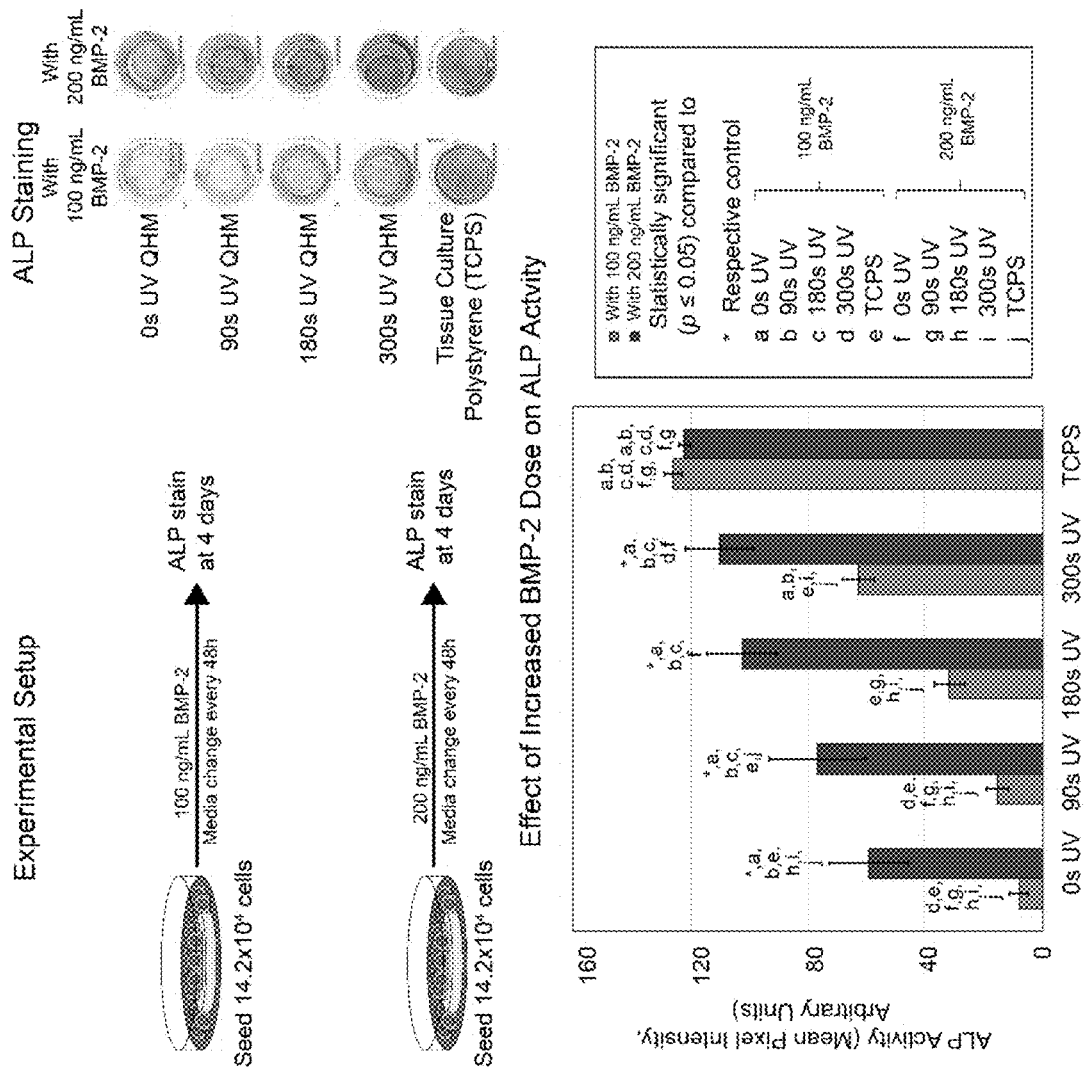
Figure 16:
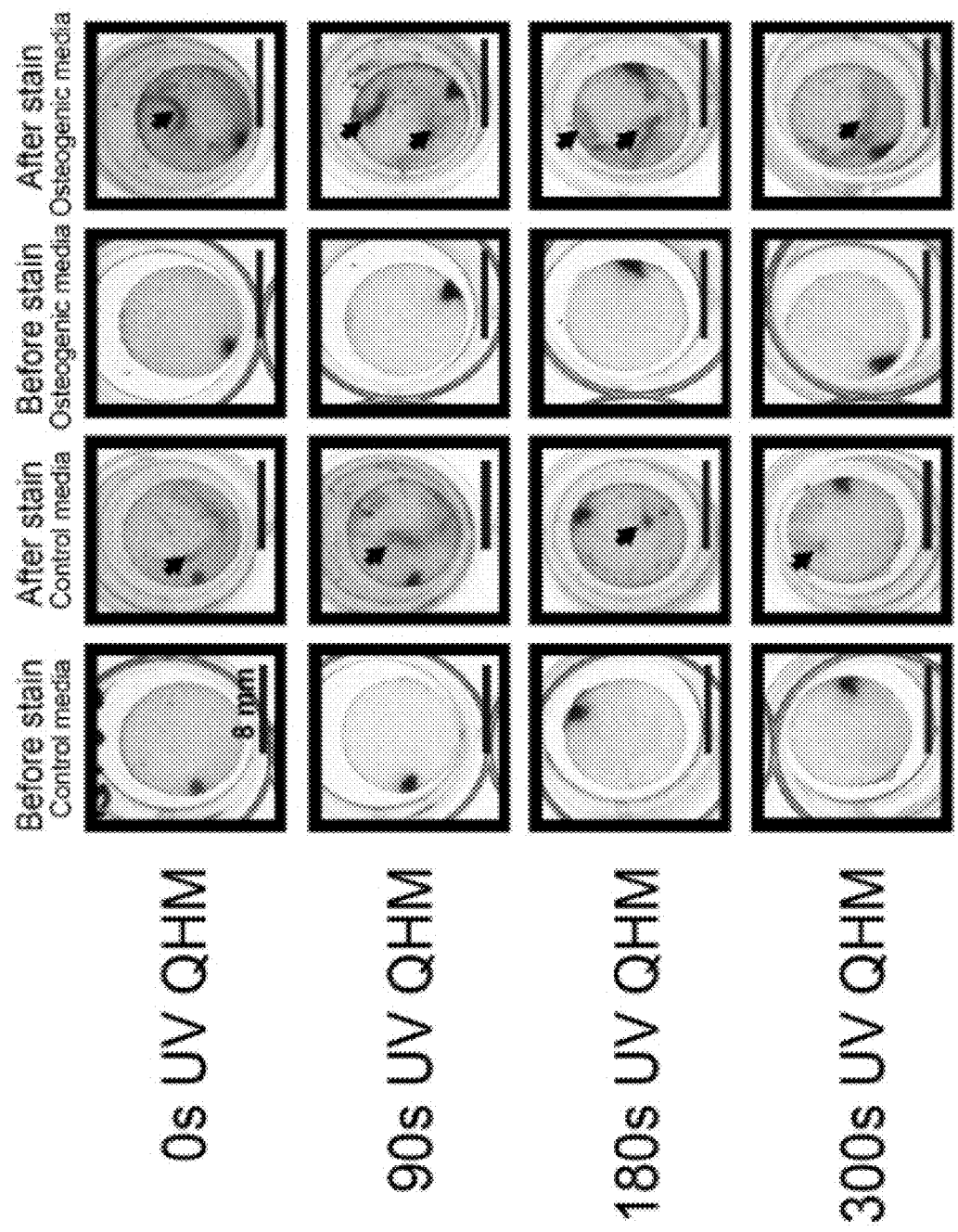
FIG. 16 shows the effect of control and osteogenic media on the differentiation of C2C12 cells on QHM polymers after 27 days culture. Representative images of von-Kossa-stained samples are shown (n=3). von Kossa-positive regions stained black (Black arrows). Scale bars 8 mm.
Figure 17:
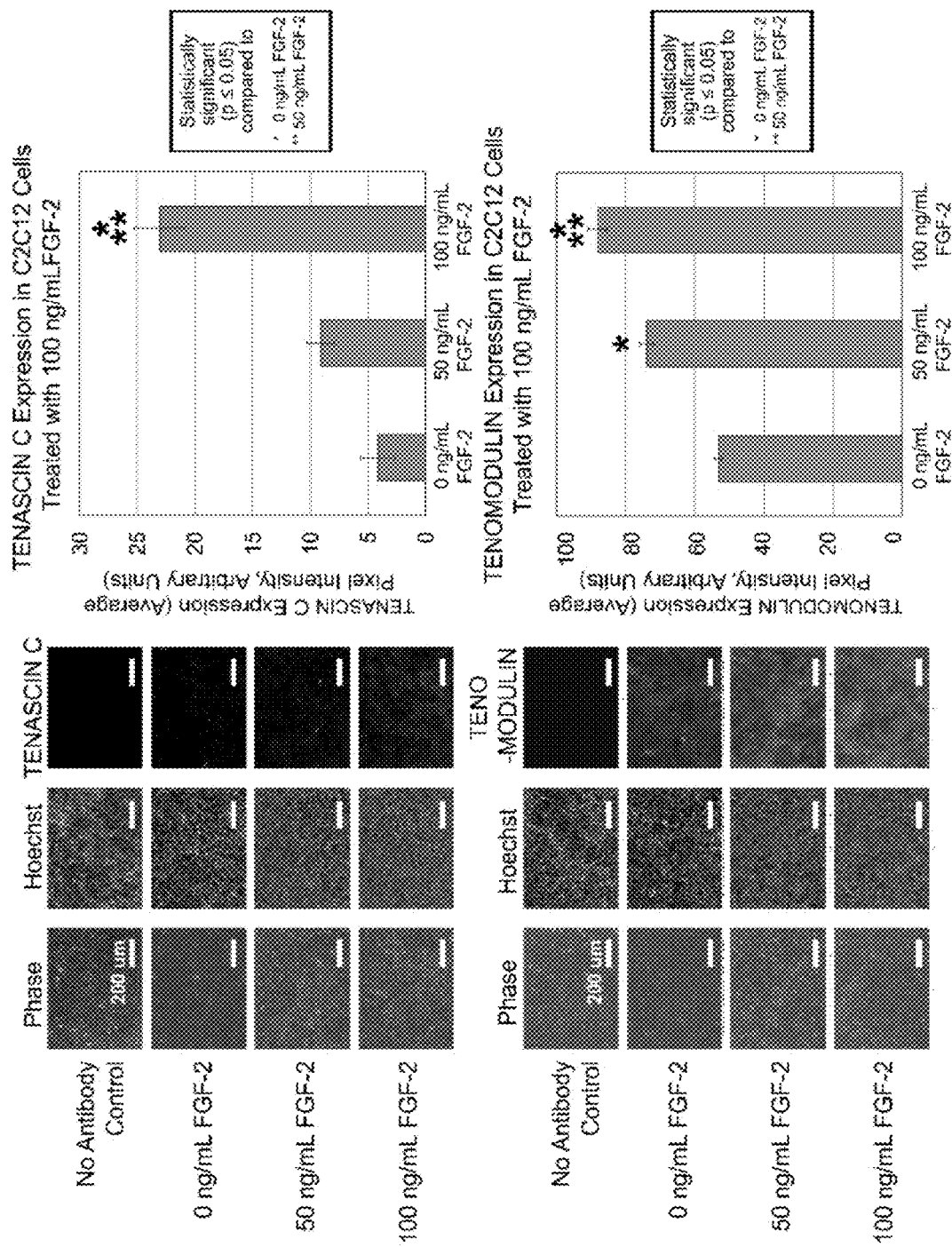
FIG. 17 shows the effect of FGF-2 on C2C12 tenocyte differentiation on tissue culture-grade polystyrene (TCPS) after 3 days culture. FGF-2-treated C2C12 cells showed increased expression of TENASCIN C and TENOMODU- LIN on TCPS (n=9). Scale bars 200 µm. Error bars indicate standard error of mean. Statistical significance (p≤0.05) as indicated.
Figure 18:
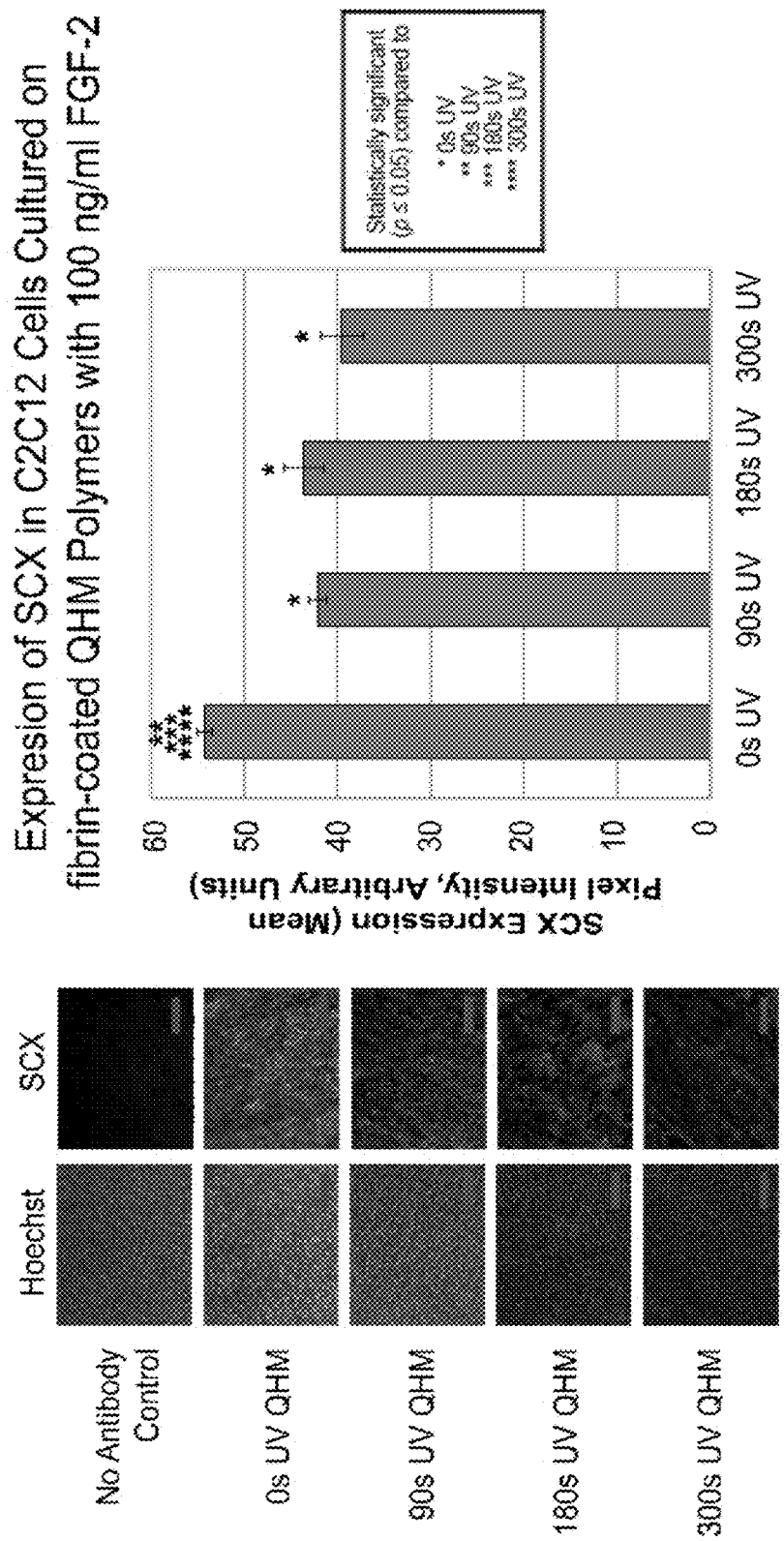
FIG. 18 shows effect of FGF-2 on C2C12 tenocyte differentiation on QHM polymers after 3 days culture. FGF-2-treated C2C12 cells showed increased SCX expression on fibrin-coated 0 s UV QHM polymer (n=9) relative to fibrin-coated 90 s, 180 s and 300 s UV QHM polymers. Scale bars 200 µm. Error bars indicate standard error of mean. Statistical significance (p≤0.05) as indicated.

In order to promote bone-tendon healing, the effect of biomechanical cues (via substrate stiffness) on musculoskeletal differentiation was determined. In recent years, substrate stiffness has been recognized as an important factor for controlling cell differentiation. Studies on cellular biomechanics showed that compliant substrates promoted neural and myogenic differentiation whereas stiffer substrates promoted osteoblast differentiation[37]. Additional studies demonstrated that such mechanosensitive differentiation occurred independently of substrate porosity and protein tethering[137] but was influenced by their past-exposure to substrates stiffness[138]. In this study, QHM polymer stiffness affected osteoblast and tenocyte differentiation. In the presence of BMP-2, C2C12 cells cultured on stiffer QHM polymers for 4 days exhibited increased ALP activity (FIGS. 9A-9D). In the presence of BMP-2 and blebbistatin (which interferes with cellular mechanosensing)[37], ALP activity was inhibited slightly but the overall trend remained (FIGS. 9A-9D). The phenomenon of increased ALP activity on stiffer substrates was unlikely to be related to differences in QHM polymer porosity (FIGS. 10A-10B), QHM polymer surface roughness (FIG. 11), musculoskeletal progenitor cell attachment, viability and proliferation (FIGS. 12A-12B and FIGS. 13A-13B) or leaching of unreacted QHM polymer components or degradation products (FIGS. 9A-9D and FIGS. 15A-15B). Also, the magnitude of blebbistatin-induced ALP inhibition was determined by calculating the ratio of ALP activity between 0.3% DMSO control and its corresponding 25 µM blebbistain-treated group. These results indicated that a larger magnitude of C2C12 ALP inhibition was observed on less stiff QHM polymers (FIGS. 9A-9D). The magnitude of this inhibition decreased with increased culture duration (FIGS. 9A-9D) and was attributed to increased administration of BMP-2 (FIGS. 15A-15B). Interestingly, although expression of other osteoblast markers RUNX2 and OCN were detected at 4 days, it was not different among QHM polymers (FIGS. 14A-14B). Long-term culture of C2C12 cells on QHM polymer under continuous osteogenic conditions eventually resulted in mineralization (FIG. 16). In the presence of FGF-2, C2C12 cells cultured on stiffer QHM polymers for 3 days exhibited decreased SCX expression (FIG. 18). Similar results were observed for both osteoblast and tenocyte differentiation on mechanically-graded QHM polymers with 0 s UV and 300 s UV regions (FIGS. 14A-14B). Together, these data suggest that QHM polymers provided biomechanical cues (via substrate stiffness) that spatially controlled bone and tendon cell differentiation.

Figure 21:
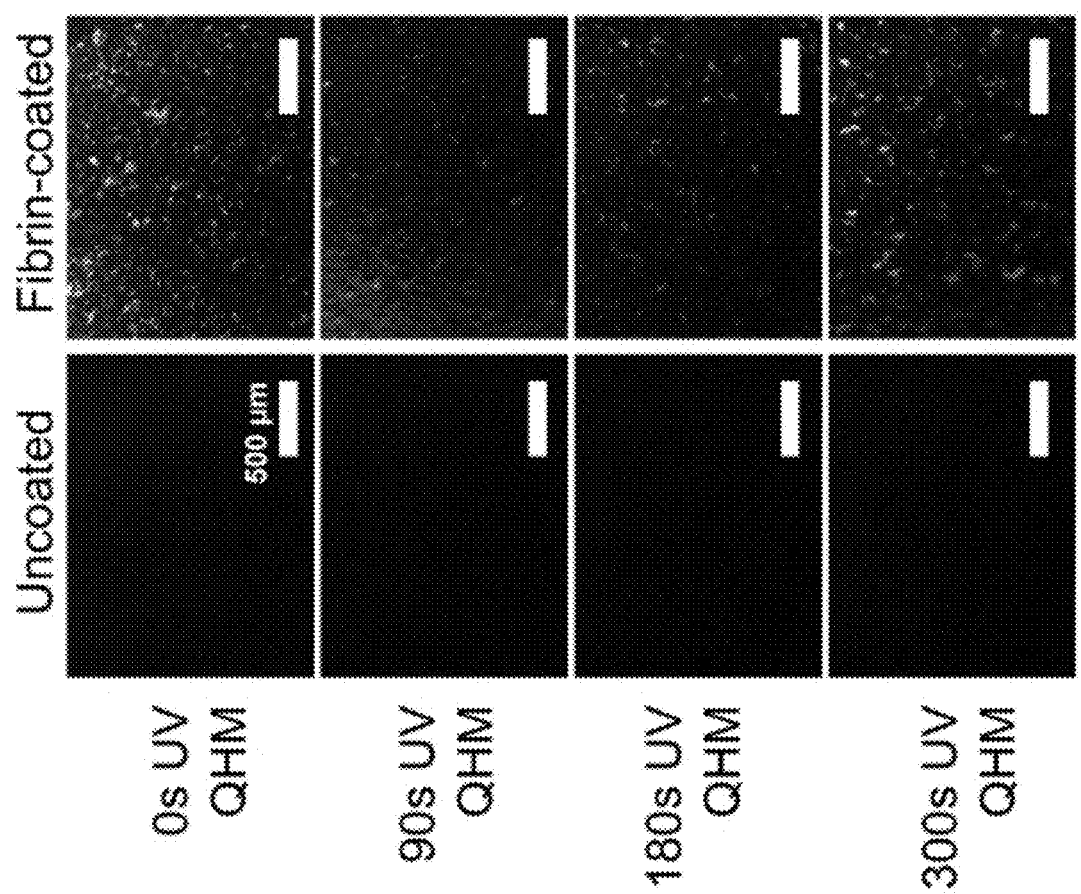
FIG. 21 shows effect of fibrin-coating on QHM polymers. Representative fluorescence images of uncoated and Alexa Fluor®-labeled fibrin-coated QHM polymers (n=3). Scale bars 500 µm.
Figure 22A:
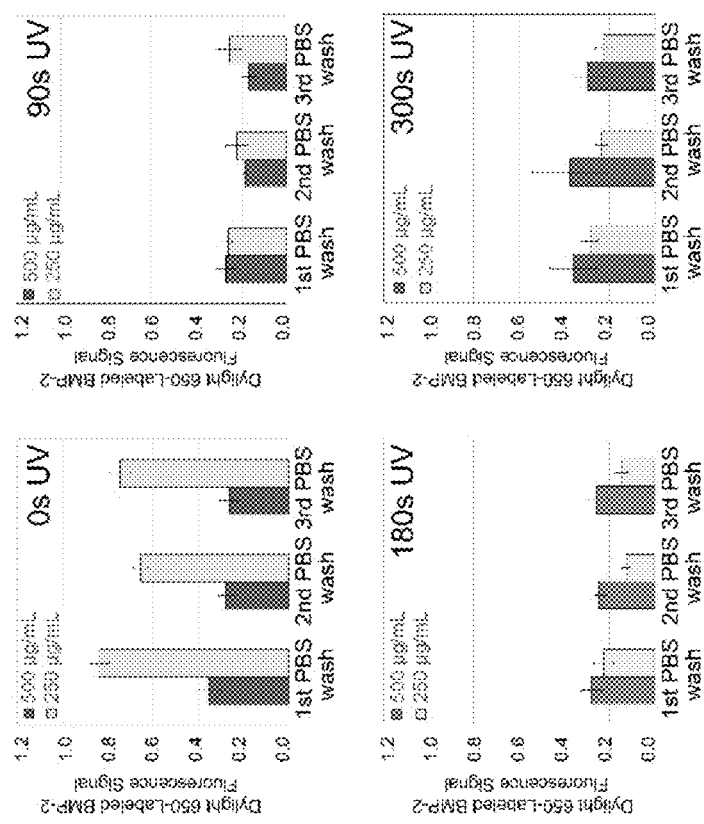
FIGS. 22A and 22B shows BMP-2 and FGF-2 immobilization on fibrin-coated QHM polymers.
Figure 22A:
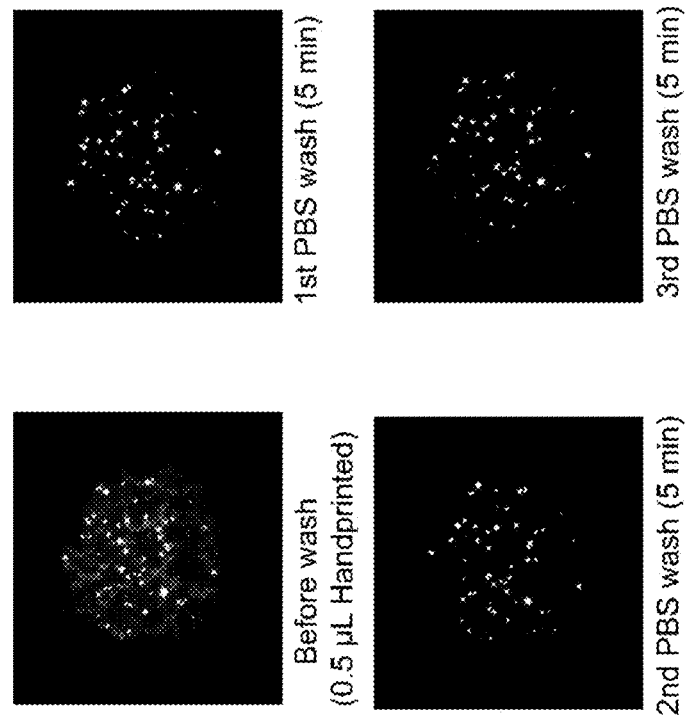
Figure 22B:
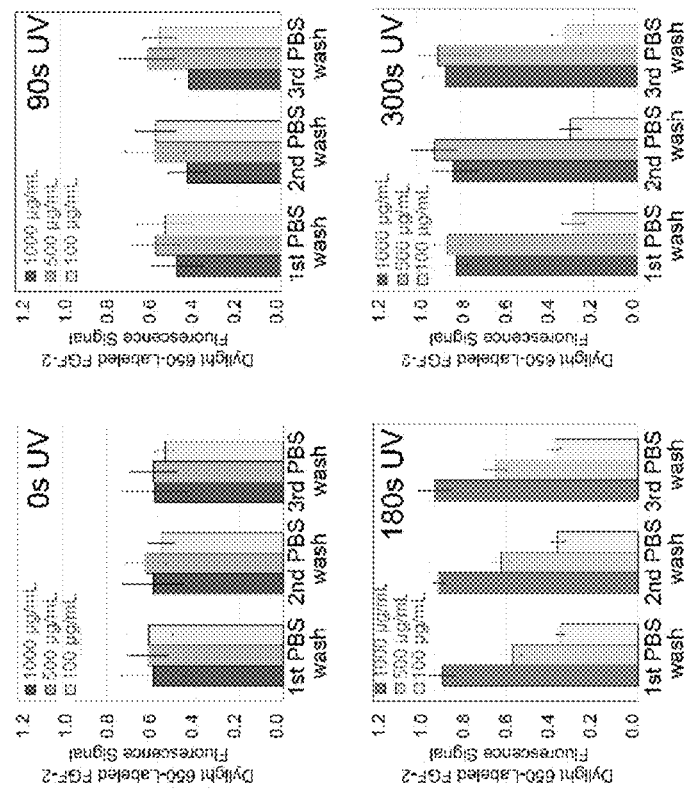
Figure 22B:
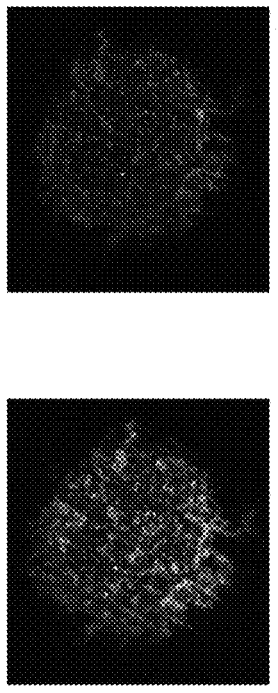
Figure 22B:
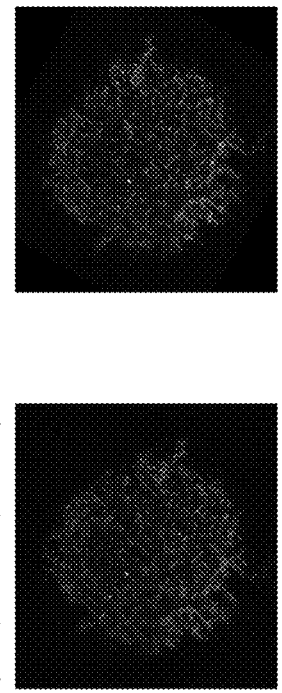
Figure 22B:
Figure 23:
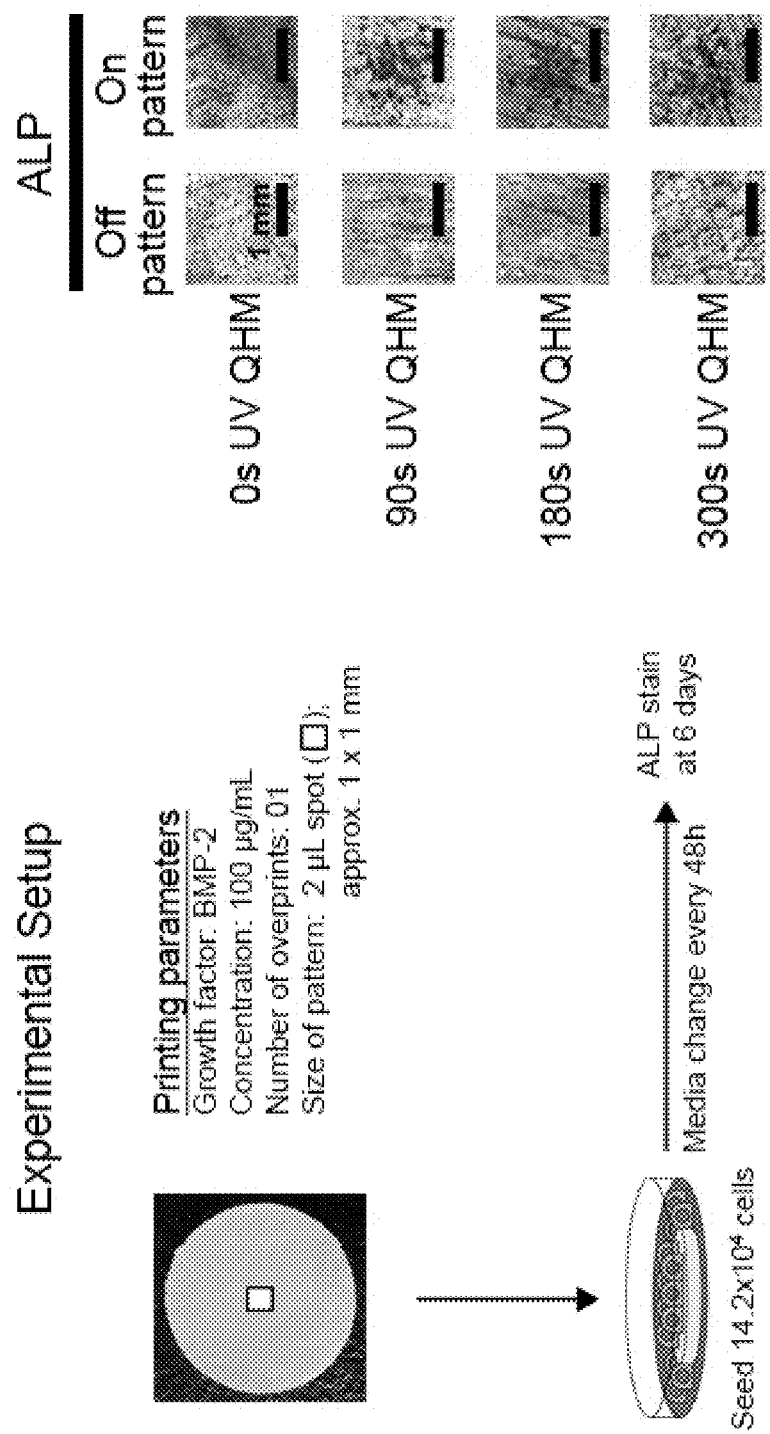
FIG. 23 shows effect of BMP-2 biopatterning on spatial control of C3H10T1/2 osteoblast differentiation after 6 days culture. The experimental setup and representative ALP-stained images are shown (n=1). ALP-positive regions stained blue. Scale bars 1 mm.
Figure 24:
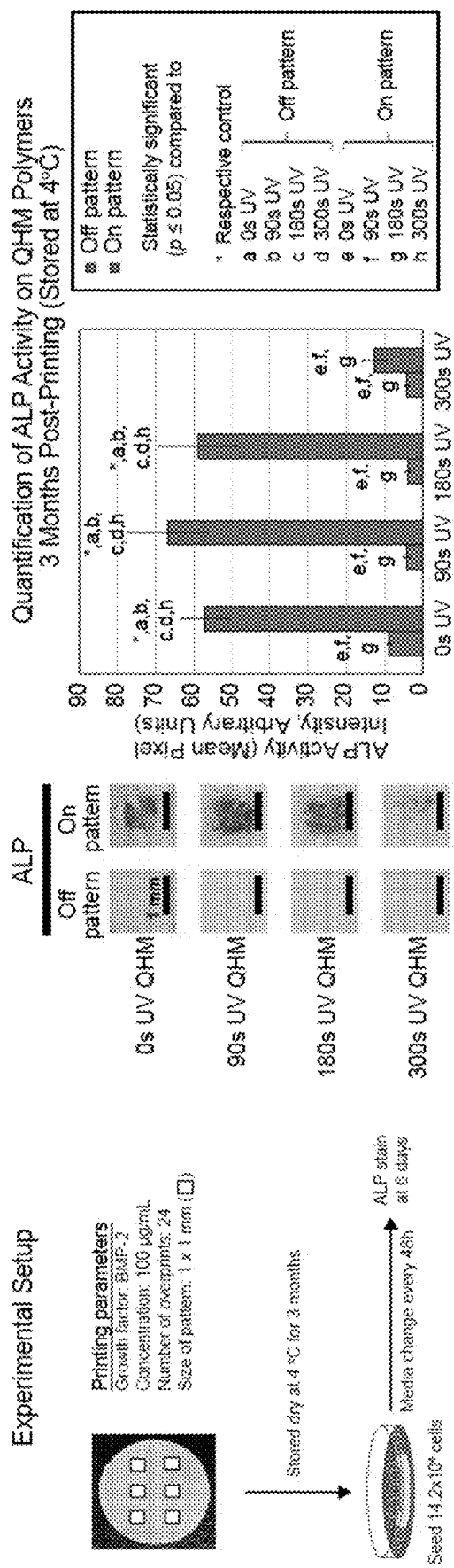
FIG. 24 shows effect of BMP-2 biopatterning on spatial control of C2C12 osteoblast differentiation 3 months post-printing and after 6 days culture. The experimental setup, representative ALP-stained images and quantification are shown (n=6). ALP-positive regions stained blue. Scale bars 1 mm. Error bars indicate standard error of mean. Statistical significance (p≤0.05) as indicated.

In order to promote bone-tendon healing, the effect of biochemical cues (via growth factor-biopatterning) on musculoskeletal differentiation was determined. Growth factor-biopatterning mimics growth factor-ECM interactions[139] by utilizing a custom inkjet printer to immobilize biochemical cues at physiologically-relevant concentrations to spatially direct multi-tissue phenotypes[18,19,29-32,48-50]. This approach is distinct from traditional drug delivery methods, which are dependent on scaffold/carrier degradation and subsequent drug release kinetics. In traditional drug delivery, there is limited spatial control of cell behavior because cell signaling is reliant on diffusion. In contrast, growth factors can be biopatterned at high resolution (approximately 75 μm)[48] on an ECM-coated surface (FIG. 20 and FIG. 21), which is capable of sequestering heparin-binding growth factors such as BMP-2 and FGF-2 (FIGS. 22A-22B). As such, only cells that come into contact with the growth factor-immobilized surface will be activated, achieving high spatial control of cell behavior in vitro[18,19,29,30,48-50] and in vivo (for at least 4 weeks)[31,32]. Furthermore, growth factor immobilization achieves persistent cell signaling, allowing lower growth factor doses to achieve the same effect when compared to freely-diffusing growth factor in solution[139]. Thus, growth factor-biopatterning utilizes physiologically-relevant[140], low picogram to nanogram doses of growth factors[18,19,29-32,48-50] to control cell behavior, while being both economical and achieving minimal off-target effects. In this study, in vitro biopatterning of BMP-2 on fibrin-coated QHM polymers spatially controlled C2C12 and C3H10T1/2 osteoblast differentiation (FIGS. 19A-19E, FIG. 23, and FIG. 24) while in vitro biopatterning of FGF-2 spatially controlled C2C12 tenocyte differentiation (FIGS. 19A-19E). The relative increase in C2C12 and C3H10T1/2 ALP activity as well as decrease in C2C12 SCX expression on stiffer QHM polymers indicated that substrate stiffness can affect musculoskeletal cell differentiation on growth factor-biopatterned surfaces (FIGS. 19A-19E and FIG. 23). Subcutaneous implantation of growth factor-biopatterned, fibrin-coated QHM polymers resulted in the ectopic formation of bone- and tendon-like tissues (FIGS. 19A-19E and FIG. 25). Formation of bone-like tissue on BMP-2 patterns was demonstrated by the presence of cells that expressed the osteoclast marker TRAP as well as collagen-rich, bone marrow-containing structures. Formation of tendon-like tissue on FGF-2 and GDF-7 patterns was demonstrated by the presence of high SCX-expressing cells as well as wavy, crimped and birefringent collagen fibers. In addition, the majority of biopatterned QHM polymers retained their bioactivity 3 months post-printing (FIG. 24). Together, these results demonstrated that growth factor-biopatterning of QHM polymers provided biochemical cues (via growth factor-biopatterning) to spatially control bone and tendon cell differentiation.

In order to facilitate clinical translation, QHM polymers must possess favorable physicochemical characteristics including physical features for musculoskeletal attachment. During surgical repair, orthopaedic devices known as suture anchors are usually affixed to bone. These suture anchors typically possess physical features such as suture eyelets that allow a suture to be threaded through, facilitating repair with either suture alone or a combination of suture and tendon graft. Although this approach facilitates the re-approximation of torn tendon back to its original anatomical location[7], it inevitably disrupts the continuity of the bone-tendon unit and introduces potential modes of failure including suture breakage at the eyelet[141] and loosening of suture eyelets as a result of degradation[142]. By utilizing the UV-crosslinking properties of the QHM polymer to fabricate a hybrid suture anchor-tendon graft, the continuity of the bone-tendon unit may be better re-established. In addition, UV-crosslinking enables patterning of QHM polymer at physiologically-relevant length scales (FIG. 27). The bone-like portion of this hybrid suture anchor-tendon graft can be affixed to humeral bone via screw threads while sutures can be applied at the tendon-like portion (FIGS. 26A-26H). This repurposes the suture anchor, first implemented in 1905[143] as means of anchoring suture to bone into a device that attaches to bone whilst providing a tendon-like graft for repair. Further studies are required to determine whether such a device may be used in an interpositional fashion (which only bridges the tear gap) or augmented fashion (which bridges the tear gap as well as overlaps with remaining tendon). While an interpositional repair potentially restores tendon anatomy and biomechanics with potentially little-to-no stress-shielding effects, an augmented repair would provide additional tensile strength and minimize suture tearing through the remaining tendon. An augmented repair may be particularly advantageous for clinical scenarios where tear chronicity results in degenerated tendon at the tear margins, making it impractical to perform an interpositional repair[7]. Together, these results showed that QHM polymers could be fabricated as a hybrid suture anchor-tendon graft.

In order to facilitate clinical translation, QHM polymers must possess favorable physicochemical characteristics including slow degradation and minimal cytotoxicity. Although the optimal degradation rate for injured rotator cuffs will vary depending on the patient, injury severity and chronicity, a biomaterial that exhibits slow degradation is desirable. This is because rotator cuff injuries often heal slowly and may require several years of clinical follow up[7]. As such, slow degradation is vital for maintaining graft integrity, preventing destabilization of its graded interface and avoiding disruption of spatially-patterned tissue phenotypes, which contribute towards the graft's ability to heal and sustain physiologically-relevant loading. For example, polyglactin was used to fabricate one of three stratified layers in a multi-phased graft but the polyglactin layer degraded completely within 8 weeks, reducing compressive strength by 50%[82]. Similar scenarios have been observed clinically whereby suture anchors made of rapidly degrading copolymers resulted in the suture becoming a loose body[28] or were suspected of causing suture anchor migration[144]. Slow degradation also minimizes toxicity effects and adverse tissue responses. For example, adverse biological reactions such as osteolysis, although rare, have been observed more frequently in fast-degrading polyglycolide-based suture anchors[145] compared to slow-degrading poly-L-lactic acid-based suture anchors[146]. Our degradation studies showed that QHM polymers degraded slowly under aqueous, acidic, alkaline and oxidizing conditions (FIGS. 26A-26H). These conditions were selected to approximate normal physiological conditions, chronic wound healing conditions (where either acidic or alkaline pH persist)[147] as well as foreign body reaction to biomaterials (where reactive oxygen species are generated in a low pH environment by macrophages and foreign body giant cells)[148]. The slow degradation of QHM polymers was likely attributed to its high content of carbamate groups, which are slow to hydrolyze[43,90]. In addition, C2C12 and C3H10T1/2 cells cultured on QHM polymers were viable (FIGS. 12A-12B and FIGS. 13A-13B) while C2C12 proliferation and muscle differentiation were not affected by QHM degradation products (FIGS. 26A-26H). Furthermore, QHM polymers implanted subcutaneously in mice for 2 weeks did not induce an overly exuberant inflammatory response and growth factor-biopatterned surfaces resulted in the formation of ectopic bone- and tendon-like tissues (FIGS. 19A-19E), which is indicative of biocompatability. Together, these results showed that QHM polymers exhibited slow degradation profiles with little-to-no cytotoxicity.

In summary, the present invention is directed to a UV-crosslinkable QHM polymer that 1) can be fabricated into a mechanically-graded material with bone- and tendon-like properties to sustain physiological loading and minimize stress concentrations, 2) can spatially control musculoskeletal differentiation via substrate stiffness and growth factor-biopatterning and 3) can undergo slow degradation with minimal cytotoxicity in addition to being fashioned as a continuous bone-tendon graft. Future work will focus on evaluating QHM polymer performance using appropriate animal models including acute and chronic rat rotator cuff injuries. Thus, this material is anticipated to be useful for studying musculoskeletal biology and repairing injured bone-tendon tissues.

Results

Fabrication of UV-Crosslinkable QHM Polymers

Figure 1A:
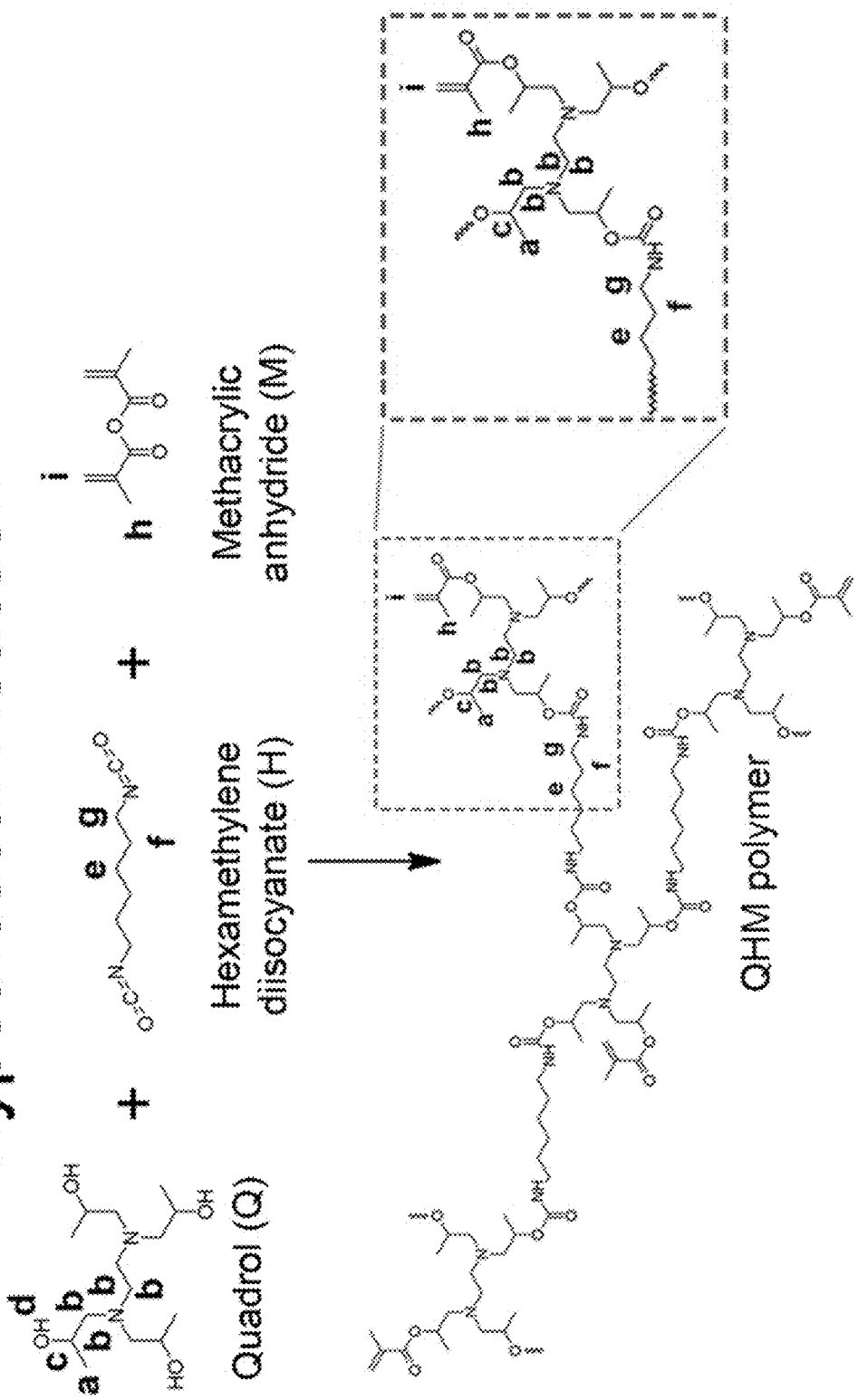
FIGS. 1A-1C show scheme for QHM (Quadrol-Hexamethylene diisocyanate-Methacrylic anhydride) polymer synthesis.
Figure 1C:
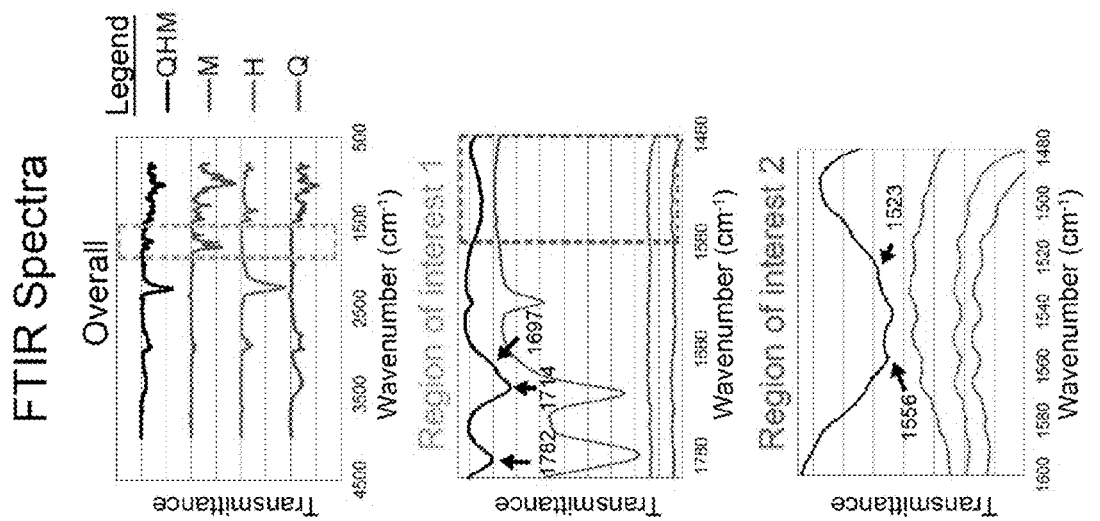
Figure 1B:
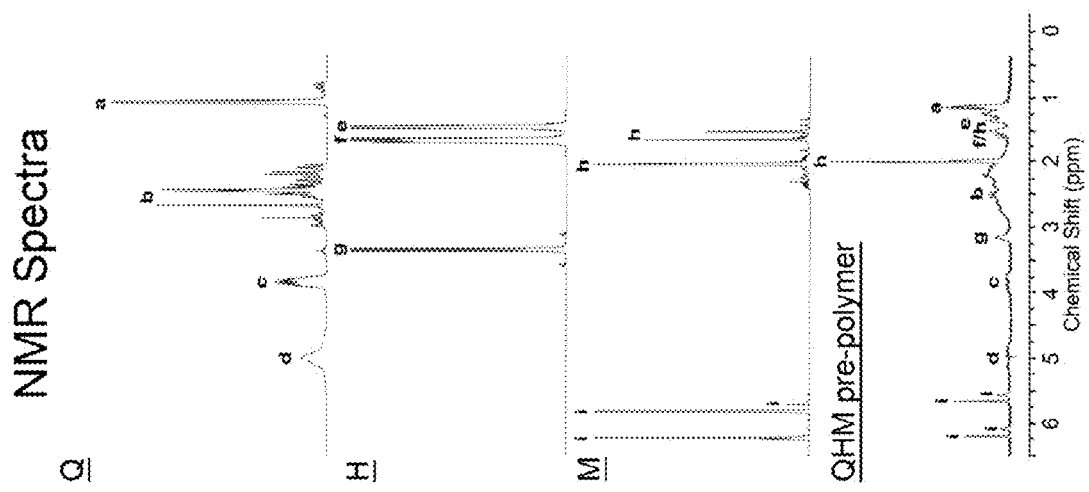
Figure 2A:
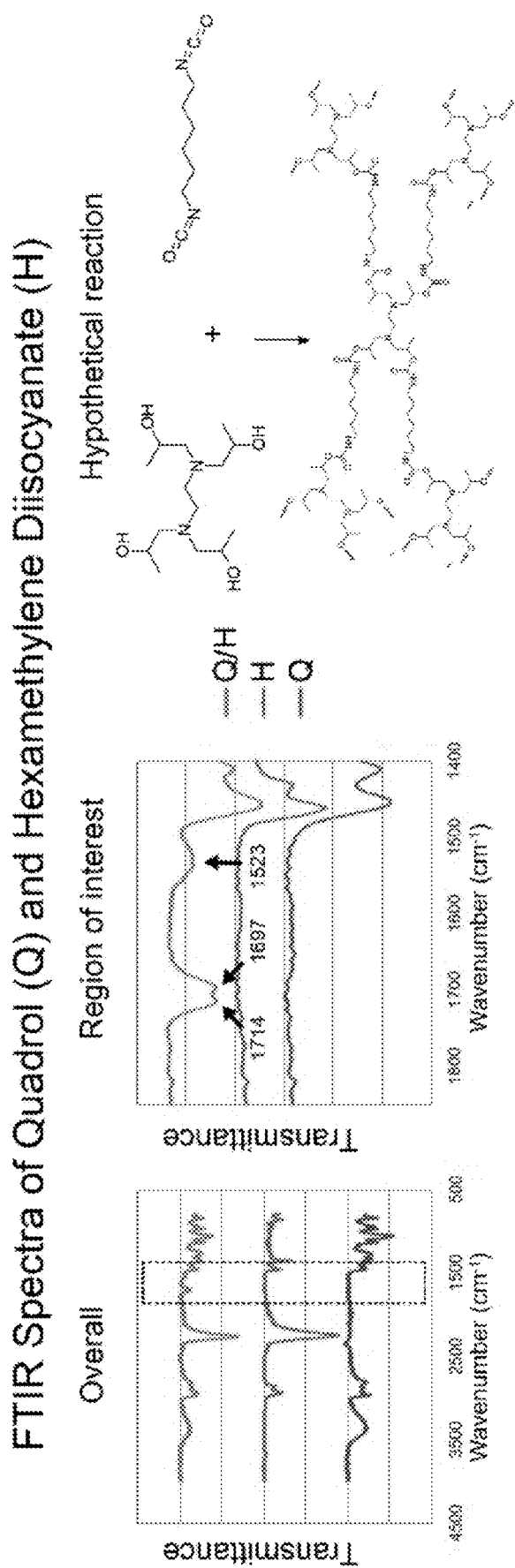
FIGS. 2A-2D show FTIR-ATR spectra of QHM pre-polymer components and $^1$H-NMR spectra of UV-exposed QHM polymers.
Figure 2B:
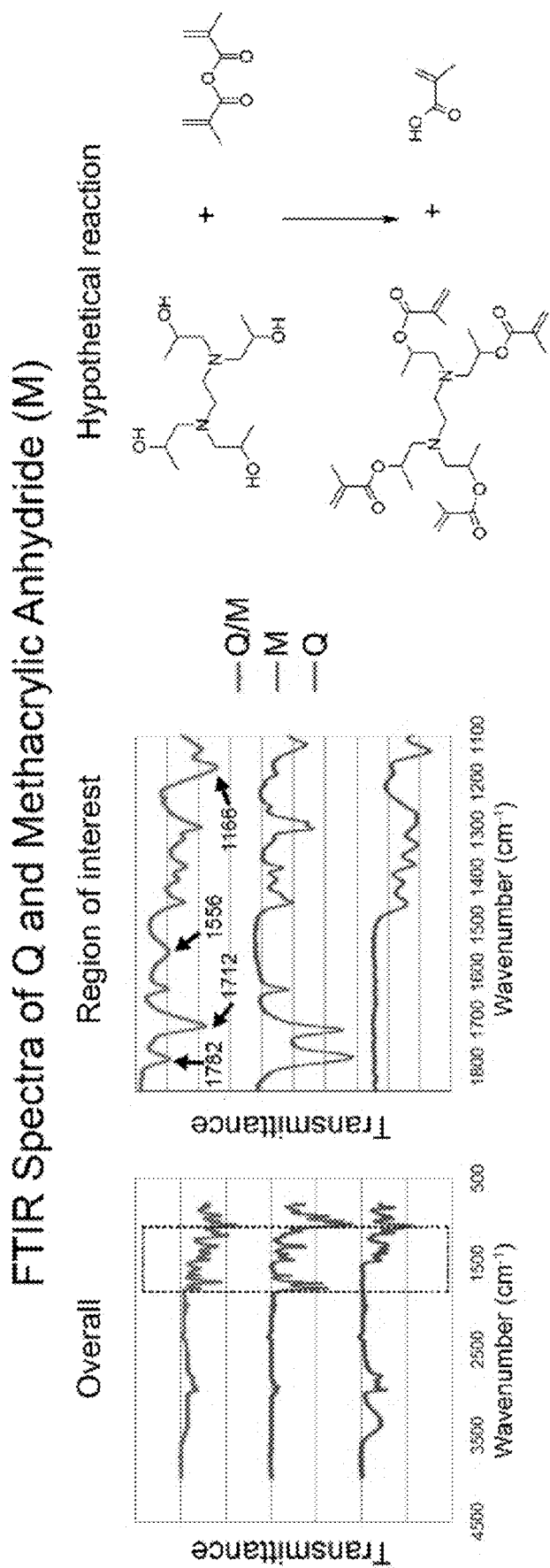
Figure 2C:
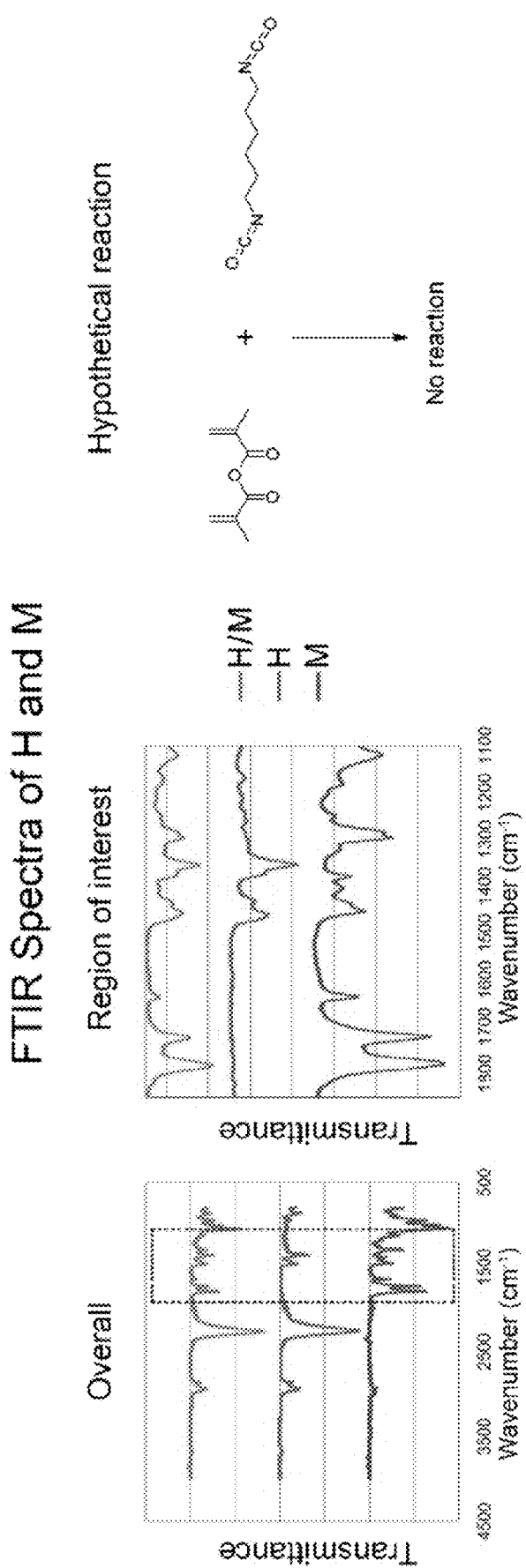
Figure 2D:
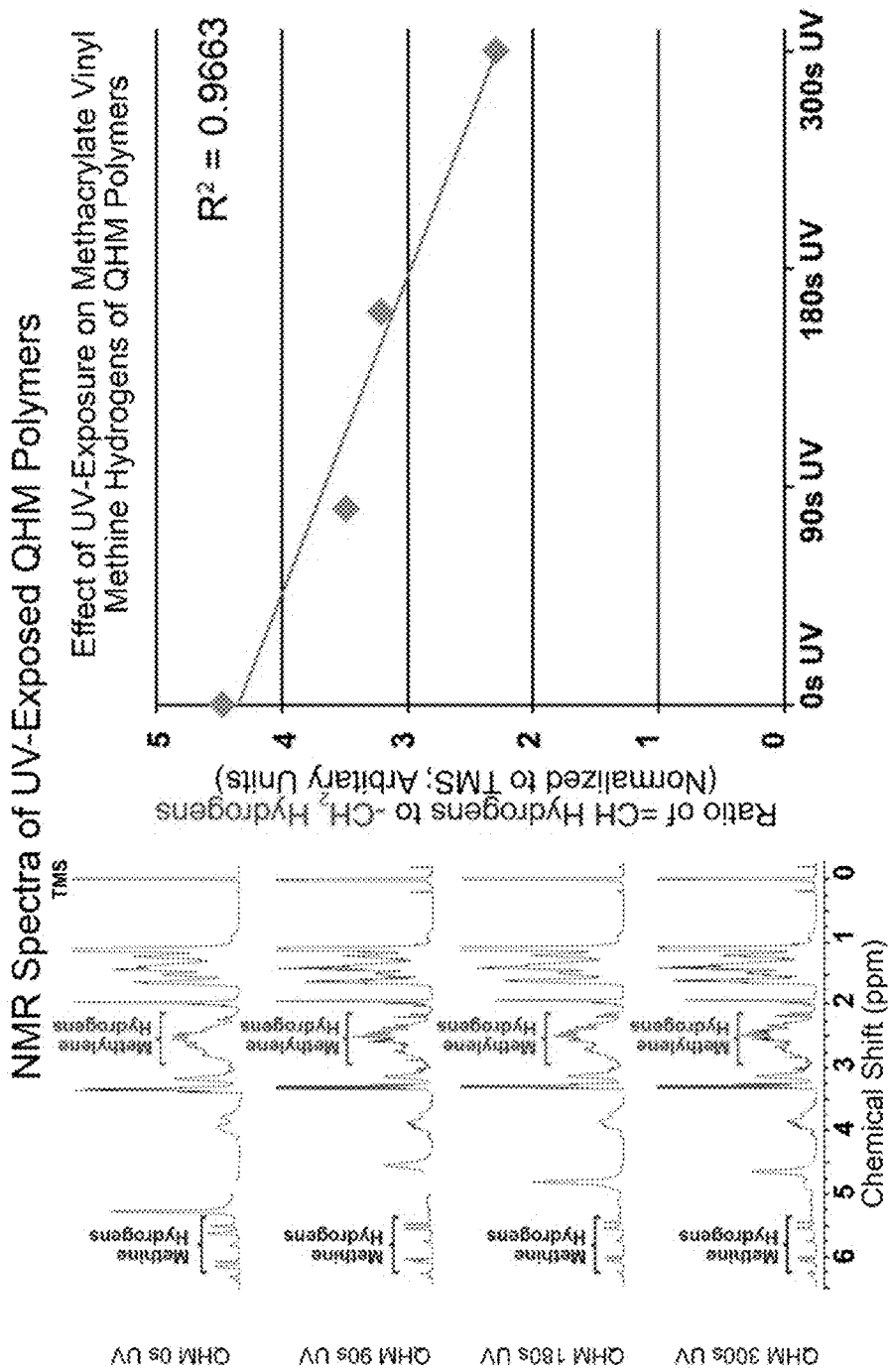

The fabrication of QHM polymers was monitored by $^1$H-NMR and FTIR-ATR spectroscopy (FIGS. 1A-1C). QHM polymers were synthesized from Q, H and M (FIG. 1A). $^1$H-NMR spectra of Q/H/M showed characteristic peaks observed in individual $^1$H-NMR spectra of Q, H and M (FIG. 1B and Table 1)[33,34]. FTIR-ATR spectra of Q/H, Q/M and H/M pre-polymers indicated chemical reactions between Q and H (FIG. 2A) as well as Q and M (FIG. 2B) but not between H and M (FIG. 2C). FTIR-ATR spectra of Q/H/M pre-polymer indicated reactions between the hydroxyl groups of Q and isocyanate groups of H to form carbamate groups as well as the hydroxyl groups of Q and the anhydride carbonyl groups of M to form ester groups (FIG. 1C and Table 2)[33-35]. $^1$H-NMR spectra of QHM polymers indicated increased crosslinking with longer UV-exposure (FIG. 2D). Together, these data demonstrated the presence of polyurethane carbamate groups, methacrylation and UV-crosslinking during polymer synthesis.

TABLE 1

$^1$H-NMR peak assignments for QHM components and QHM pre-polymer.

| Component | Peak (ppm) | Proton assignment(s) | Reference(s) |
|---|---|---|---|
| Q | 1.04 | Methyl ($CH_3$) | Silverstein et al.[34] |
|   | 2.00-2.95 | Methylene ($CH_2$) | Silverstein et al.[34] |
|   | 3.81 | Methine (CH) | Silverstein et al.[34] |
|   | 5.00 | Hydroxyl (OH) | Silverstein et al.[34] |
| H | 1.42, 1.62 and 3.32 | Methylene ($CH_2$) | Mercado-Pagan et al.[33] and Silverstein et al.[34] |
| M | 1.63, 2.00 | Terminal vinyl ($=CH_2$) | Mercado-Pagan et al.[33] and Silverstein et al.[34] |
|   | 5.83, 6.24 | Methyl ($CH_3$) | Mercado-Pagan et al.[33] and Silverstein et al.[34] |
| Q/H/M | 1.04 | Methyl ($CH_3$) | Silverstein et al.[34] |
|   | 1.63, 2.00 | Terminal vinyl ($=CH_2$) | Mercado-Pagan et al.[33] and Silverstein et al.[34] |
|   | 1.42, 1.62, 2.00-2.95 and 3.32 | Methylene ($CH_2$) | Mercado-Pagan et al.[33] and Silverstein et al.[34] |
|   | 3.81 | Methine (CH) | Silverstein et al.[34] |
|   | 5.00 | Hydroxyl (OH) | Silverstein et al.[34] |

TABLE 2

FTIR-ATR Peak Assignments for QHM pre-polymer.

| Functional group | Peak ($cm^{-1}$) | Assigned to | Reference(s) |
|---|---|---|---|
| Carbamate | 1523 $cm^{-1}$ | Bending vibrations of carbamate amine (N—H) | Silverstein et al.[34] |
|   | 1697 $cm^{-1}$ | Stretching vibrations of carbamate carbonyl (C=O) | Silverstein et al.[34] |
| Ester | 1556 $cm^{-1}$ | Stretching vibrations of intermediate carboxylate anions ($COO^-$) | Kim et al.[35], Mercado-Pagan et al.[33] and Silverstein et al.[34] |
|   | Peak intensity changes between 1714 $cm^{-1}$ and 1782 $cm^{-1}$ | Stretching vibrations of ester carbonyl (C=O) groups and stretching vibrations of carboxylic acid carbonyl (C=O) groups although anhydride and carbamate carbonyl (C=O) groups were also present | Kim et al.[35], Mercado-Pagan et al.[33] and Silverstein et al.[34] |

The chemical reactions among Q, H and M components of QHM pre-polymers (Q/H, Q/M, and H/M) as well as the effect of UV-exposure (0 s, 90 s, 180 s and 300 s UV) on QHM polymers were monitored by FTIR-ATR and $^1$H-NMR, respectively (FIGS. 2A-2D). The FTIR-ATR spectra of Q alone exhibited a broad peak around 3200-3500 $cm^{-1}$ which was attributed to stretching vibrations of hydroxyl (O—H) groups and hydrogen bonding (FIG. 2A)[34]. The FTIR-ATR spectra of H alone exhibited a sharp peak around 2200 $cm^{-1}$ which was attributed to stretching vibrations of isocyanate (N=C=O) groups (FIG. 2B)[33-35]. The FTIR-ATR spectra of M alone exhibited two sharp peaks around 1718 cm$^{-1}$ and 1780 cm$^{-1}$ which were attributed to stretching vibrations of anhydride carbonyl (C=O) groups (FIG. 2C)[33-35]. The FTIR-ATR spectra of Q/H were indicative of a reaction between the hydroxyl groups of Q and isocyanate groups of H to form carbamate groups. The spectra exhibited a peak change around 1523 cm$^{-1}$, which was attributed to bending vibrations of carbamate amine (N—H) groups as well as 2 peak changes around 1697 cm$^{-1}$ and 1714 cm$^{-1}$ which were attributed to stretching vibrations of carbamate carbonyl (C=O) groups (FIG. 2A)[34]. The FTIR-ATR spectra of Q/M were indicative of a reaction between the hydroxyl groups of Q and the anhydride carbonyl groups of M to form ester groups. The spectra exhibited a peak change around 1166 cm$^{-1}$, which was attributed to stretching vibrations of ester (C—O) groups as well as a peak change around 1556 cm$^{-1}$, which was attributed to stretching vibrations of carboxylate anion (COO$^-$) groups, an intermediate species formed during the reaction of carboxylic acid anhydrides and alcohols (FIG. 2B)[33-35]. Also, there was a relative change in peak intensity between 1712 cm$^{-1}$ and 1782 cm$^{-1}$, which were attributed to stretching vibrations of ester carbonyl (C=O) groups and stretching vibrations of carboxylic acid carbonyl (C=O) groups although anhydride carbonyl (C=O) groups were also present (FIG. 2B)[33-35]. The FTIR-ATR spectra of H/M did not indicate any chemical reaction between H and M as the spectra did not exhibit any peak changes (FIG. 2C). Integral intensity ratio analysis of $^1$H-NMR spectra for 0 s, 90 s, 180 s and 300 s UV-exposed QHM polymers indicated a relative decrease in the proton signals at 5-6 ppm compared to the proton signals at 2-3 ppm, which were attributed to methacrylated vinyl methine hydrogens and methylene hydrogens, respectively (FIG. 2D)[34]. Together, FTIR-ATR spectra indicated a reaction between Q and H as well as Q and M but not H and M while $^1$H-NMR spectra indicated increased crosslinking with increased UV-exposure.

Effect of UV-Exposure on the Mechanical Properties of QHM Polymers

The mechanical properties of QHM polymers was determined by tensile, compressive, creep and cyclic testing (FIGS. 3A-3D). FIG. 3 shows mechanical properties of QHM polymers. Pilot studies showed increased strength and elastic moduli with heat-curing (Data not shown). Thus, heat-cured QHM polymers were used for the remainder of this study.

QHM polymer exhibited phototunable tensile properties. The tensile strength and moduli of QHM polymers increased with longer UV-exposure, ranging from 12-74 MPa and 0.6-2.7 GPa, respectively, whereas those of QH polymer controls were largely unaltered (FIG. 3A, Tables 3, 4, and 5). Tensile strain at yield or failure of QHM polymers initially decreased with short (<90 s) UV-exposure and remained unchanged thereafter whereas QH polymer controls were largely unaltered (FIG. 3A and Tables 3 and 6). QHM polymers exhibited phototunable compressive properties. The compressive strength and moduli of QHM polymers increased with longer UV-exposure, ranging from 58-121 MPa and 1.5-3.0 GPa, respectively, whereas those of QH polymer controls were largely unaltered (FIG. 3B, Tables 7, 8 and 9). Strain at maximum compressive stress of QHM and QH polymers was largely unaltered with UV-exposure (FIG. 3B, Tables 7 and 10). Differential scanning calorimetry indicated that at 37° C., 0 s UV and 90 s UV QHM polymers exhibit compliance whereas 180 s UV and 300 s UV QHM polymers remain stiff (FIGS. 4A-4B).

To determine glass transition temperature of QHM polymers, differential scanning calorimetry (DSC) was performed. DSC heating curves showed that 0 s UV, 90 s UV, 180 s UV and 300 s UV QHM polymers possessed a glass transition temperature of 27.21° C., 33.99° C., 39.08° C. and 43.55° C., respectively (FIGS. 4A-4B). These data show that the glass transition temperature of QHM polymers increased with longer UV-exposure.

TABLE 3

Tensile properties (mean ± SEM) of QHM and QH polymers.

| Polymer | Tensile strength (MPa) Yield | Tensile strength (MPa) Failure | Tensile modulus (GPa) | Tensile strain at yield or failure (%) |
|---|---|---|---|---|
| 0 s UV QH | — | 70 ± 4.1 | 2.6 ± 0.13 | 4.8 ± 0.68 |
| 90 s UV QH | — | 71 ± 0.7 | 2.7 ± 0.05 | 4.0 ± 0.15 |
| 180 s UV QH | — | 71 ± 2.4 | 2.7 ± 0.06 | 3.9 ± 0.30 |
| 300 s UV QH | — | 69 ± 1.2 | 2.6 ± 0.08 | 4.2 ± 0.27 |
| 0 s UV QHM | 12 ± 0.7 | 20 ± 1.5 | 0.6 ± 0.03 | 6.5 ± 0.21 |
| 90 s UV QHM | — | 38 ± 3.0 | 1.7 ± 0.10 | 4.4 ± 0.17 |
| 180 s UV QHM | — | 65 ± 2.4 | 2.5 ± 0.07 | 4.2 ± 0.16 |
| 300 s UV QHM | — | 74 ± 1.5 | 2.7 ± 0.05 | 4.4 ± 0.10 |

TABLE 4

P values comparing tensile strength of QHM and QH polymers.

| Group | Group | P value |
|---|---|---|
| 0 s UV QHM polymer | 90 s UV QHM polymer | 0.000 |
| 0 s UV QHM polymer | 180 s UV QHM polymer | 0.000 |
| 0 s UV QHM polymer | 300 s UV QHM polymer | 0.000 |
| 90 s UV QHM polymer | 180 s UV QHM polymer | 0.000 |
| 90 s UV QHM polymer | 300 s UV QHM polymer | 0.000 |
| 180 s UV QHM polymer | 300 s UV QHM polymer | 0.133 |
| 0 s UV QH polymer | 90 s UV QH polymer | 1.000 |
| 0 s UV QH polymer | 180 s UV QH polymer | 1.000 |
| 0 s UV QH polymer | 300 s UV QH polymer | 1.000 |
| 90 s UV QH polymer | 180 s UV QH polymer | 1.000 |
| 90 s UV QH polymer | 300 s UV QH polymer | 1.000 |
| 180 s UV QH polymer | 300 s UV QH polymer | 1.000 |

TABLE 5

P values comparing tensile modulus of QHM and QH polymers.

| Group | Group | P value |
|---|---|---|
| 0 s UV QHM polymer | 90 s UV QHM polymer | 0.000 |
| 0 s UV QHM polymer | 180 s UV QHM polymer | 0.000 |
| 0 s UV QHM polymer | 300 s UV QHM polymer | 0.000 |
| 90 s UV QHM polymer | 180 s UV QHM polymer | 0.000 |
| 90 s UV QHM polymer | 300 s UV QHM polymer | 0.000 |
| 180 s UV QHM polymer | 300 s UV QHM polymer | 0.872 |
| 0 s UV QH polymer | 90 s UV QH polymer | 0.999 |
| 0 s UV QH polymer | 180 s UV QH polymer | 0.995 |
| 0 s UV QH polymer | 300 s UV QH polymer | 1.000 |
| 90 s UV QH polymer | 180 s UV QH polymer | 1.000 |
| 90 s UV QH polymer | 300 s UV QH polymer | 0.993 |
| 180 s UV QH polymer | 300 s UV QH polymer | 0.978 |

TABLE 6

P values comparing tensile strain at yield (0 s UV QHM polymer)
or failure (All other polymers) of QHM and QH polymers.

| Group | Group | P value |
|---|---|---|
| 0 s UV QHM polymer | 90 s UV QHM polymer | 0.001 |
| 0 s UV QHM polymer | 180 s UV QHM polymer | 0.000 |
| 0 s UV QHM polymer | 300 s UV QHM polymer | 0.001 |
| 90 s UV QHM polymer | 180 s UV QHM polymer | 1.000 |
| 90 s UV QHM polymer | 300 s UV QHM polymer | 1.000 |
| 180 s UV QHM polymer | 300 s UV QHM polymer | 1.000 |
| 0 s UV QH polymer | 90 s UV QH polymer | 0.706 |
| 0 s UV QH polymer | 180 s UV QH polymer | 0.482 |
| 0 s UV QH polymer | 300 s UV QH polymer | 0.824 |
| 90 s UV QH polymer | 180 s UV QH polymer | 1.000 |
| 90 s UV QH polymer | 300 s UV QH polymer | 1.000 |
| 180 s UV QH polymer | 300 s UV QH polymer | 0.999 |

TABLE 7

Compression properties (mean ± SEM) of QHM and QH polymers.

| Polymer | Compressive strength (MPa) | Compressive modulus (GPa) | Strain at maximum compressive stress (%) |
|---|---|---|---|
| 0 s UV QH | 105 ± 0.8 | 2.7 ± 0.02 | 5.5 ± 0.26 |
| 90 s UV QH | 118 ± 0.7 | 3.0 ± 0.02 | 6.5 ± 0.38 |
| 180 s UV QH | 106 ± 0.7 | 2.7 ± 0.04 | 6.2 ± 0.11 |
| 300 s UV QH | 108 ± 1.4 | 2.7 ± 0.03 | 6.7 ± 0.15 |
| 0 s UV QHM | 58 ± 4.0 | 1.5 ± 0.10 | 5.7 ± 0.23 |
| 90 s UV QHM | 82 ± 4.8 | 2.1 ± 0.11 | 5.8 ± 0.18 |
| 180 s UV QHM | 109 ± 2.4 | 2.8 ± 0.05 | 6.8 ± 0.25 |
| 300 s UV QHM | 121 ± 1.3 | 3.1 ± 0.04 | 6.0 ± 0.30 |

TABLE 8

P values comparing compressive strength
of QHM and QH polymers.

| Group | Group | P value |
|---|---|---|
| 0 s UV QHM polymer | 90 s UV QHM polymer | 0.053 |
| 0 s UV QHM polymer | 180 s UV QHM polymer | 0.000 |
| 0 s UV QHM polymer | 300 s UV QHM polymer | 0.000 |
| 90 s UV QHM polymer | 180 s UV QHM polymer | 0.017 |
| 90 s UV QHM polymer | 300 s UV QHM polymer | 0.003 |
| 180 s UV QHM polymer | 300 s UV QHM polymer | 0.021 |
| 0 s UV QH polymer | 90 s UV QH polymer | 0.000 |
| 0 s UV QH polymer | 180 s UV QH polymer | 0.950 |
| 0 s UV QH polymer | 300 s UV QH polymer | 0.670 |
| 90 s UV QH polymer | 180 s UV QH polymer | 0.000 |
| 90 s UV QH polymer | 300 s UV QH polymer | 0.003 |
| 180 s UV QH polymer | 300 s UV QH polymer | 0.944 |

TABLE 9

P values comparing compressive
modulus of QHM and QH polymers.

| Group | Group | P value |
|---|---|---|
| 0 s UV QHM polymer | 90 s UV QHM polymer | 0.000 |
| 0 s UV QHM polymer | 180 s UV QHM polymer | 0.000 |
| 0 s UV QHM polymer | 300 s UV QHM polymer | 0.000 |
| 90 s UV QHM polymer | 180 s UV QHM polymer | 0.000 |
| 90 s UV QHM polymer | 300 s UV QHM polymer | 0.000 |
| 180 s UV QHM polymer | 300 s UV QHM polymer | 0.029 |
| 0 s UV QH polymer | 90 s UV QH polymer | 0.047 |
| 0 s UV QH polymer | 180 s UV QH polymer | 0.994 |
| 0 s UV QH polymer | 300 s UV QH polymer | 1.000 |
| 90 s UV QH polymer | 180 s UV QH polymer | 0.240 |
| 90 s UV QH polymer | 300 s UV QH polymer | 0.074 |
| 180 s UV QH polymer | 300 s UV QH polymer | 0.999 |

TABLE 10

P values comparing compressive strain at
maximum stress for QHM and QH polymers.

| Group | Group | P value |
|---|---|---|
| 0 s UV QHM polymer | 90 s UV QHM polymer | 1.000 |
| 0 s UV QHM polymer | 180 s UV QHM polymer | 0.064 |
| 0 s UV QHM polymer | 300 s UV QHM polymer | 0.987 |
| 90 s UV QHM polymer | 180 s UV QHM polymer | 0.111 |
| 90 s UV QHM polymer | 300 s UV QHM polymer | 0.998 |
| 180 s UV QHM polymer | 300 s UV QHM polymer | 0.360 |
| 0 s UV QH polymer | 90 s UV QH polymer | 0.123 |
| 0 s UV QH polymer | 180 s UV QH polymer | 0.388 |
| 0 s UV QH polymer | 300 s UV QH polymer | 0.017 |
| 90 s UV QH polymer | 180 s UV QH polymer | 0.998 |
| 90 s UV QH polymer | 300 s UV QH polymer | 0.991 |
| 180 s UV QH polymer | 300 s UV QH polymer | 0.828 |

Creep and cyclic testing determined the robustness of 0 s UV QHM polymer. In static creep tensile tests, 0 s UV QHM polymers exhibited 1.7% strain following a 30 min hold at 3 MPa tensile stress and recovered 0.8% strain following a 10 min recovery period (FIG. 3C). Creep rate was 0.04% per min.

Figure 3D:
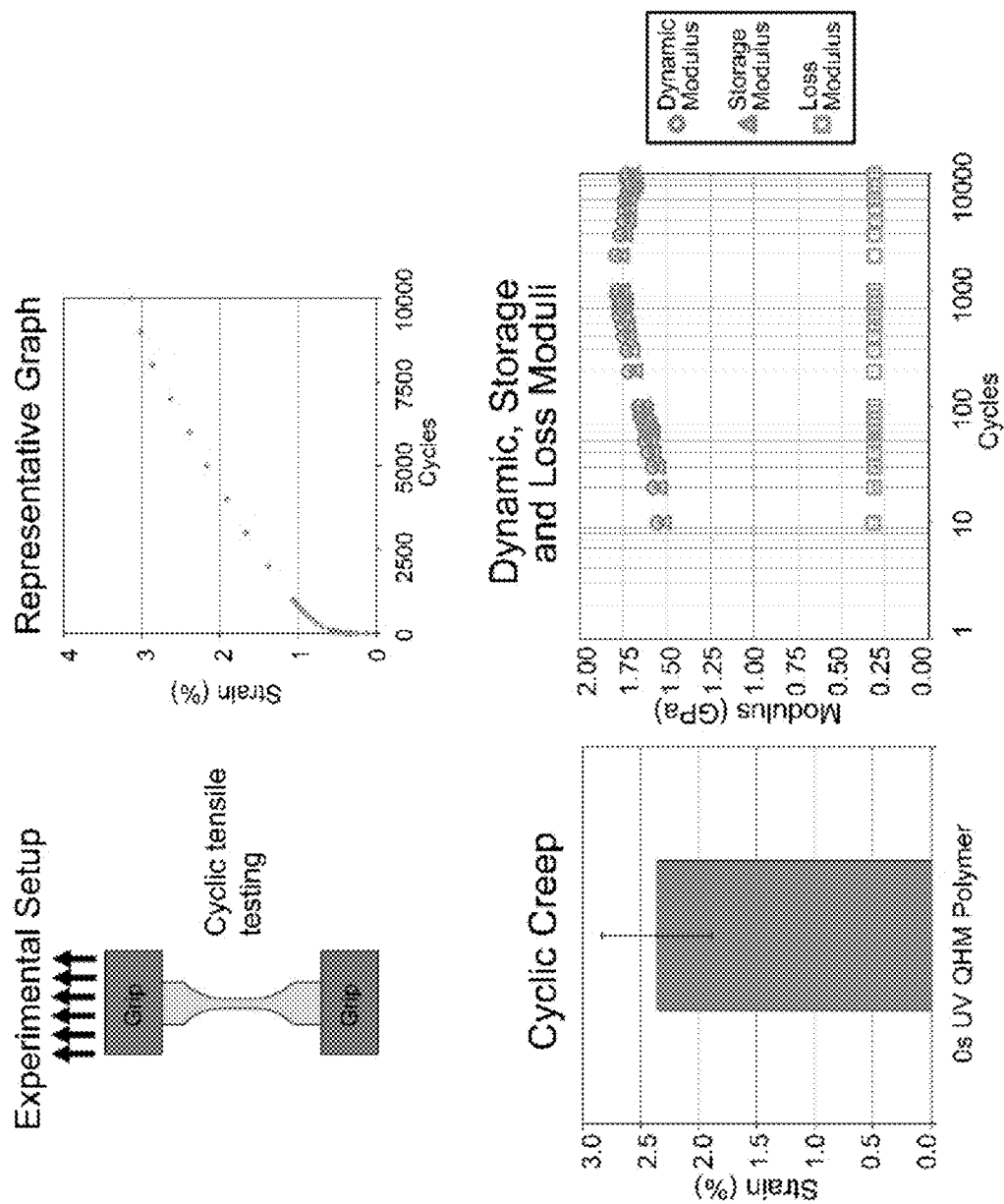

In cyclic tensile tests, 0 s UV QHM polymers exhibited 2.4% strain, consistent dynamic (1.5-1.8 GPa), storage (1.5-1.8 GPa) and loss moduli (0.3 GPa) as well as tan δ (0.18-0.20) during 10,000 loading cycles from 0.2 to 3 MPa tensile stress (FIG. 3D and Data not shown). Specimens reached steady state after approximately 4,000 cycles. A single specimen tested for 100,000 loading cycles exhibited 5.7% strain without failure and recovered following unloading (FIGS. 5A-5B).

To analyze long-term material fatigue, a single sample of 0 s UV QHM polymer was subjected to tensile loading between 0.2-3 MPa at 1 Hz for 100,000 cycles. 0 s UV QHM polymer exhibited primary stage creep between 0 and 4,000 cycles and secondary stage creep between 4,000 to 100,000 cycles with a steady-state creep rate of $5.1 \times 10^{-5}\%$ $s^{-1}$ (FIG. 5). Following testing, 0 s UV QHM polymer recovered its original length (Data not shown). Together, these data indicate that 0 s UV QHM polymer possesses robust tensile properties.

Thus, QHM polymers demonstrated phototunable mechanical properties including increased strength and modulus with longer UV-exposure while 0 s UV QHM polymer showed robust fatigue and recovery attributes.

Effect of Stiffness Gradients on Reducing Stress Concentrations in QHM Polymers

Figure 6A:
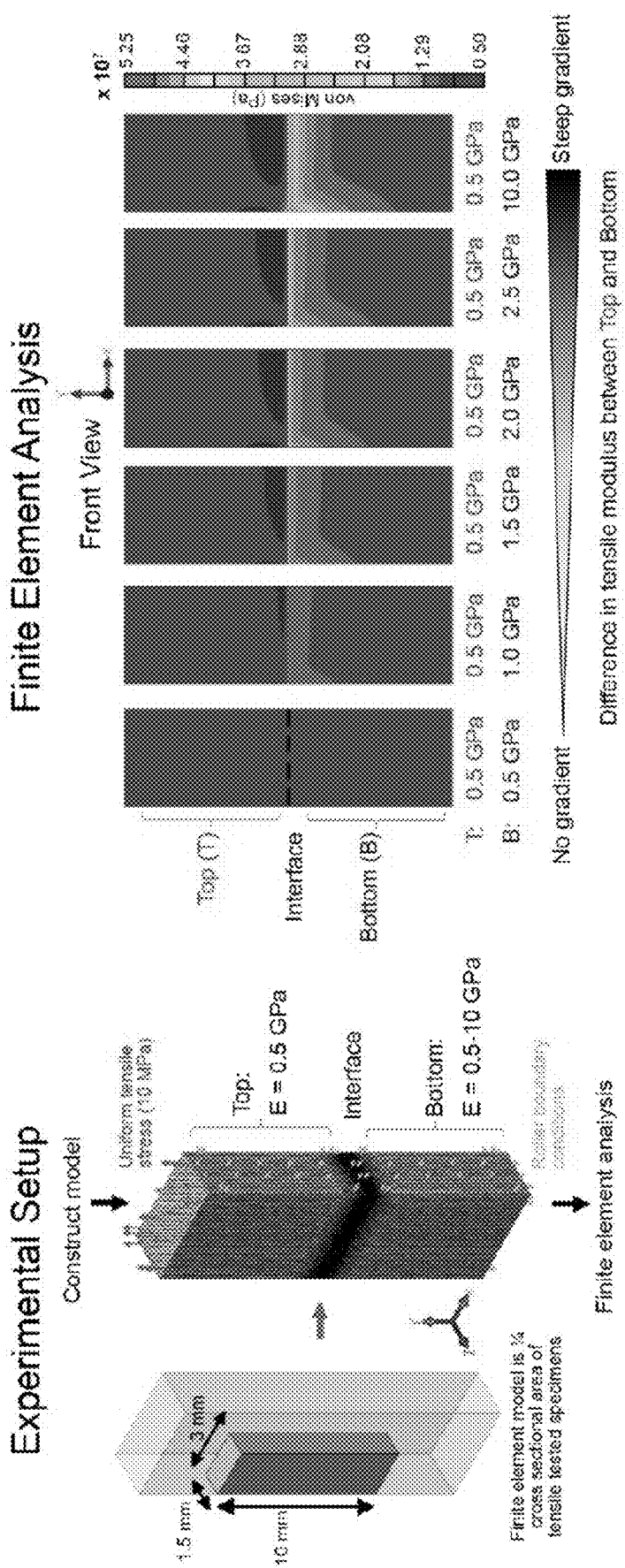
FIGS. 6A and 6B show effect of stiffness gradients on stress concentrations.
Figure 6B:
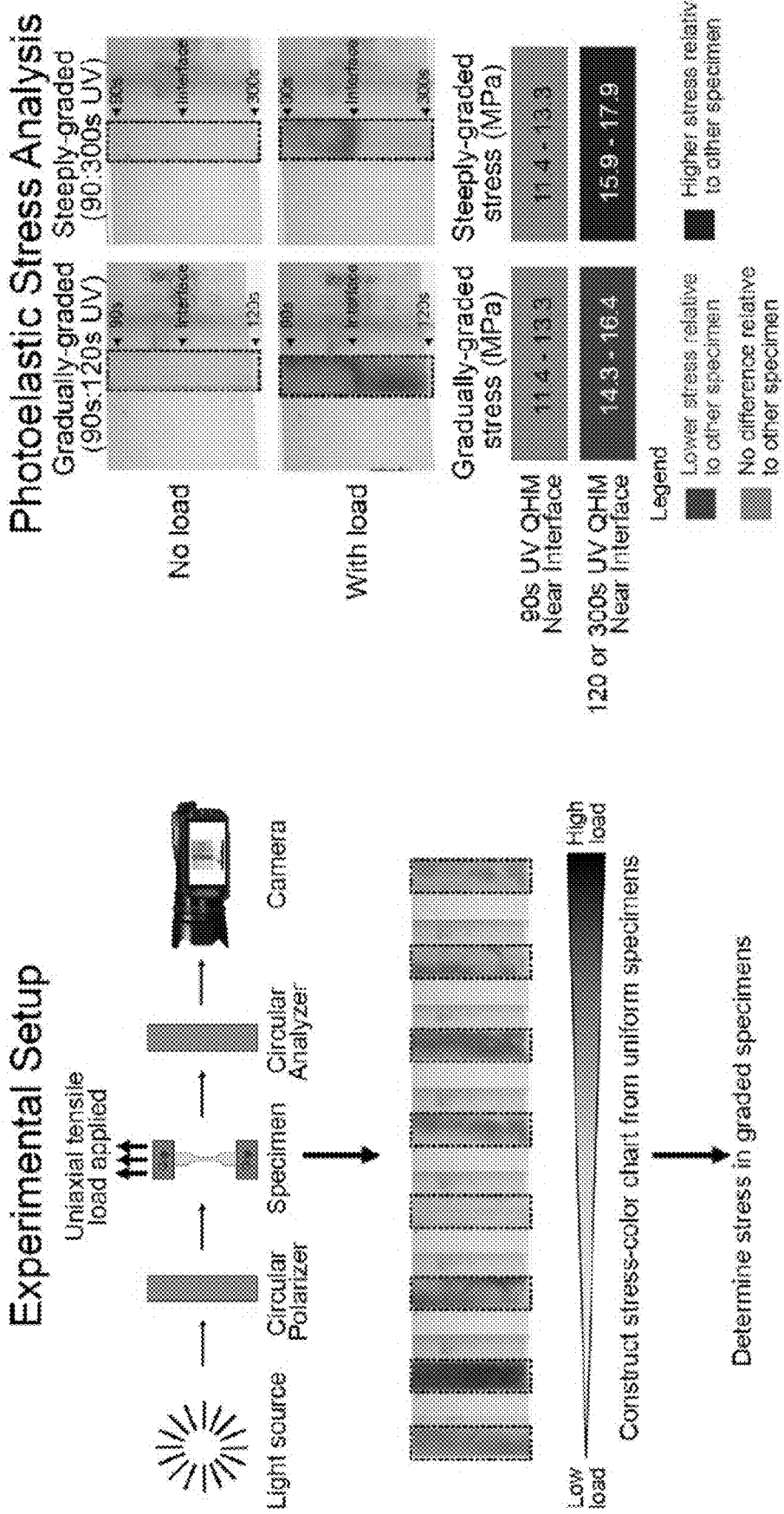
Figure 7:
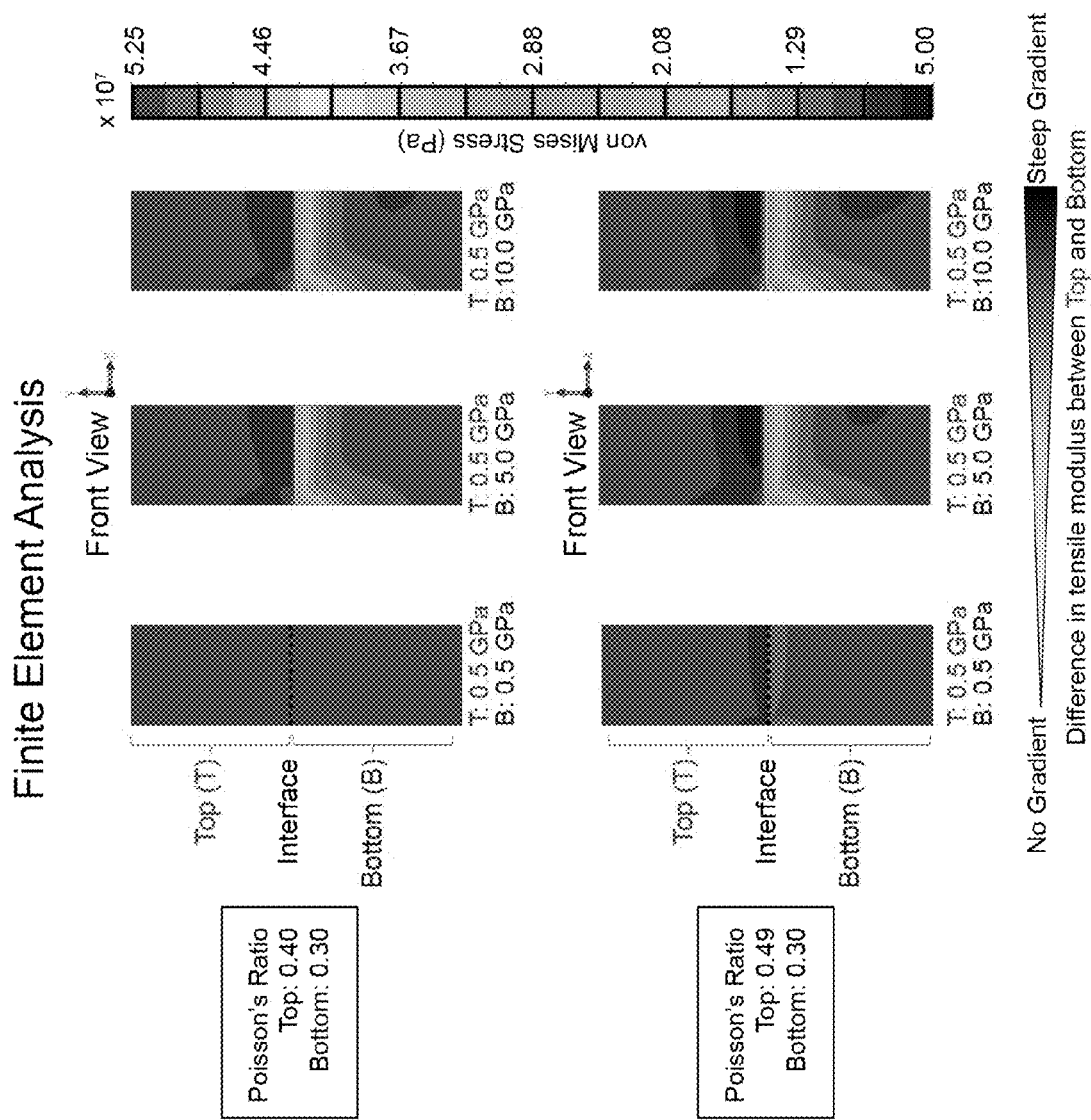
FIG. 7 shows the effect of varying Poisson's ratio on the formation of stress concentrations in uniform, gradually-graded and steeply-graded materials subjected to 10 MPa tensile stress. Finite element quarter models include uniform (left), gradually-graded (center) and steeply-graded (right) materials. The top row indicates materials with a Poisson's ratio of 0.40 for the top half and 0.30 for the bottom half of the model. The bottom row indicates materials with a Poisson's ratio of 0.49 for the top half and 0.30 for the bottom half of the model. Uniform tensile stress of 10 MPa was applied to top face of each model. Peak values of concentrated stress not presented in color plot.

The effect of stiffness gradients of QHM polymers on reducing stress concentrations was determined by finite element analysis (FEA) and photoelastic tensile testing (FIGS. 6A-6B). In FEA, the greatest stress concentration was observed in steeply-graded models at the intersection of the interface and free edge, with high stress levels primarily in the model's stiffer region near the interface and a centrally-located stress decrease in the model's compliant region near the interface (FIG. 6A). Varying Poisson's ratio yielded similar results, primarily affecting stress magnitude (FIG. 7).

To determine the effect of material properties on stress concentrations, finite element analysis (FEA) was performed on uniform, gradually-graded and steeply-graded quarter models with varying Poisson's ratios. When 10 MPa of uniform tensile stress was applied, an increase in von Mises stress was observed at the interface (FIG. 7). Peak stress was localized to a small region at the intersection of the interface and free edge. Although not shown in the color plots, this peak stress was 165 MPa for steeply-graded models with a Poisson's ratio of 0.40 (top half) and 0.30 (bottom half) whereas peak stress was 242 MPa for steeply-graded models with a Poisson's ratio of 0.49 (top half) and 0.30 (bottom half). In addition, high stress regions were primarily located in the bottom half (stiffer region) near the interface and a centrally located stress decrease was observed in the model's top half (compliant region) near the interface (FIG. 7). This stress redistribution was most prominent in steeply-graded models and intermediate in gradually-graded models (FIG. 7). Thus, steeply-graded models exhibited the largest stress increase compared to gradually-graded or uniform models, the magnitude of which varied with Poisson's ratio.

In photoelastic tensile testing (FIG. 8), gradually-graded specimens reduced stress concentrations relative to more steeply-graded specimens (FIG. 6B) corroborating FEA results. Gradually- and steeply-graded specimens subjected to tensile testing failed in the bulk material of the weaker top half but not at the interface (Data not shown). Thus, gradual-gradation reduced stress concentrations.

To determine stress within QHM polymers, a photoelastic tensile-color interference chart was constructed (FIG. 8). 0 s UV QHM polymer transitioned from clear at 0 N to dark brown at 100 N to light blue and yellow at 200 N to orange, purple and blue at 300 N, and green, yellow and purple at 400 N. 120 s UV QHM polymer transitioned from clear at 0 N to dark brown at 100 N to light blue at 200 N to yellow at 300 N, and purple and blue at 400 N. 300 s UV QHM polymer transitioned from clear at 0 N to light brown at 100 N to blue at 200 N to yellow and light blue at 300 N, and yellow and orange at 400 N. When normalized by the cross sectional area of QHM polymer, this color interference chart enabled photoelastic tensile stress analysis.

Effect of Young's Moduli on Osteoblast and Tenocyte Differentiation in QHM Polymers The effect of QHM polymer stiffness, which was varied by UV exposure) on osteoblast and tenocyte differentiation was determined by alkaline phosphatase (ALP) activity and Scleraxis (SCX) expression, respectively (FIGS. 9A-9D, FIGS. 10A-10B, FIG. 11, FIGS. 12A-12B, FIGS. 13A-13B, FIGS. 14A-14B, FIGS. 15A-15B, FIG. 16, FIG. 17 and FIG. 18). Bone morphogenetic protein-2 (BMP-2), fibroblast growth factor-2 (FGF-2) and blebbistatin were used to promote osteoblast differentiation, tenocyte differentiation and disrupt cellular mechanosensing, respectively (FIGS. 9A-9D and FIG. 17).

Figure 9A:
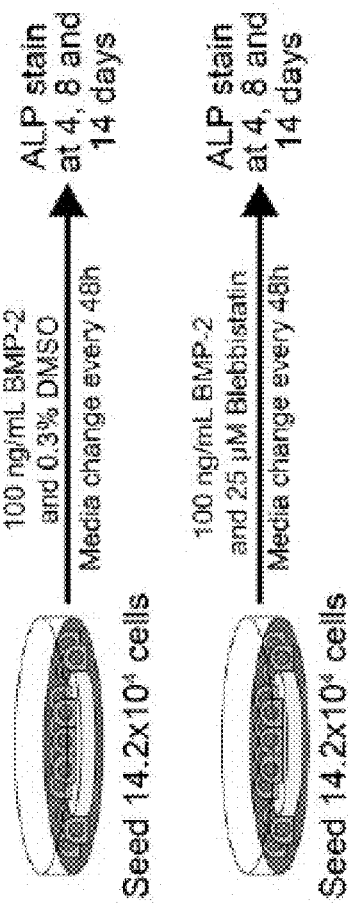
FIGS. 9A-9D show effect of UV-exposed QHM polymers on C2C12 osteoblast differentiation in the presence or absence of 25 μm blebbistatin.
Figure 9B:
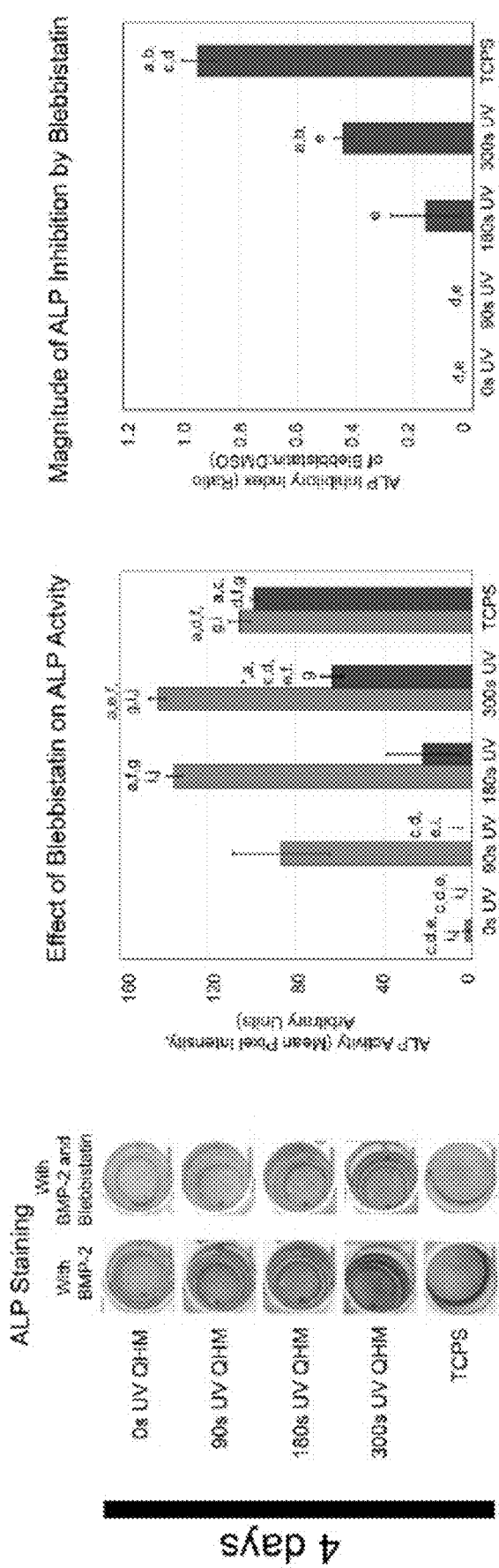
Figure 9C:
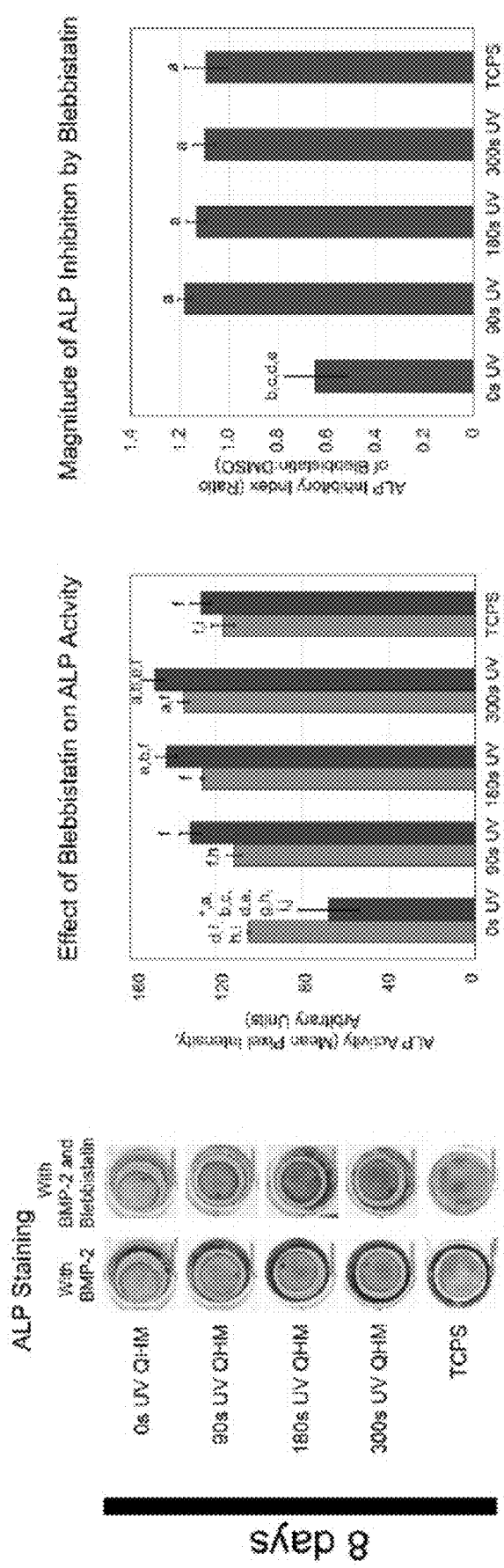
Figure 9D:
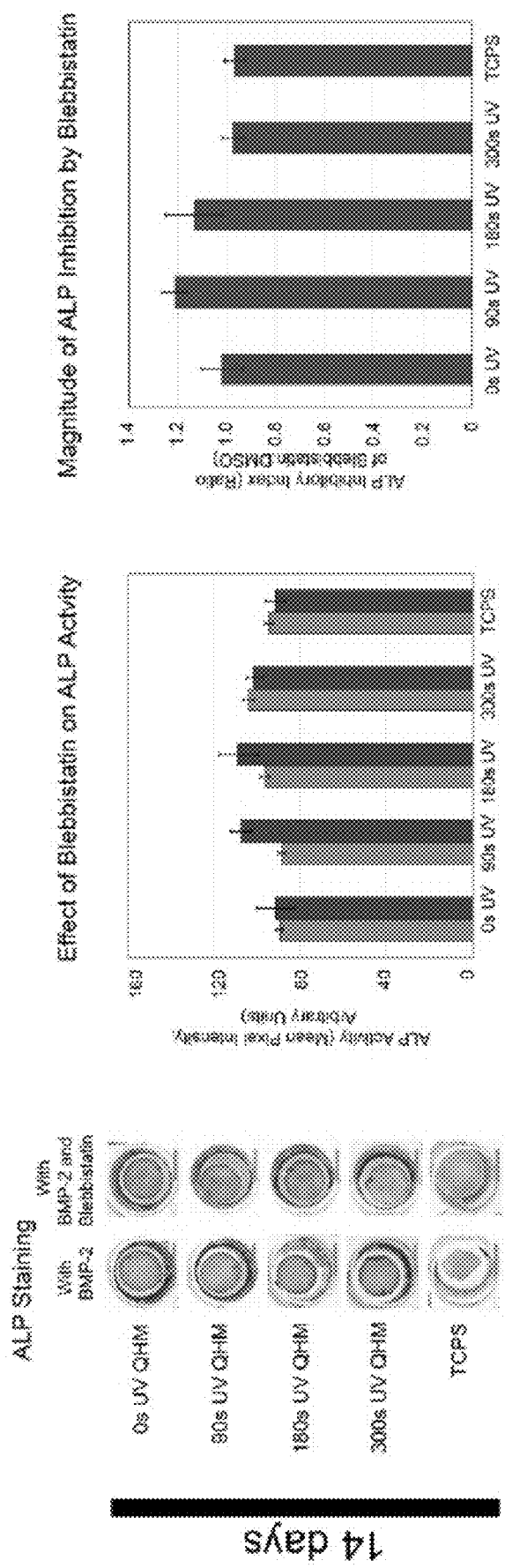

Substrate stiffness affected C2C12 osteoblast differentiation. C2C12 cells cultured in 100 ng/mL BMP-2 for 4 days without blebbistatin exhibited increased ALP activity on stiffer QHM polymers (FIGS. 9A-9D and Table 11). In the presence of 25 µM blebbistatin, BMP-2-induced ALP activity was inhibited slightly but the overall trend of increased ALP activity on stiffer QHM polymers remained (FIG. 9B and Table 11). Interestingly, blebbistatin did not inhibit C2C12 ALP activity on tissue culture-grade polystyrene (TCPS). The magnitude of this inhibition (determined by the ratio of C2C12 ALP activity between blebbistatin- and DMSO-treated cells) was less severe in stiffer QHM polymers whereas TCPS controls were unperturbed (FIG. 9B and Table 12). With increased culture duration, the inhibitory effect of blebbistatin on ALP activity occurred only on 0 s UV QHM polymer at 8 days (FIG. 9C, Tables 13 and 14) and was no longer observed at 14 days (FIG. 9D, Tables 15 and 16). Increased substrate stiffness also increased C2C12 ALP activity on mechanically-graded QHM polymers (FIG. 14A-14B).

To determine if mechanically-graded QHM polymers recapitulated similar stiffness effects on osteoblast and tenocyte differentiation as uniform QHM polymers, ALP and SCX staining were performed on mechanically-graded QHM polymers that were seeded with C2C12 cells and cultured in the presence of 100 ng/mL BMP-2 or 100 ng/mL FGF-2 for 3 days (FIG. 14A-14B). C2C12 cells subjected to 100 ng/mL BMP-2 for 3 days on the 300 s UV region of QHM polymers exhibited increased ALP activity relative to 0 s UV region (FIG. 14A). C2C12 cells subjected to 100 ng/mL FGF-2 for 3 days on the 300 s UV region of QHM polymers exhibited decreased SCX expression relative to 300 s UV region (FIG. 14A). Additional staining for osteoblast markers RUNT-RELATED TRANSCRIPTION FACTOR-2 (RUNX2) and OSTEOCALCIN (OCN) in C2C12 cells cultured in the presence of 100 ng/mL BMP-2 for 4 days indicated that osteogenic differentiation occurred on QHM polymers although no differences were observed (FIG. 14B). Together, these data demonstrated that stiffer QHM polymers increased and decreased C2C12 osteoblast and tenocyte differentiation, respectively, on mechanically-graded QHM polymers.

TABLE 11

P values comparing C2C12 ALP activity on QHM polymers in the presence or absence of 25 µM blebbistatin for 4 days.

| Group | Group | P value |
| --- | --- | --- |
| DMSO 0 s UV QHM polymer | DMSO 90 s UV QHM polymer | 0.311 |
| DMSO 0 s UV QHM polymer | DMSO 180 s UV QHM polymer | 0.001 |
| DMSO 0 s UV QHM polymer | DMSO 300 s UV QHM polymer | 0.002 |
| DMSO 0 s UV QHM polymer | DMSO TCPS | 0.008 |
| DMSO 90 s UV QHM polymer | DMSO 180 s UV QHM polymer | 0.652 |
| DMSO 90 s UV QHM polymer | DMSO 300 s UV QHM polymer | 0.554 |
| DMSO 90 s UV QHM polymer | DMSO TCPS | 0.992 |
| DMSO 180 s UV QHM polymer | DMSO 300 s UV QHM polymer | 0.891 |
| DMSO 180 s UV QHM polymer | DMSO TCPS | 0.092 |
| DMSO 300 s UV QHM polymer | DMSO TCPS | 0.046 |
| 25 µM blebbistatin 0 s UV QHM polymer | 25 µM blebbistatin 90 s UV QHM polymer | 0.955 |

TABLE 11-continued

P values comparing C2C12 ALP activity on QHM polymers in the presence or absence of 25 µM blebbistatin for 4 days.

| Group | Group | P value |
|---|---|---|
| 25 µM blebbistatin 0 s UV QHM polymer | 25 µM blebbistatin 180 s UV QHM polymer | 0.910 |
| 25 µM blebbistatin 0 s UV QHM polymer | 25 µM blebbistatin 300 s UV QHM polymer | 0.035 |
| 25 µM blebbistatin 0 s UV QHM polymer | 25 µM blebbistatin TCPS | 0.002 |
| 25 µM blebbistatin 90 s UV QHM polymer | 25 µM blebbistatin 180 s UV QHM polymer | 0.914 |
| 25 µM blebbistatin 90 s UV QHM polymer | 25 µM blebbistatin 300 s UV QHM polymer | 0.035 |
| 25 µM blebbistatin 90 s UV QHM polymer | 25 µM blebbistatin TCPS | 0.001 |
| 25 µM blebbistatin 180 s UV QHM polymer | 25 µM blebbistatin 300 s UV QHM polymer | 0.576 |
| 25 µM blebbistatin 180 s UV QHM polymer | 25 µM blebbistatin TCPS | 0.223 |
| 25 µM blebbistatin 300 s UV QHM polymer | 25 µM blebbistatin TCPS | 0.085 |
| DMSO 0 s UV QHM polymer | 25 µM blebbistatin 0 s UV QHM polymer | 0.634 |
| DMSO 90 s UV QHM polymer | 25 µM blebbistatin 90 s UV QHM polymer | 0.297 |
| DMSO 180 s UV QHM polymer | 25 µM blebbistatin 180 s UV QHM polymer | 0.103 |
| DMSO 300 s UV QHM polymer | 25 µM blebbistatin 300 s UV QHM polymer | 0.004 |
| DMSO TCPS | 25 µM blebbistatin TCPS | 0.918 |

TABLE 12

P values comparing magnitude of C2C12 ALP inhibition by 25 µM blebbistatin at 4 days.

| Group | Group | P value |
|---|---|---|
| 0 s UV QHM polymer | 90 UV QHM polymer | 0.789 |
| 0 UV QHM polymer | 180 UV QHM polymer | 0.705 |
| 0 UV QHM polymer | 300 UV QHM polymer | 0.015 |
| 0 UV QHM polymer | TCPS | 0.010 |
| 90 UV QHM polymer | 180 UV QHM polymer | 0.715 |
| 90 UV QHM polymer | 300 UV QHM polymer | 0.015 |
| 90 UV QHM polymer | TCPS | 0.010 |
| 180 UV QHM polymer | 300 UV QHM polymer | 0.387 |
| 180 UV QHM polymer | TCPS | 0.044 |
| 300 UV QHM polymer | TCPS | 0.013 |

TABLE 13

P values comparing C2C12 ALP activity on QHM polymers in the presence or absence of 25 µM blebbistatin at 8 days.

| Group | Group | P value |
|---|---|---|
| DMSO 0 s UV QHM polymer | DMSO 90 s UV QHM polymer | 0.996 |
| DMSO 0 s UV QHM polymer | DMSO 180 s UV QHM polymer | 0.250 |
| DMSO 0 s UV QHM polymer | DMSO 300 s UV QHM polymer | 0.034 |
| DMSO 0 s UV QHM polymer | DMSO TCPS | 0.882 |
| DMSO 90 s UV QHM polymer | DMSO 180 s UV QHM polymer | 0.718 |
| DMSO 90 s UV QHM polymer | DMSO 300 s UV QHM polymer | 0.177 |
| DMSO 90 s UV QHM polymer | DMSO TCPS | 1.000 |
| DMSO 180 s UV QHM polymer | DMSO 300 s UV QHM polymer | 0.984 |
| DMSO 180 s UV QHM polymer | DMSO TCPS | 0.967 |
| DMSO 300 s UV QHM polymer | DMSO TCPS | 0.463 |
| 25 µM blebbistatin 0 s UV QHM polymer | 25 µM blebbistatin 90 s UV QHM polymer | 0.000 |
| 25 µM blebbistatin 0 s UV QHM polymer | 25 µM blebbistatin 180 s UV QHM polymer | 0.000 |
| 25 µM blebbistatin 0 s UV QHM polymer | 25 µM blebbistatin 300 s UV QHM polymer | 0.000 |
| 25 µM blebbistatin 0 s UV QHM polymer | 25 µM blebbistatin TCPS | 0.000 |
| 25 µM blebbistatin 90 s UV QHM polymer | 25 µM blebbistatin 180 s UV QHM polymer | 0.910 |
| 25 µM blebbistatin 90 s UV QHM polymer | 25 µM blebbistatin 300 s UV QHM polymer | 0.558 |

TABLE 13-continued

P values comparing C2C12 ALP activity on QHM polymers in
the presence or absence of 25 μM blebbistatin at 8 days.

| Group | Group | P value |
|---|---|---|
| 25 μM blebbistatin 90 s UV QHM polymer | 25 μM blebbistatin TCPS | 1.000 |
| 25 μM blebbistatin 180 s UV QHM polymer | 25 μM blebbistatin 300 s UV QHM polymer | 0.999 |
| 25 μM blebbistatin 180 s UV QHM polymer | 25 μM blebbistatin TCPS | 0.621 |
| 25 μM blebbistatin 300 s UV QHM polymer | 25 μM blebbistatin TCPS | 0.258 |
| DMSO 0 s UV QHM polymer | 25 μM blebbistatin 0 s UV QHM polymer | 0.006 |
| DMSO 90 s UV QHM polymer | 25 μM blebbistatin 90 s UV QHM polymer | 0.335 |
| DMSO 180 s UV QHM polymer | 25 μM blebbistatin 180 s UV QHM polymer | 0.564 |
| DMSO 300 s UV QHM polymer | 25 μM blebbistatin 300 s UV QHM polymer | 0.792 |
| DMSO TCPS | 25 μM blebbistatin TCPS | 0.948 |

TABLE 14

P values comparing magnitude of C2C12 ALP
inhibition by 25 μM blebbistatin at 8 days.

| Group | Group | P value |
|---|---|---|
| 0 s UV QHM polymer | 90 UV QHM polymer | 0.004 |
| 0 UV QHM polymer | 180 UV QHM polymer | 0.007 |
| 0 UV QHM polymer | 300 UV QHM polymer | 0.010 |
| 0 UV QHM polymer | TCPS | 0.011 |
| 90 UV QHM polymer | 180 UV QHM polymer | 0.991 |
| 90 UV QHM polymer | 300 UV QHM polymer | 0.944 |
| 90 UV QHM polymer | TCPS | 0.928 |
| 180 UV QHM polymer | 300 UV QHM polymer | 0.998 |
| 180 UV QHM polymer | TCPS | 0.996 |
| 300 UV QHM polymer | TCPS | 1.000 |

TABLE 15

P values comparing C2C12 ALP activity on QHM polymers in
the presence or absence of 25 μM blebbistatin at 14 days.

| Group | Group | P value |
|---|---|---|
| DMSO 0 s UV QHM polymer | DMSO 90 s UV QHM polymer | 1.000 |
| DMSO 0 s UV QHM polymer | DMSO 180 s UV QHM polymer | 0.987 |
| DMSO 0 s UV QHM polymer | DMSO 300 s UV QHM polymer | 0.529 |
| DMSO 0 s UV QHM polymer | DMSO TCPS | 0.999 |
| DMSO 90 s UV QHM polymer | DMSO 180 s UV QHM polymer | 0.976 |
| DMSO 90 s UV QHM polymer | DMSO 300 s UV QHM polymer | 0.471 |
| DMSO 90 s UV QHM polymer | DMSO TCPS | 0.998 |
| DMSO 180 s UV QHM polymer | DMSO 300 s UV QHM polymer | 0.978 |
| DMSO 180 s UV QHM polymer | DMSO TCPS | 1.000 |
| DMSO 300 s UV QHM polymer | DMSO TCPS | 0.905 |
| 25 μM blebbistatin 0 s UV QHM polymer | 25 μM blebbistatin 90 s UV QHM polymer | 0.402 |
| 25 μM blebbistatin 0 s UV QHM polymer | 25 μM blebbistatin 180 s UV QHM polymer | 0.302 |
| 25 μM blebbistatin 0 s UV QHM polymer | 25 μM blebbistatin 300 s UV QHM polymer | 0.892 |
| 25 μM blebbistatin 0 s UV QHM polymer | 25 μM blebbistatin TCPS | 1.000 |
| 25 μM blebbistatin 90 s UV QHM polymer | 25 μM blebbistatin 180 s UV QHM polymer | 1.000 |
| 25 μM blebbistatin 90 s UV QHM polymer | 25 μM blebbistatin 300 s UV QHM polymer | 0.995 |
| 25 μM blebbistatin 90 s UV QHM polymer | 25 μM blebbistatin TCPS | 0.401 |
| 25 μM blebbistatin 180 s UV QHM polymer | 25 μM blebbistatin 300 s UV QHM polymer | 0.981 |
| 25 μM blebbistatin 180 s UV QHM polymer | 25 μM blebbistatin TCPS | 0.301 |
| 25 μM blebbistatin 300 s UV QHM polymer | 25 μM blebbistatin TCPS | 0.891 |
| DMSO 0 s UV QHM polymer | 25 μM blebbistatin 0 s UV QHM polymer | 1.000 |
| DMSO 90 s UV QHM polymer | 25 μM blebbistatin 90 s UV QHM polymer | 0.232 |
| DMSO 180 s UV QHM polymer | 25 μM blebbistatin 180 s UV QHM polymer | 0.731 |
| DMSO 300 s UV QHM polymer | 25 μM blebbistatin 300 s UV QHM polymer | 1.000 |
| DMSO TCPS | 25 μM blebbistatin TCPS | 1.000 |

TABLE 16

P values comparing magnitude of C2C12 ALP inhibition
by 25 µM blebbistatin at 14 days.

| Group | Group | P value |
|---|---|---|
| 0 s UV QHM polymer | 90 UV QHM polymer | 0.405 |
| 0 UV QHM polymer | 180 UV QHM polymer | 0.808 |
| 0 UV QHM polymer | 300 UV QHM polymer | 0.992 |
| 0 UV QHM polymer | TCPS | 0.986 |
| 90 UV QHM polymer | 180 UV QHM polymer | 0.940 |
| 90 UV QHM polymer | 300 UV QHM polymer | 0.234 |
| 90 UV QHM polymer | TCPS | 0.212 |
| 180 UV QHM polymer | 300 UV QHM polymer | 0.577 |
| 180 UV QHM polymer | TCPS | 0.538 |
| 300 UV QHM polymer | TCPS | 1.000 |

Figures 10A, 10B:
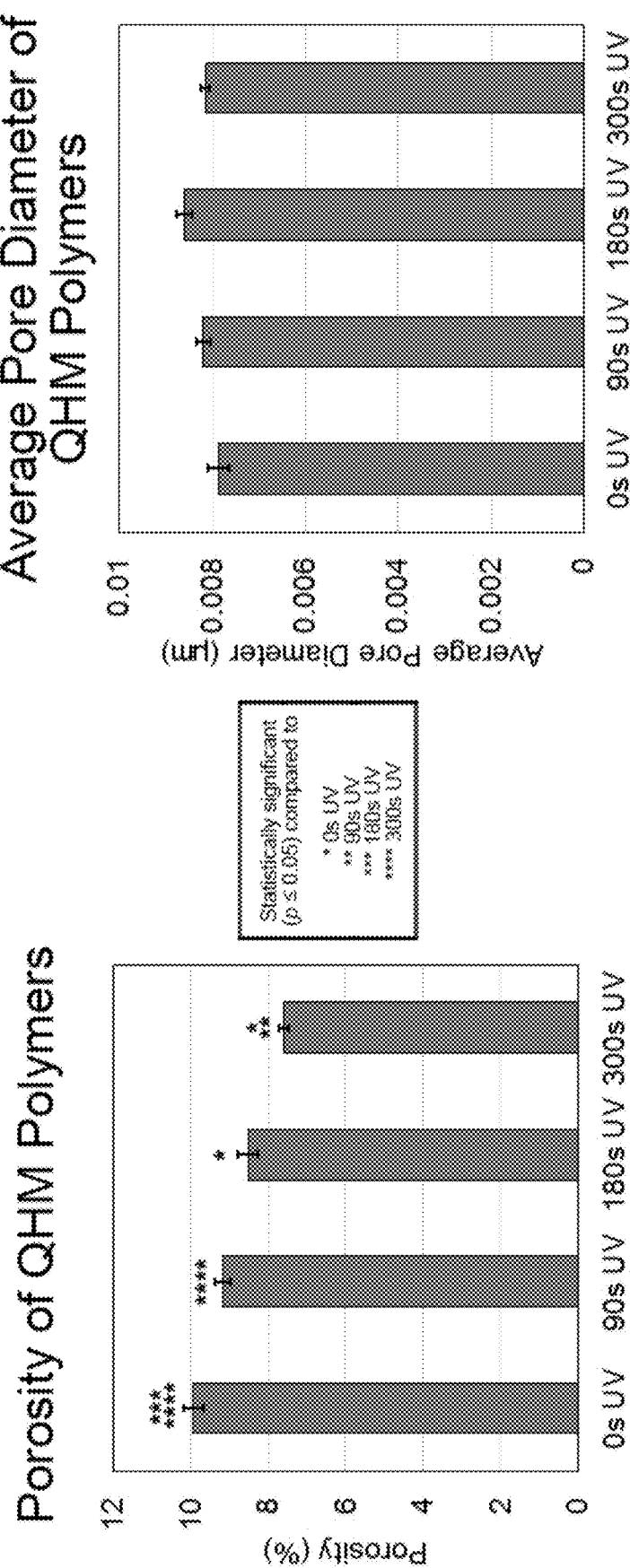
FIGS. 10A and 10B show graphs of effect of UV-exposure on porosity and pore diameter of QHM polymers.

To ascertain whether increased ALP activity observed on longer UV-exposed QHM polymers was due to increased stiffness, it was necessary to rule out potentially confounding factors including porosity, surface roughness, cell attachment, BMP-2 dose and administration. Mercury intrusion porosimetry showed that QHM polymer porosity differed less than 2.5% (FIG. 10A) and pore sizes were similar (FIG. 10B). To measure material porosity, mercury intrusion tests were conducted. The porosity of 0 s UV, 90 s UV, 180 s UV and 300 s UV QHM polymers were 9.93%, 9.17%, 8.52% and 7.59%, respectively ($p=0.142$ for 0 s UV versus 90 s UV; $p=0.008$ for 0 s UV versus 180 s UV; $p<0.001$ for 0 s UV versus 300 s UV; $p=0.235$ for 90 s UV versus 180 s UV; $p=0.004$ for 90 s UV versus 300 s UV and $p=0.066$ for 180 s UV versus 300 s UV; FIG. 10A). The average pore diameter of 0 s UV, 90 s UV, 180 s UV ad 300 s UV QHM polymers were 0.0079 µm, 0.0082 µm, 0.0086 µm and 0.0082 µm, respectively ($p>0.06$ for all cases; FIG. 10B). As such, QHM polymer porosity decreased with longer UV-exposure whereas average pore diameter did not change.

Figure 11:
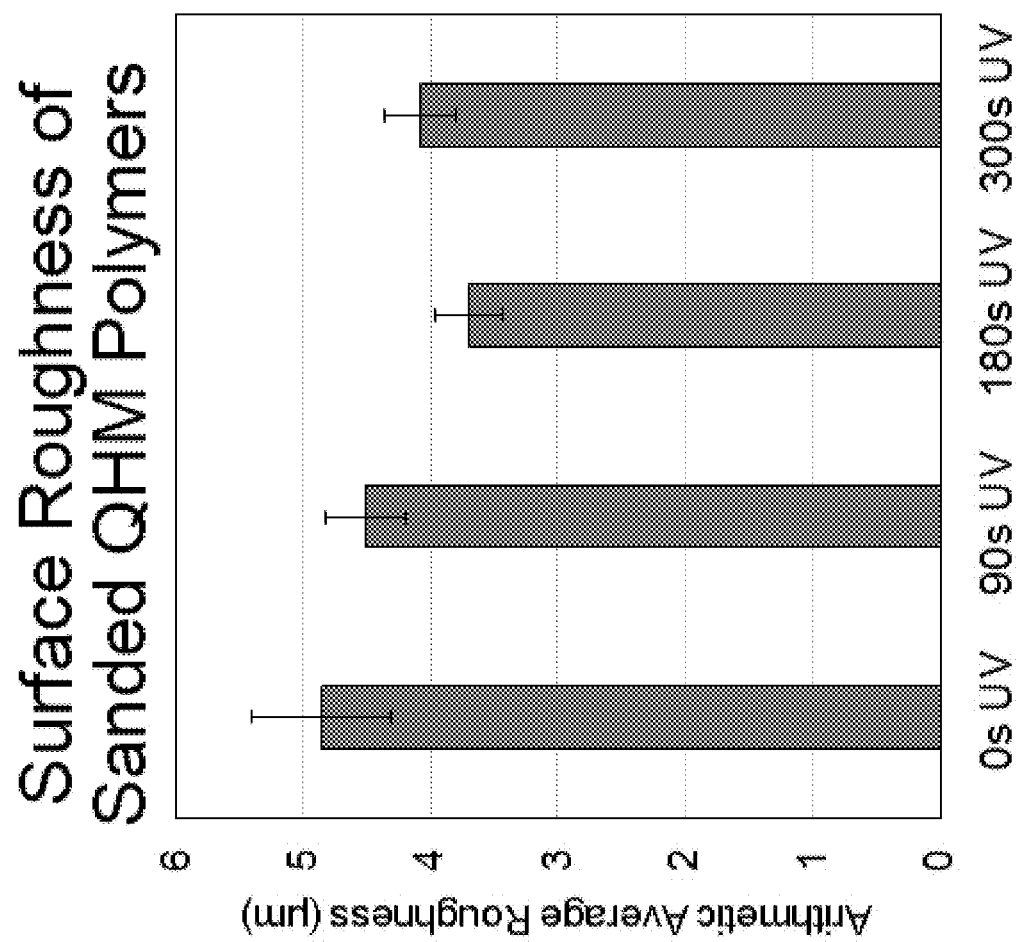
FIG. 11 shows a graph of effect of sanding on surface roughness of QHM polymers. The arithmetic average roughness was computed (n=3). Error bars indicate standard error of mean.

Surface profilometry determined that QHM polymers had similar surface roughness (FIG. 11). To determine the effect of sanding on the surface roughness of QHM polymers, profilometer measurements were performed. The arithmetic average roughness of sanded 0 s UV, 90 s UV, 180 s UV and 300 s UV QHM polymers were 4.86 µm, 4.51 µm, 3.71 µm and 4.09 µm, respectively ($p=0.906$ for 0 s UV versus 90 s UV, $p=0.142$ for 0 s UV versus 180 s UV, $p=0.460$ for 0 s UV versus 300 s UV, $p=0.428$ for 90 s UV versus 180 s UV, $p=0.851$ for 90 s UV versus 300 s UV and $p=0.884$ for 180 s UV versus 300 s UV; FIG. 11). As such, the surface roughness of QHM polymers were similar after sanding.

Figure 12B:
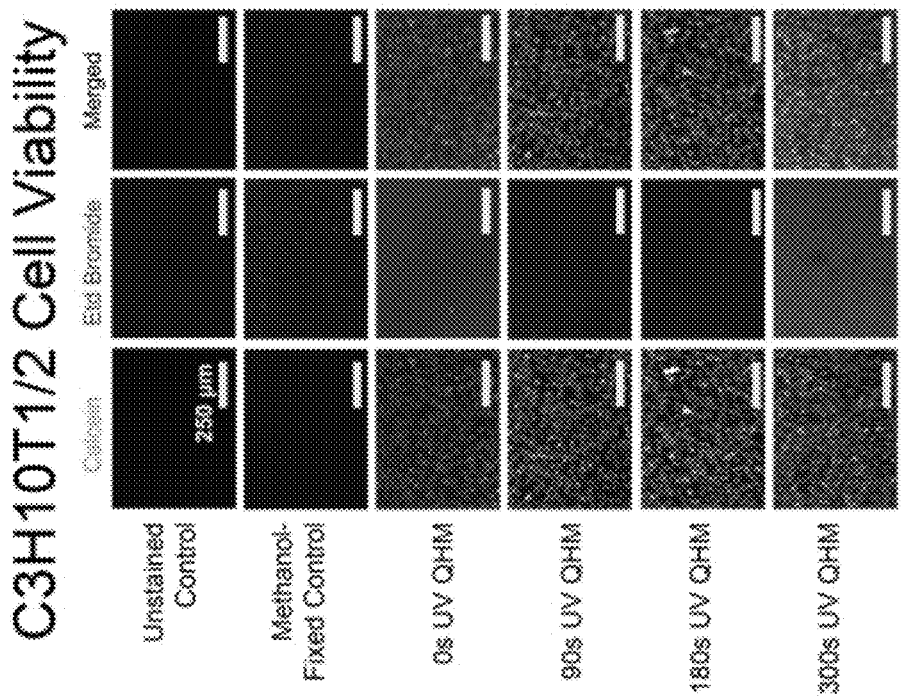
FIGS. 12A and 12B show a graph and images of cell attachment and cell viability of C3H10T1/2 cells on QHM polymers, tissue culture-treated polystyrene (TCPS) and low cell attachment polystyrene (PS).
Figure 12A:
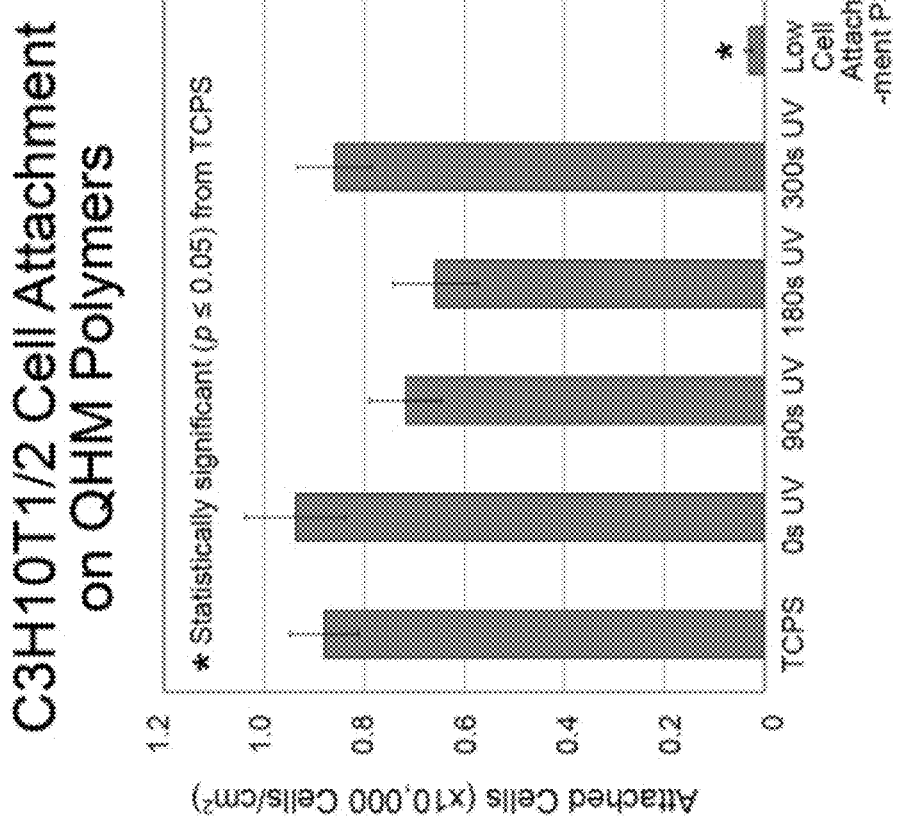

In addition, the attachment, viability and proliferation of musculoskeletal progenitor cells such as C3H10T1/2 cells (FIGS. 12A-12B) and C2C12 cells (FIG. 13A-13B) on QHM polymers were similar. To monitor initial cell-biomaterial interactions, cell attachment, cell viability and cell proliferation studies were performed using C3H10T1/2 and C2C12 musculoskeletal progenitor cells. C3H10T1/2 cells attached to tissue culture-grade polystyrene (TCPS), 0 s UV QHM polymer, 90 s UV QHM polymer, 180 s UV QHM polymer, 300 s UV QHM polymer and low cell attachment polystyrene (PS) at $0.880\times10^4$ cells/cm$^2$, $0.937\times10^4$ cells/cm$^2$, $0.718\times10^4$ cells/cm$^2$, $0.659\times10^4$ cells/cm$^2$, $0.859\times10^4$ cells/cm$^2$ and $0.032\times10^4$ cells/cm$^2$, respectively (FIG. 12A-12B). Cell attachment to QHM polymers and TCPS were similar ($p=0.299$ for 0 s UV versus 90 s UV, $p=0.096$ for 0 s UV versus 180 s UV, $p=0.976$ for 0 s UV versus 300 s UV, $p=0.994$ for 0 s UV versus TCPS, $p=0.993$ for 90 s UV versus 180 s UV, $p=0.751$ for 90 s UV versus 300 s UV, $p=0.629$ for 90 s UV versus TCPS, $p=0.396$ for 180 s UV versus 300 s UV, $p=0.288$ for 180 s UV versus TCPS and $p>0.999$ for 300 s UV versus TCPS) but were increased when compared to low cell attachment PS control ($p<0.001$ for all cases). C3H10T1/2 cells seeded on QHM polymers for 5 days exhibited strong calcein fluorescence and low ethidium bromide fluorescence although some polymer autofluorescence was observed (FIG. 12B). Similarly, C2C12 cells seeded on QHM polymers for 5 days also exhibited strong calcein fluorescence and low ethidium bromide fluorescence (FIG. 13A; Lower levels of polymer autofluorescence were observed in the C2C12 viability studies compared to C3H10T1/2 viability studies due to use of thinner QHM polymer samples). C2C12 cells seeded on TCPS, 0 s UV QHM polymer, 90 s UV QHM polymer, 180 s UV QHM polymer and 300 s UV QHM polymer proliferated over 5 days of culture but cells seeded on TCPS with ethanol treatment did not (FIG. 13B). Day 5 cell numbers for TCPS, 0 s UV QHM polymer, 90 s UV QHM polymer, 180 s UV QHM polymer, 300 s UV QHM polymer and TCPS with ethanol treatment were $21.370\times10^4$ cells/cm$^2$, $9.363\times10^4$ cells/cm$^2$, $11.929\times10^4$ cells/cm$^2$, $14.338\times10^4$ cells/cm$^2$, $14.479\times10^4$ cells/cm$^2$ and $0.2021\times10^4$ cells/cm$^2$, respectively. Day 5 cell numbers among QHM polymers were similar ($p=0.664$ for 0 s UV versus 90 s UV, $p=0.066$ for 0 s UV versus 180 s UV, $p=0.055$ for 0 s UV versus 300 s UV, $p=0.719$ for 90 s UV versus 180 s UV, $p=0.670$ for 90 s UV versus 300 s UV and $p>0.999$ for 180 s UV versus 300 s UV). However, Day 5 cell numbers for QHM polymers were decreased compared to TCPS ($p<0.001$ for 0 s UV versus TCPS, $p<0.001$ for 90 s UV versus TCPS, $p=0.003$ for 180 s UV versus TCPS and $p=0.004$ for 300 s UV versus TCPS) but were increased compared to TCPS with ethanol treatment ($p<0.001$ for all cases). Together, these data demonstrated that QHM polymers support cell attachment, cell viability and cell proliferation.

Furthermore, C2C12 ALP activity was also observed on TCPS regions of all wells that contained QHM polymers, indicating that ALP inhibition was not attributed to leaching of unreacted components or degradation products (FIGS. 9A-9D and FIG. 15A-15B). The loss of C2C12 ALP inhibition with longer culture durations was attributed to increased BMP-2 administration (FIG. 15A). Increased BMP-2 dose also increased C2C12 ALP activity (FIG. 15B). With even longer culture durations (27 days), C2C12 cells mineralized on QHM polymers (FIG. 16).

Substrate stiffness affected C2C12 tenocyte differentiation. C2C12 cells cultured in 100 ng/mL FGF-2 for 3 days exhibited decreased SCX expression on stiffer QHM polymers (FIG. 18). This trend was also observed on mechanically-graded QHM polymers (FIGS. 14A-14B).

To determine the effect of BMP-2 dose and administration on osteogenic differentiation, ALP staining was performed on C2C12 cell-seeded QHM polymers that were subjected to different BMP-2 regimens (4 days BMP-2 administration or 6 days BMP-2 administration) or doses (100 ng/mL BMP-2 or 200 ng/mL BMP-2).

C2C12 cells that were subjected to 4 days of BMP-2 (4 days of culture in media containing BMP-2 followed by 2 days of culture in media lacking BMP-2) on 0 s UV, 90 s UV, 180 s UV and 300 s UV QHM polymers, and TCPS control exhibited ALP activities of 8.17, 6.28, 17.73, 36.80 and 41.31, respectively (FIG. 15A). This ALP activity increased with longer UV-exposure on QHM polymers ($p>0.999$ for 0 s UV versus 90 s UV, $p=0.878$ for 0 s UV versus 180 s UV, $p=0.001$ for 0 s UV versus 300 s UV, $p<0.001$ for 0 s UV versus TCPS, $p=0.709$ for 90 s UV versus 180 s UV, $p<0.001$ for 90 s UV versus 300 s UV, $p<0.001$ for 90 s UV versus TCPS, p=0.078 for 180 s UV versus 300 s UV, p=0.010 for 180 s UV versus TCPS and p>0.999 for 300 s UV versus TCPS). C2C12 cells that were subjected to 6 days of BMP-2 (6 days of culture in media containing BMP-2) on 0 s UV, 90 s UV, 180 s UV and 300 s UV QHM polymers, and TCPS control exhibited ALP activities of 10.38, 22.14, 86.15, 99.47 and 49.59, respectively (FIG. 15A). This ALP activity increased with longer UV-exposure on QHM polymers (p=0.675 for 0 s UV versus 90 s UV, p<0.001 for 0 s UV versus 180 s UV, p<0.001 for 0 s UV versus 300 s UV, p<0.001 for 0 s UV versus TCPS, p<0.001 for 90 s UV versus 180 s UV, p<0.001 for 90 s UV versus 300 s UV, p=0.001 for 90 s UV versus TCPS, p=0.500 for 180 s UV versus 300 s UV, p<0.001 for 180 s UV versus TCPS and p<0.001 for 300 s UV versus TCPS). Increased BMP-2 administration increased the ALP activity of C2C12 cells on QHM polymers subjected to longer UV-exposure (p>0.999 for 6 Day 0 s UV versus 4 Day 0 s UV, p=0.252 for 6 Day 90 s UV versus 4 Day 90 s UV, p<0.001 for 6 Day 180 s UV versus 4 Day 180 s UV, p<0.001 for 6 Day 300 s UV versus 4 Day 300 s UV) but surprisingly, had no effect on C2C12 cells cultured on TCPS (p=0.948 for 6 Day TCPS versus 4 Day TCPS).

C2C12 cells that were subjected to 100 ng/mL BMP-2 for 4 days on 0 s UV, 90 s UV, 180 s UV and 300 s UV QHM polymers, and TCPS control exhibited ALP activities of 8.26, 15.64, 31.96, 62.94 and 126.14, respectively (FIG. 15B). This ALP activity increased with longer UV-exposure on QHM polymers (p>0.999 for 0 s UV versus 90 s UV, p=0.701 for 0 s UV versus 180 s UV, p=0.003 for 0 s UV versus 300 s UV, p<0.001 for 0 s UV versus TCPS, p=0.955 for 90 s UV versus 180 s UV, p=0.018 for 90 s UV versus 300 s UV, p<0.001 for 90 s UV versus TCPS, p=0.337 for 180 s UV versus 300 s UV, p<0.001 for 180 s UV versus TCPS and p<0.001 for 300 s UV versus TCPS). C2C12 cells that were subjected to 200 ng/mL BMP-2 for 4 days on 0 s UV, 90 s UV, 180 s UV and 300 s UV QHM polymers, and TCPS control exhibited ALP activities of 59.31, 76.94, 102.43, 110.13 and 122.23, respectively (FIG. 15B). This ALP activity increased with longer UV-exposure on QHM polymers (p=0.929 for 0 s UV versus 90 s UV, p=0.043 for 0 s UV versus 180 s UV, p=0.008 for 0 s UV versus 300 s UV, p<0.001 for 0 s UV versus TCPS, p=0.610 for 90 s UV versus 180 s UV, p=0.249 for 90 s UV versus 300 s UV, p=0.028 for 90 s UV versus TCPS, p>0.999 for 180 s UV versus 300 s UV, p=0.867 for 180 s UV versus TCPS and p=0.994 for 300 s UV versus TCPS). Increased BMP-2 dose increased the ALP activity of C2C12 cells on QHM polymers (p=0.008 for 100 ng/mL BMP-2 0 s UV versus 200 ng/mL BMP-2 0 s UV, p=0.001 for 100 ng/mL BMP-2 90 s UV versus 200 ng/mL BMP-2 90 s UV, p<0.001 for 100 ng/mL BMP-2 180 s UV versus 200 ng/mL BMP-2 180 s UV, p=0.018 for 100 ng/mL BMP-2 300 s UV versus 200 ng/mL BMP-2 300 s UV) but surprisingly, had no effect on C2C12 cells cultured on TCPS (p>0.999 for 100 ng/mL BMP-2 TCPS versus 200 ng/mL BMP-2 TCPS). Together, these data demonstrated that increased BMP-2 administration and increased BMP-2 dose increased the ALP activity of C2C12 cells cultured on QHM polymers.

To assess osteogenic differentiation on QHM polymers, mineralization studies using C2C12 cells were performed with alizarin red and von Kossa staining. After 27 days culture in control and osteogenic media, all QHM polymers stained positive (Black) for phosphate with more positive staining observed in samples cultured in osteogenic media (FIG. 16). Alizarin red mineralization studies were inconclusive due to the inability of Alizarin red dye to be washed out from QHM polymers (Data not shown). As such, these data indicated that C2C12 cells mineralized on QHM polymers.

To determine the effect of FGF-2 on tenocyte differentiation, C2C12 cells were cultured on TCPS with 0 ng/mL, 50 ng/mL or 100 ng/mL FGF-2 and expression of tenocyte markers, TENASCIN C and TENOMODULIN were determined. Increased FGF-2 dose resulted in increased TENASCIN C expression relative to untreated controls (FIG. 17; p=0.153 for 0 ng/mL FGF-2 versus 50 ng/mL FGF-2, p<0.001 for 0 ng/mL FGF-2 versus 100 ng/mL FGF-2 and p<0.001 for 50 ng/mL FGF-2 versus 100 ng/mL FGF-2). Also, increased FGF-2 dose resulted in increased TENOMODULIN expression relative to untreated controls (FIG. 17; p<0.001 for 0 ng/mL FGF-2 versus 50 ng/mL FGF-2, p<0.001 for 0 ng/mL FGF-2 versus 100 ng/mL FGF-2 and p<0.001 for 50 ng/mL FGF-2 versus 100 ng/mL FGF-2). As such, FGF-2 promoted C2C12 tenocyte differentiation.

To determine the effect of QHM polymer stiffness on tenocyte differentiation, C2C12 cells were cultured on fibrin-coated QHM polymers with 100 ng/mL FGF-2 and expression of tenocyte marker SCX was determined. Increased SCX expression was observed on fibrin-coated 0 s UV QHM polymer relative to fibrin-coated 90 s UV, 180 s UV and 300 s UV QHM polymers (FIG. 18; p<0.001 for 0 s UV versus 90 s UV, p<0.001 for 0 s UV versus 180 s UV, p<0.001 for 0 s UV versus 300 s UV, p=0.919 for 90 s UV versus 180 s UV, p=0.700 for 90 s UV versus 300 s UV and p=0.328 for 180 s UV versus 300 s UV). As such, decreasing stiffness of fibrin-coated QHM polymers promoted FGF-2 mediated C2C12 tenocyte differentiation.

In conclusion, these data suggest that increased QHM polymer stiffness, as a result of longer UV-exposure, increased and decreased growth factor-mediated C2C12 osteoblast and tenocyte differentiation, respectively.

Figure 19A:
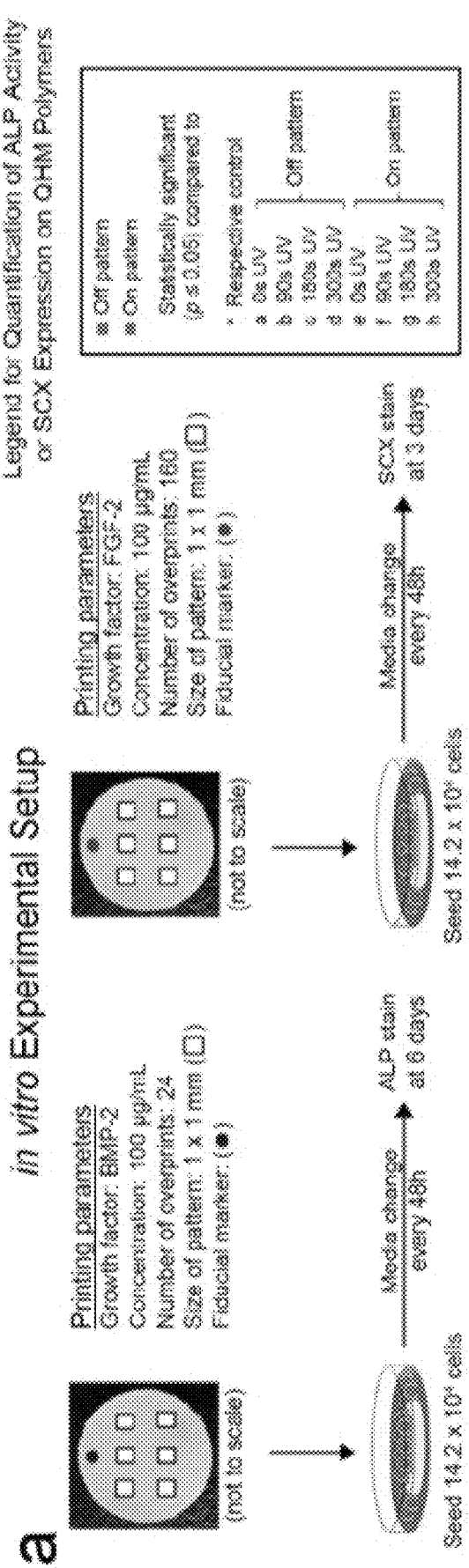
FIGS. 19A-19E show the effect of BMP-2 and FGF-2 biopatterning on spatial control of C2C12 osteoblast and tenocyte differentiation.
Figure 19B:
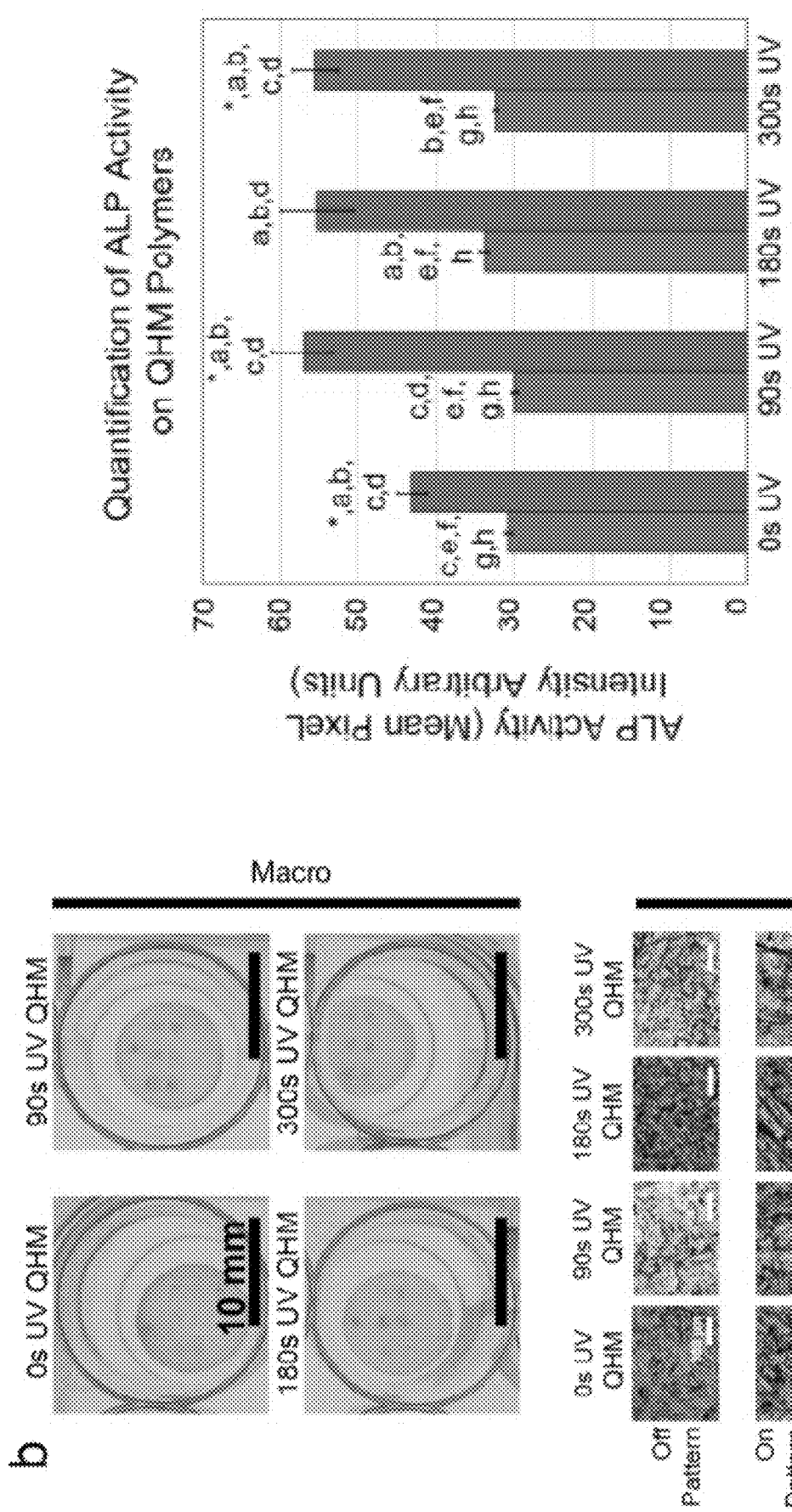
Figure 19C:
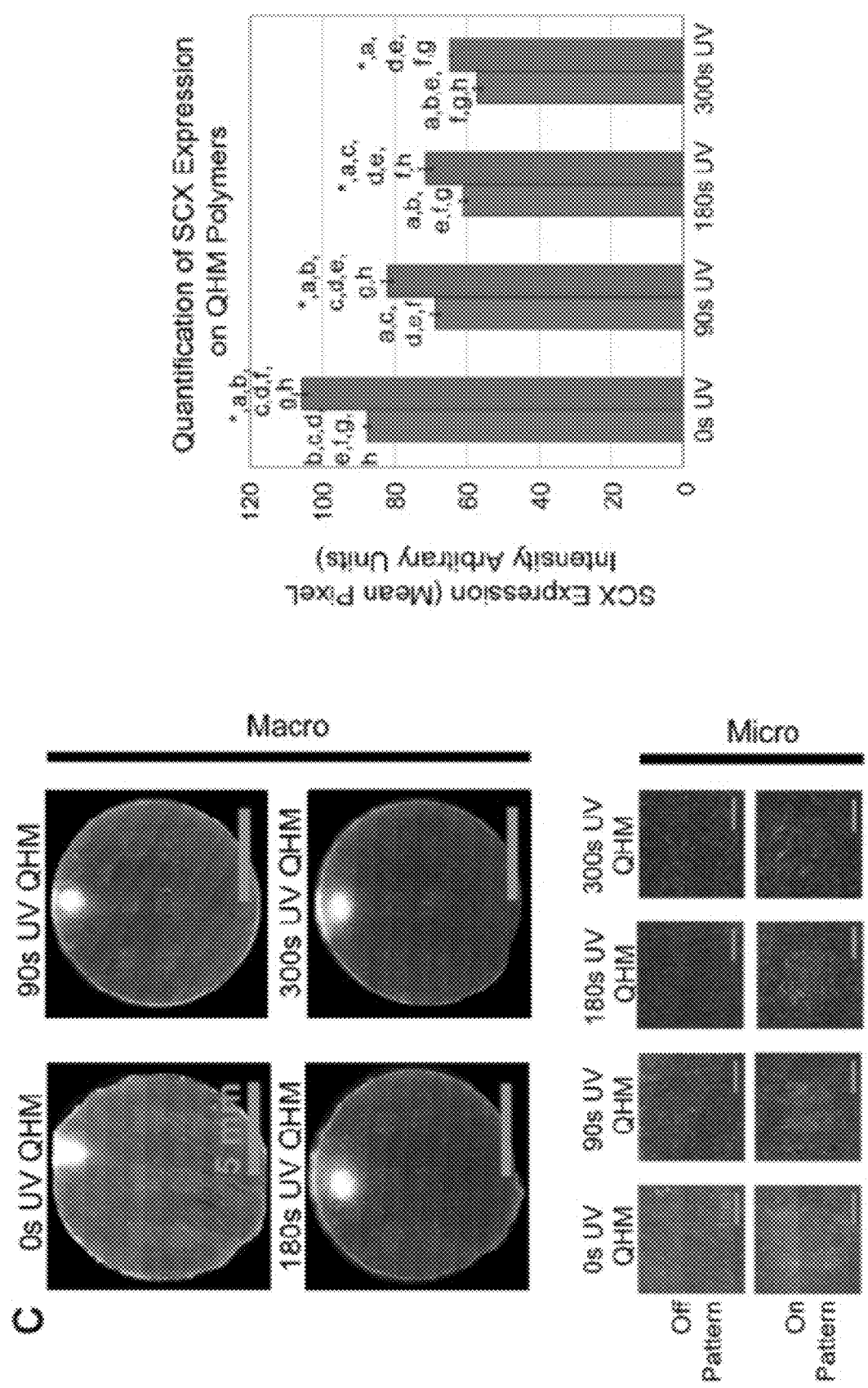
Figure 19D:
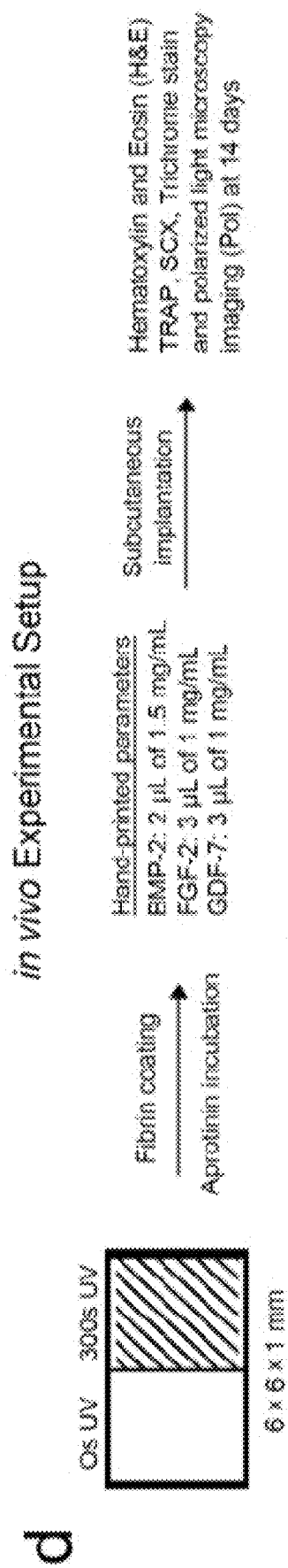
Figure 19E:
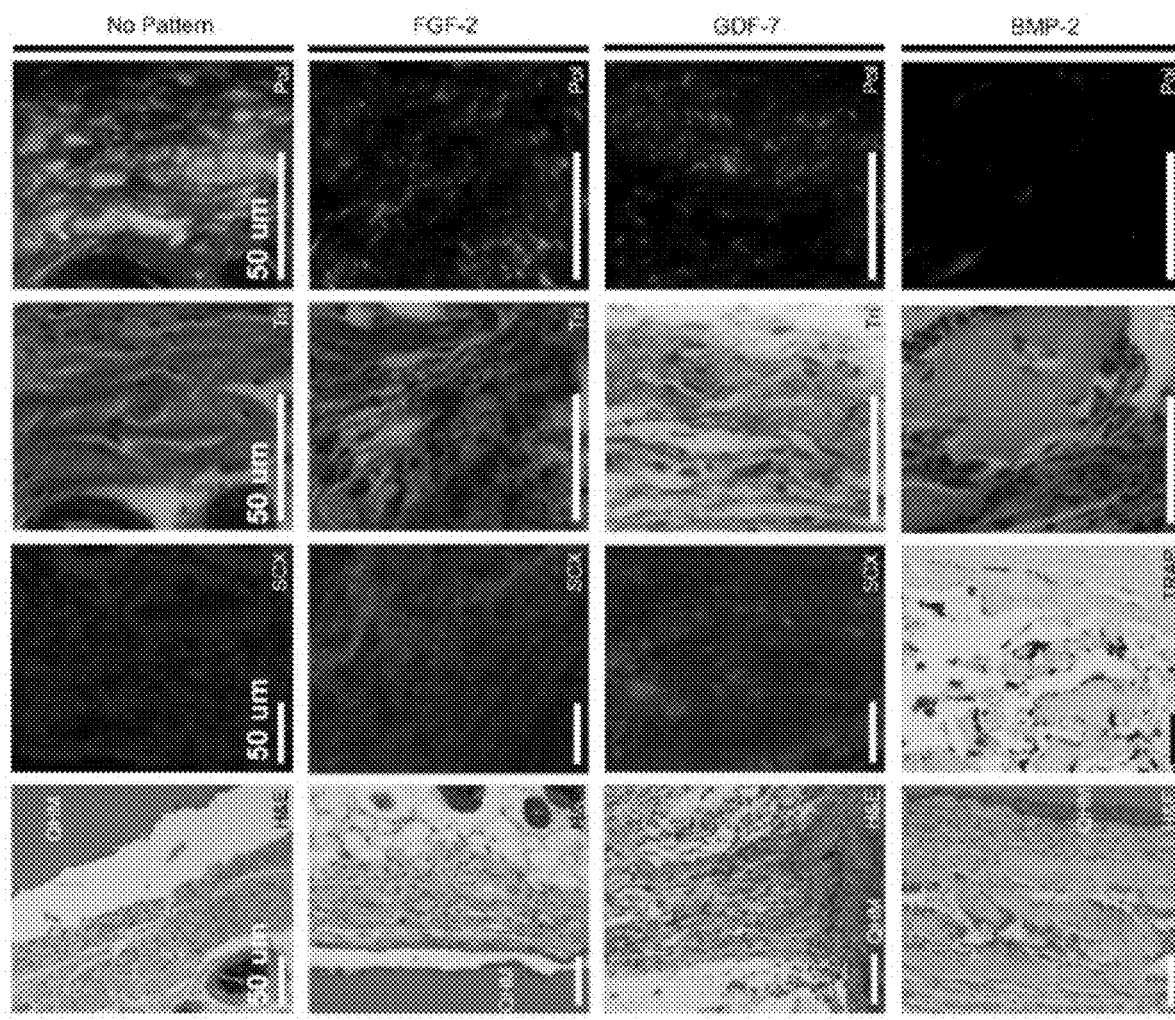
Figure 25:
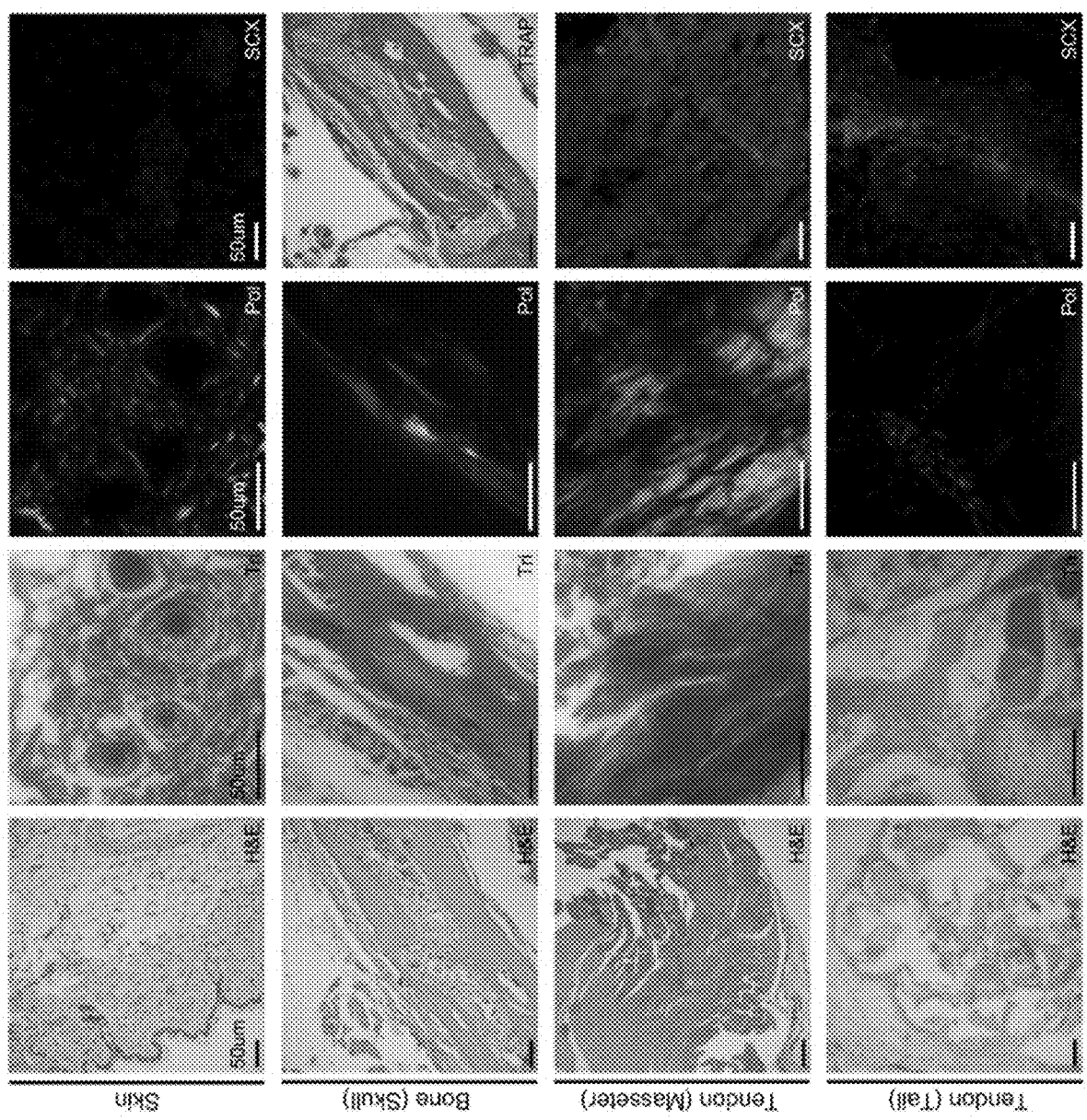
FIG. 25 shows histological staining of mouse bone, tendon and skin tissues. Various histological stains (Hematoxylin and Eosin; H&E, Lillie Modification of Masson's Trichrome; Tri, TRAP and SCX) and imaging modalities (Brightfield and polarized; Pol) were used to examine mouse bone, tendon and skin tissues. Stains as indicated. Trichrome and polarized microscopy images shown were obtained from the same specimen. Scale bars as indicated.

Effect of Growth Factor-Biopatterning on Osteoblast and Tenocyte Differentiation in Fibrin-Coated, QHM Polymers The effect of growth factor-biopatterning on osteoblast and tenocyte differentiation in fibrin-coated QHM polymers was determined in vitro and in mouse subcutaneous implantation studies (FIG. 19A-19E). BMP-2[18,19,29-32] was used as a bone-promoting cue while FGF-2[18,19,36] and Growth and Differentiation Factor-7 (GDF-7)[21,22] were used as tendon-promoting cues (FIG. 19A and FIG. 19D). Prior to growth factor-biopatterning, contact angle measurements and fluorescence-labeled growth factor binding studies determined that QHM polymers were suitable for fibrin coating, printing and growth factor-immobilization (FIG. 20, FIG. 21 and FIGS. 22A-22B). BMP-2 and FGF-2 patterning on fibrin-coated QHM polymers in vitro largely increased C2C12 ALP activity and SCX expression relative to their respective off pattern controls, respectively (FIG. 19B, 19C, Tables 17 and 18). Similarly, increased C3H10T1/2 ALP activity was observed for majority of fibrin-coated QHM polymers on BMP-2 patterns relative to off pattern controls (FIG. 23). The majority of biopatterned growth factors retained their bioactivity in vitro when stored at 4° C. for 3 months (FIG. 24). Mouse subcutaneous implantation of fibrin-coated QHM polymers patterned with bone- and tendon-promoting cues demonstrated biocompatibility as well as formation of bone- and tendon-like tissues relative to non-printed controls, respectively (FIG. 19E and FIG. 25). Mice implanted with QHM polymers showed consistent weight gain and did not exhibit adverse clinical signs or mortality (Data not shown). BMP-2 patterning in vivo resulted in cells positive for the osteoclastic marker tartrate-resistant acid phosphatase (TRAP) and collagen-rich structures (Trichrome and Hematoxylin & Eosin staining) that contained abundant bone marrow, which were reminiscent of immature bone. FGF-2 and GDF-7 patterning in vivo resulted in cells that highly expressed SCX as well as birefringent (Polarized light microscopy), wavy and crimped collagen fibers (Trichrome and Hematoxylin & Eosin staining) reminiscent of immature tendon. As such, growth factor-biopatterned, fibrin-coated QHM polymers were biocompatible and demonstrated spatially controlled osteoblast and tenocyte differentiation in vitro and in vivo.

Figure 20:
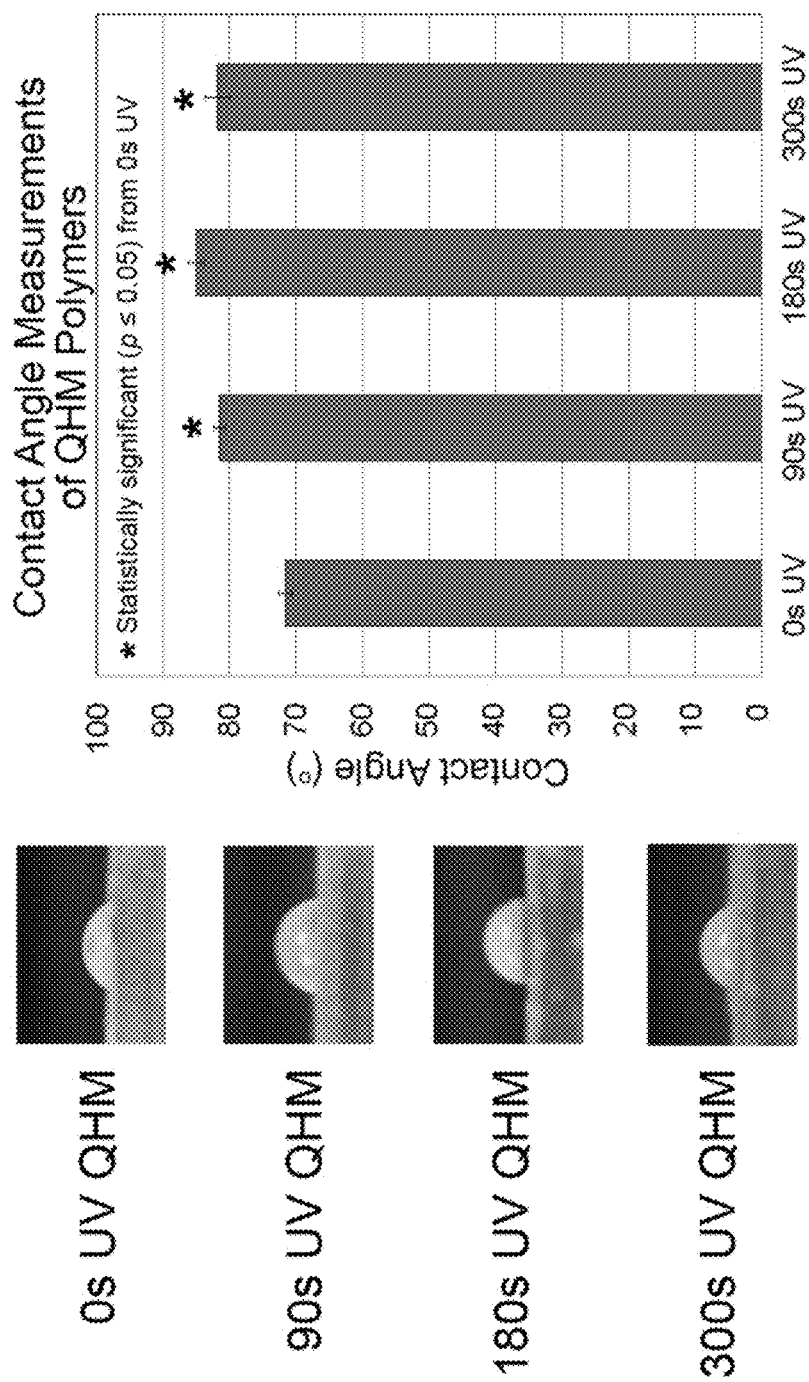
FIG. 20 shows effect of UV-exposure on contact angle of QHM polymers. Representative images and quantification of contact angle measurements are shown (n=6). Error bars indicate standard error of mean. * indicates statistical significance (p≤0.05) relative to 0 s UV QHM polymer.

To determine the wettability of QHM polymer surfaces for subsequent fibrin-coating and growth factor-biopatterning studies, contact angle measurements were performed. 0 s UV, 90 s UV, 180 s UV and 300 s UV QHM polymers had contact angles of 71.7°, 81.5°, 85.0° and 81.8°, respectively (FIG. 20). The contact angle of QHM polymers initially increased with UV-exposure ($p<0.001$ for 0 s UV versus 90 s UV, $p<0.001$ for 0 s UV versus 180 s UV and $p<0.001$ for 0 s UV versus 300 s UV) but did not exhibit any further increase thereafter ($p=0.252$ for 90 s UV versus 180 s UV, $p=0.998$ for 90 s UV versus 300 s UV and $p=0.332$ for 180 s UV versus 300 s UV). With contact angles smaller than 90°, QHM polymer surfaces had high wettability that were suitable[51] for fibrin-coating and growth factor-biopatterning.

To assess the extent of fibrin-coating on QHM polymers, fluorescently-labeled fibrinogen was used. Fibrin-coated QHM polymers exhibited increased Alexa Fluor® fluorescence compared to uncoated QHM polymer controls (FIG. 21). This indicated that QHM polymers were successfully coated with fibrin.

To determine the persistence of biopatterned growth factors on fibrin-coated QHM polymers, growth factor binding studies were performed using fluorescently-labeled BMP-2 and FGF-2. For BMP-2 that was handprinted at a concentration of 500 μg/mL, the amount of growth factor fluorescence signal remaining after 3 PBS washes on 0 s UV, 90 s UV, 180 s UV and 300 s UV QHM polymers were 0.26, 0.17, 0.26 and 0.30 respectively (FIG. 22A). No difference in fluorescence signal intensity was observed between the $1^{st}$ and $3^{rd}$ PBS wash within each respective group ($p=0.683$ for 0 s UV $1^{st}$ wash versus 0 s UV $3^{rd}$ wash, $p=0.504$ for 90 s UV $1^{st}$ wash versus 90 s UV $3^{rd}$ wash, $p=0.998$ for 180 s UV $1^{st}$ wash versus 180 s UV $3^{rd}$ wash and $p=0.994$ for 300 s UV $1^{st}$ wash versus 300 s UV $3^{rd}$ wash). For BMP-2 that was handprinted at a concentration of 250 μg/mL, the amount of growth factor fluorescence signal remaining after 3 PBS washes on 0 s UV, 90 s UV, 180 s UV and 300 s UV QHM polymers were 0.74, 0.25, 0.15 and 0.22 respectively (FIG. 22A). No difference in fluorescence signal intensity was observed between the $1^{st}$ and $3^{rd}$ PBS wash within each respective group ($p=0.669$ for 0 s UV $1^{st}$ wash versus 0 s UV $3^{rd}$ wash, $p>0.999$ for 90 s UV $1^{st}$ wash versus 90 s UV $3^{rd}$ wash, $p=0.696$ for 180 s UV $1^{st}$ wash versus 180 s UV $3^{rd}$ wash and $p=0.995$ for 300 s UV $1^{st}$ wash versus 300 s UV $3^{rd}$ wash).

For FGF-2 that was handprinted at a concentration of 1000 μg/mL, the amount of growth factor fluorescence signal remaining after 3 PBS washes on 0 s UV, 90 s UV, 180 s UV and 300 s UV QHM polymers were 0.58, 0.42, 0.93 and 0.87 respectively (FIG. 22B). No difference in fluorescence signal intensity was observed between the $1^{st}$ and $3^{rd}$ PBS wash within each respective group ($p>0.999$ for 0 s UV $1^{st}$ wash versus 0 s UV $3^{rd}$ wash, $p>0.999$ for 90 s UV $1^{st}$ wash versus 90 s UV $3^{rd}$ wash, $p=0.999$ for 180 s UV $1^{st}$ wash versus 180 s UV $3^{rd}$ wash and $p>0.999$ for 300 s UV $1^{st}$ wash versus 300 s UV $3^{rd}$ wash). For FGF-2 that was handprinted at a concentration of 500 μg/mL, the amount of growth factor fluorescence signal remaining after 3 PBS washes on 0 s UV, 90 s UV, 180 s UV and 300 s UV QHM polymers were 0.59, 0.60, 0.65 and 0.91 respectively (FIG. 22B). No difference in fluorescence signal intensity was observed between the $1^{st}$ and $3^{rd}$ PBS wash within each respective group ($p>0.999$ for 0 s UV $1^{st}$ wash versus 0 s UV $3^{rd}$ wash, $p>0.999$ for 90 s UV $1^{st}$ wash versus 90 s UV $3^{rd}$ wash, $p=0.909$ for 180 s UV $1^{st}$ wash versus 180 s UV $3^{rd}$ wash and $p>0.999$ for 300 s UV $1^{st}$ wash versus 300 s UV $3^{rd}$ wash). For FGF-2 that was handprinted at a concentration of 100 μg/mL, the amount of growth factor fluorescence signal remaining after 3 PBS washes on 0 s UV, 90 s UV, 180 s UV and 300 s UV QHM polymers were 0.54, 0.55, 0.38 and 0.33 respectively (FIG. 22B). No difference in fluorescence signal intensity was observed between the $1^{st}$ and $3^{rd}$ PBS wash within each respective group ($p>0.999$ for 0 s UV $1^{st}$ wash versus 0 s UV $3^{rd}$ wash, $p>0.999$ for 90 s UV $1^{st}$ wash versus 90 s UV $3^{rd}$ wash, $p>0.999$ for 180 s UV $1^{st}$ wash versus 180 s UV $3^{rd}$ wash and $p>0.999$ for 300 s UV $1^{st}$ wash versus 300 s UV $3^{rd}$ wash). Thus, these data demonstrated that BMP-2 and FGF-2 could be persistently immobilized on fibrin-coated QHM polymers.

To determine the effect of growth factor-biopatterning on osteoblast differentiation, C3H10T1/2 ALP activity was assessed on BMP-2-biopatterned, fibrin-coated QHM polymers. Increased C3H10T1/2 ALP activity was observed for majority of fibrin-coated QHM polymers (90 s UV, 180 s UV and 300 s UV) on BMP-2 patterns relative to off pattern controls but not for 0 s UV QHM polymer (FIG. 23). As such, fibrin-coated QHM polymers biopatterned with BMP-2 spatially controlled C3H10T1/2 osteoblast differentiation.

To determine growth factor bioactivity following long-term storage at 4° C., C2C12 ALP activity was assessed on BMP-2-biopatterned, fibrin-coated QHM polymers 3 months post-printing. Increased C2C12 ALP activity was observed for fibrin-coated QHM polymers on BMP-2 patterns relative to off pattern controls (On pattern 0 s UV QHM polymer: 57.08, On pattern 90 s UV QHM polymer: 66.74, On pattern 180 s UV QHM polymer: 58.90, On pattern 300 s UV QHM polymer: 12.82, Off pattern 0 s UV QHM polymer: 8.94, Off pattern 90 s UV QHM polymer: 4.19, Off pattern 180 s UV QHM polymer: 3.91 and Off pattern 300 s UV QHM polymer: 4.17; $p<0.001$ for 0 s UV off pattern versus 0 s UV on pattern, $p<0.001$ for 90 s UV off pattern versus 90 s UV on pattern, $p<0.001$ for 180 s UV off pattern versus 180 s UV on pattern, $p=0.959$ for 300 s UV off pattern versus 300 s UV on pattern; FIG. 24). The weaker ALP activity observed on 300 s UV QHM BMP-2 patterns may have been attributed to loss of bioactivity following sample transport, long-term storage, a bad printing run resulting in poor growth factor-biopatterning or a combination of these factors. As such, majority of growth factor-biopatterned QHM polymers retained their bioactivity 3 months post-printing.

To assist in determining whether growth factor-biopatterned, fibrin-coated QHM polymers induced bone- and tendon-like formation in a mouse subcutaneous model, bone, tendon and skin tissues were harvested from mice and subjected to various histological staining and imaging modalities (FIG. 25). Bone tissues exhibited distinct appearance and morphology under H&E as well as Trichrome staining including presence of lamellar bone, bone marrow and cells that were positive for the osteoclast marker tartrate-resistant acid phosphatase (TRAP). Tendon tissues exhibited distinct appearance and morphology under H&E as well as Trichrome staining including presence of crimped, aligned collagen fibers and cells that had highly expressed the tenocyte marker SCX. Skin tissues exhibited distinct appearance and morphology under H&E as well as Trichrome staining including presence of hair follicles and crosshatched collagen fibers. Although these tissues were collagen-rich, bone, tendon and skin tissues possessed lamellar, crimped and crosshatched appearances, respectively, under polarized light (Pol). Together, these control tissues served as a reference for determining the formation of ectopic bone- and tendon-like tissues in mouse subcutaneous implantation studies.

Thus, QHM polymers degraded slowly and their degradation products exhibited little-to-no cytotoxicity.

To determine if QHM polymer could be UV-patterned at physiologically-relevant length scales, QHM polymer was UV-exposed for 300 s under a photomask. This resulted in alternating regions of 0 s and 300 s UV-exposed QHM polymer (similar to the photomask pattern), each measuring approximately 250 µm and 500 µm in width, respectively (FIG. 27). As such, QHM polymer could potentially be fabricated with bone- and tendon-like properties at physiologically-relevant length scales.

TABLE 17

P values comparing C2C12 ALP activity on QHM polymers (BMP-2 patterns versus off pattern controls) at 6 days.

| Group | Group | P value |
|---|---|---|
| Off pattern 0 s UV QHM polymer | On pattern 0 UV QHM polymer | 0.009 |
| Off pattern 90 s UV QHM polymer | On pattern 90 UV QHM polymer | 0.009 |
| Off pattern 180 s UV QHM polymer | On pattern 180 UV QHM polymer | 0.051 |
| Off pattern 300 s UV QHM polymer | On pattern 300 UV QHM polymer | 0.005 |

TABLE 18

P values comparing C2C12 SCX expression on QHM polymers (FGF-2 patterns versus off pattern controls) at 3 days.

| Group | Group | P value |
|---|---|---|
| Off pattern 0 s UV QHM polymer | On pattern 0 UV QHM polymer | 0.000 |
| Off pattern 90 s UV QHM polymer | On pattern 90 UV QHM polymer | 0.000 |
| Off pattern 180 s UV QHM polymer | On pattern 180 UV QHM polymer | 0.000 |
| Off pattern 300 s UV QHM polymer | On pattern 300 UV QHM polymer | 0.004 |

Fabrication of Mechanically-Graded, Hybrid Suture Anchor-Tendon Graft

Figures 26A, 26B:
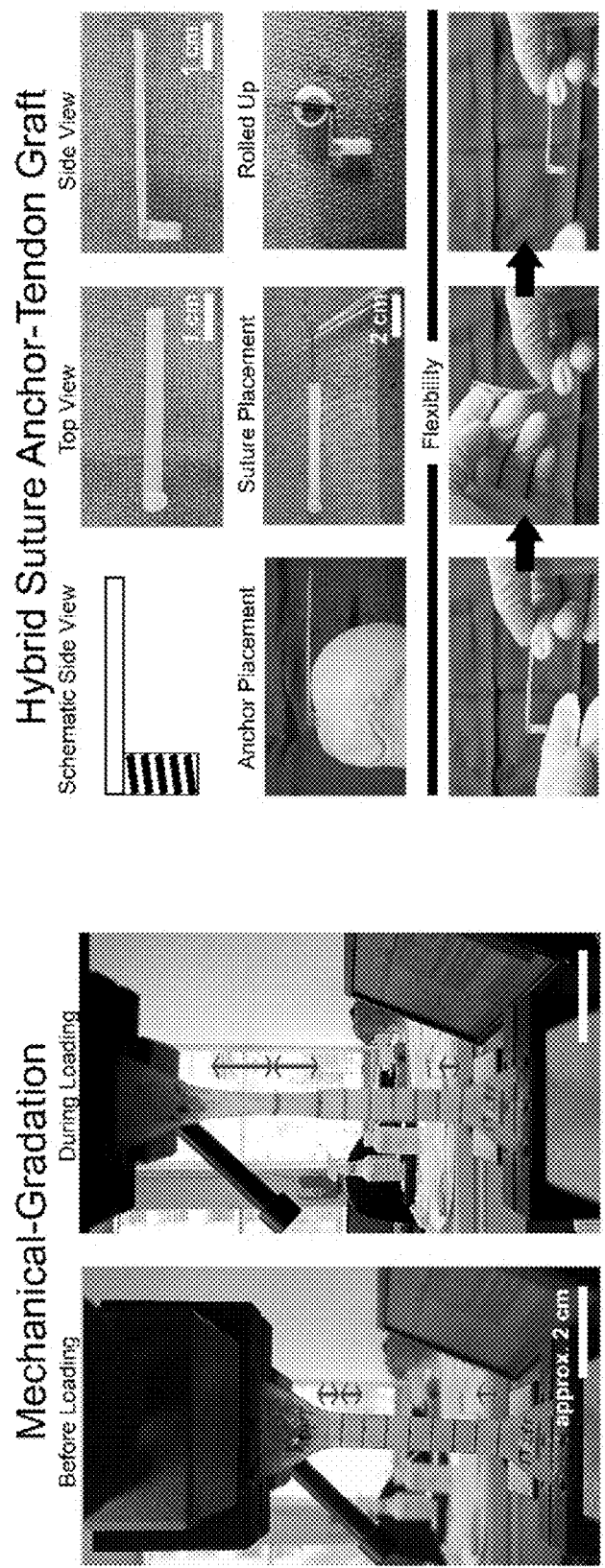
FIGS. 26A-26H show fabrication of hybrid suture anchor-tendon graft and degradation studies of QHM polymers.

To facilitate envisioned clinical translation, a continuous bone-tendon graft was fabricated. QHM polymers could be mechanically-graded (FIG. 26A), sutured and anchored to faux bone when fashioned as a hybrid suture anchor-tendon graft (FIG. 26B). Physiologically-relevant mechanical-gradation was exemplified by fabrication of alternating regions of 0 s and 300 s UV QHM polymers (FIG. 27).

Effect of UV-Exposure on the Degradation of QHM Polymers

Figures 26C, 26D:
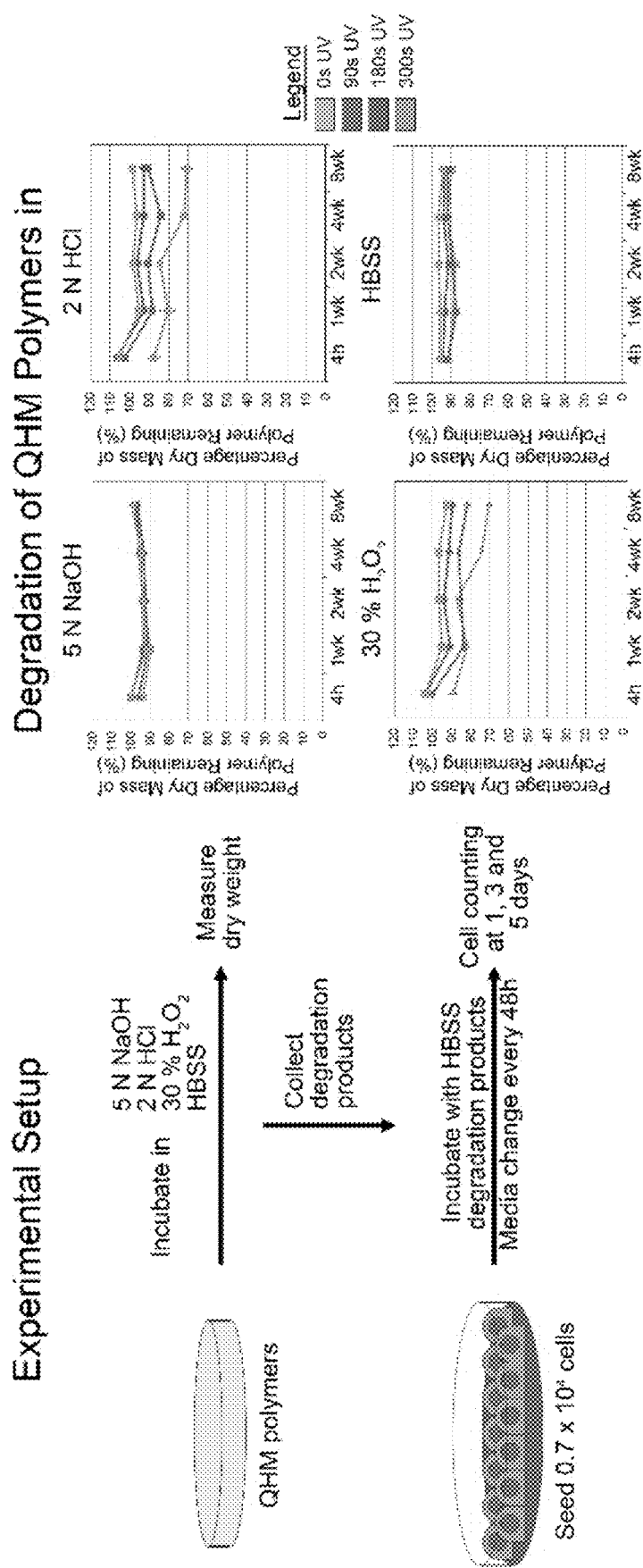
Figures 26E, 26F:
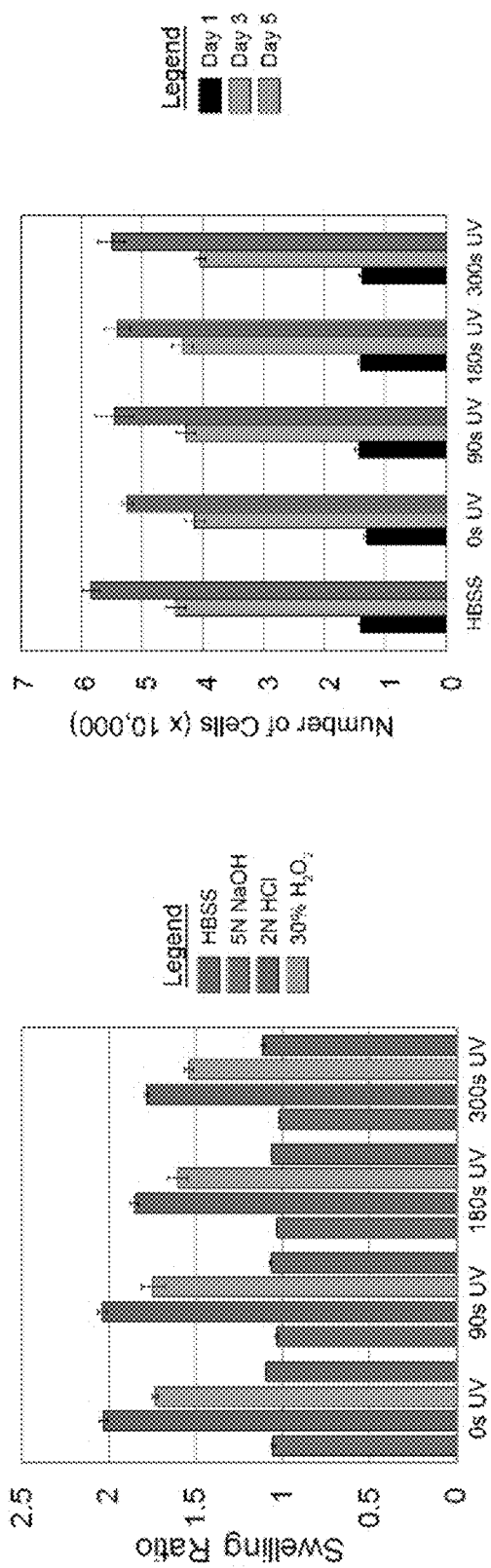
Figure 26G:
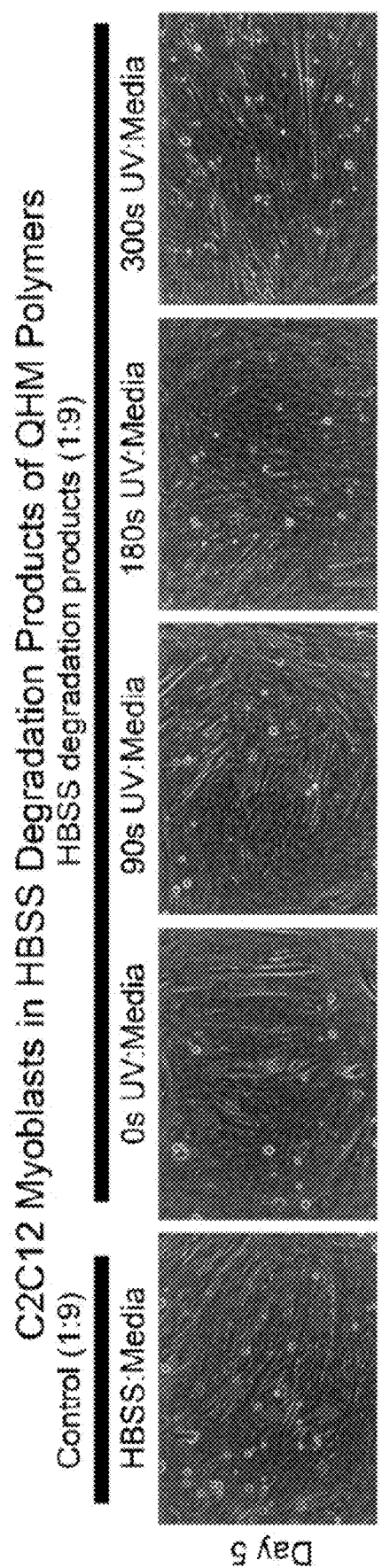
Figure 26H:
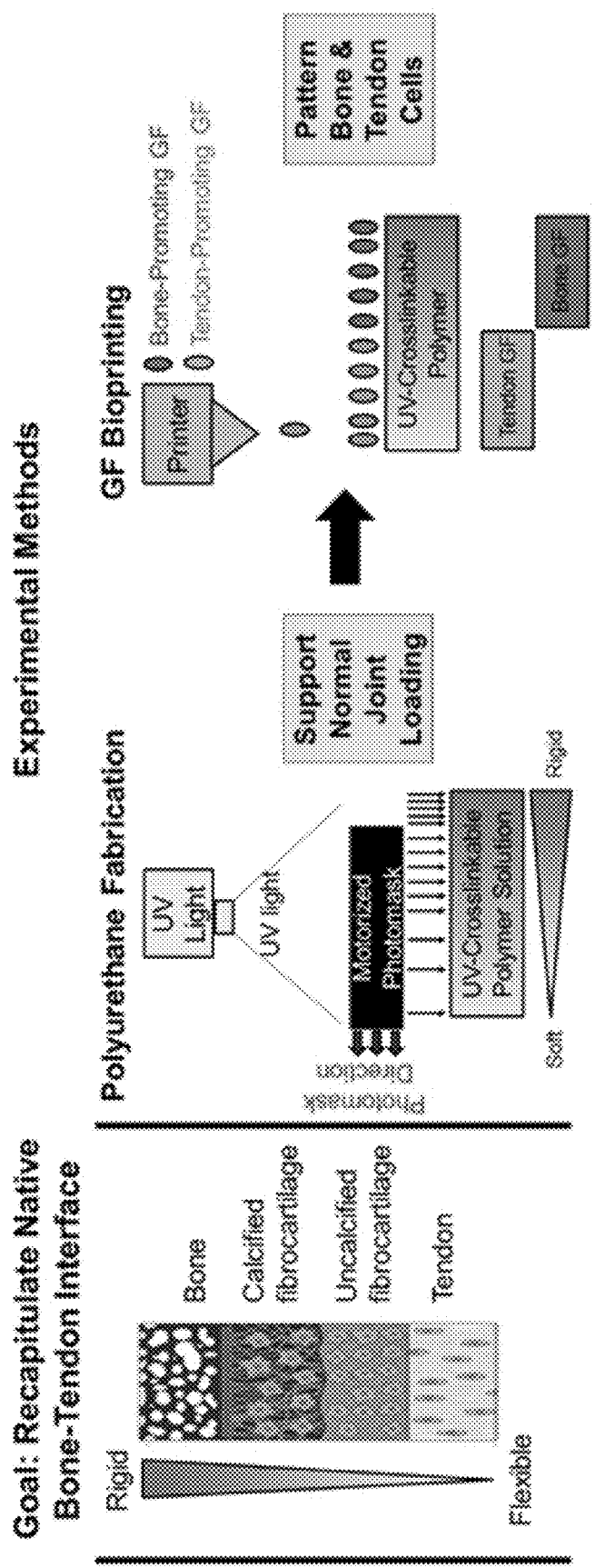

To determine the integrity of QHM polymers under simulated body conditions including chronic wound environments, foreign body reaction to implanted materials and normal physiological conditions, degradation studies were performed. QHM polymer samples were incubated under alkaline (5 N NaOH), acidic (2 N HCl), oxidizing (30% $H_2O_2$) and aqueous (Hank's Buffered Salt Solution; HBSS) conditions for 8 weeks and their mass (dry weight) was recorded (FIG. 26C). Under alkaline, acidic, oxidizing and aqueous conditions, QHM polymers exhibited little-to-no mass loss, 5-30% mass loss, 10-30% mass loss and 5-10% mass loss after 8 weeks, respectively (FIG. 26D). QHM polymers exhibited little-to-no swelling under alkaline and aqueous conditions whereas swelling ratios between 1.5 and 2.0 were observed under acidic and oxidizing conditions (FIG. 26E). C2C12 cells cultured in 8 week HBSS degradation products (diluted 1:9) proliferated similarly to control (FIG. 26F and Table 19) and exhibited myogenic differentiation (FIG. 26G), indicating unperturbed cell behavior.

TABLE 19

P values comparing C2C12 cell numbers cultured in the presence of DMEM media containing degradation products at 5 days.

| Group | Group | P value |
|---|---|---|
| Day 5 HBSS | Day 5 0 s UV QHM polymer | 0.259 |
| Day 5 HBSS | Day 5 90 s UV QHM polymer | 0.902 |
| Day 5 HBSS | Day 5 180 s UV QHM polymer | 0.756 |
| Day 5 HBSS | Day 5 300 s UV QHM polymer | 0.957 |

Methods

Material Fabrication

N,N,N',N'-Tetrakis(2-Hydroxy-propyl)ethylenediamine (Quadrol or Q; Sigma Aldrich, St. Louis, Mo.), 1,6-Diisocyanatohexane (HDI or H; Sigma Aldrich, St. Louis, Mo.) and methacrylic anhydride (MA or M; Sigma Aldrich, St. Louis, Mo.) were used as received without further purification. Q, H and M were mixed in a 50 mL conical tube at a molar ratio of 1:1.5:0.5, respectively, and subjected to vigorous vortexing for 1 to 2 min. Subsequently, the QHM mixture was degassed in a vacuum desiccating chamber (Bel-Art Products, Wayne, N.J.) using a Welch DuoSeal 1405 vacuum pump (Welch-llmvac, Niles, Ill.) for 0.5 to 1 min and transferred into the appropriate mold(s). The mold (s) were degassed for an additional 20 to 30 min and placed in a custom-made light cabinet (42 cm×22 cm×62 cm) equipped with an OmniCure Series 2000 UV system (Excelitas Technologies Illumination, Fremont, Calif.) and a collimating adapter (Excelitas Technologies Illumination, Fremont, Calif.). Irradiance at the emitting end of the 5 mm OmniCure light guide was adjusted to 7 Watts per cm$^2$ using an OmniCure R2000 radiometer (Excelitas Technologies Illumination, Fremont, Calif.). Molds were positioned 60 cm from the collimating adapter, UV-crosslinked for the indicated durations (0 s, 90 s, 180 s or 300 s) and placed in a pressure pot chamber (Finish Systems, New Berlin, Wis.) at 40 psi under nitrogen atmosphere overnight. The following day, QHM polymer samples were released from their molds, sanded using a Ryobi Belt Sander (80-120 grit; Ryobi Limited, Fuchu-Shi, Japan) and heat-cured between 85° C. to 100° C. for 5 to 6 h in a heating oven (Thermo Fisher Scientific, Waltham, Mass.). Subsequently, QHM polymer samples were washed once in 5 N sodium hydroxide (Ricca Chemical Company, Arlington, Tex.) for 1 h, washed five times in deionized water and air-dried. Specimen dimensions are described below for each study.

Nuclear Magnetic Resonance Spectroscopy (NMR)

$^1$H-NMR was performed using a Varian Inova 300 instrument (Varian Inc., Palo Alto, Calif.) at ambient conditions. Samples of QHM pre-polymer or UV-crosslinked QHM polymer were dissolved overnight at 4° C. in deuterated chloroform (CDCl$_3$; 99.8% deuterated, Sigma Aldrich, St. Louis, Mo.) to obtain maximum solubility. Pure CDCl$_3$ was used as an internal standard. NMR spectra prediction was performed with ChemBioDraw Ultra 13.0 software (CambridgeSoft, Waltham, Mass.). NMR data were analyzed with MestReNova 10.0 NMR software (Mestrelab Research, Escondido, Calif.).

Fourier Transformed Infrared Spectroscopy (FTIR)

FTIR was performed using a Bruker Vertex 70 spectrometer (Bruker Optics Inc., Billerica, Mass.) and analyzed with OPUS optical spectroscopy software (Bruker Optics Inc., Billerica, Mass.). For Q/H pre-polymer solutions, Q and H were mixed at a molar ratio of 1:2, respectively. For Q/M pre-polymer solutions, Q and M were mixed at a molar ratio of 1:4, respectively. For H/M pre-polymer solutions, H and M were mixed at a molar ratio of 1:1, respectively. For QHM pre-polymer solutions, Q, H and M were mixed at a molar ratio of 1:1.5:0.5, respectively. Pre-polymer solutions were mixed vigorously for 5-10 min and samples were placed in the holder directly in the IR laser beam. Degassing and longer pre-polymer reaction times were not attempted to avoid polymer solidification within the sample holder. All spectra were recorded (40 averaged scans, 800-4000 cm$^{-1}$) at a resolution of 4 cm$^{-1}$. Spectra were baseline-corrected and smoothed in the OPUS spectroscopy software.

Mechanical Testing

QHM polymer samples were mechanically tested under dry conditions at room temperature following the guidelines in the American Society for Testing and Materials (ASTM) methods D638-10 (Tensile properties of plastics), D695-10 (Compressive properties of rigid plastics) and D7791-12 (Uniaxial fatigue properties of plastics). Although tendons are predominantly subjected to tensile stress, there are locations where tendons experience compressive stresses, most notably where they wrap around bony or fibrous pulleys and at the bone-tendon interface. Consequently, both tension and compressive tests were performed on the QHM polymer samples. Tensile testing samples were fabricated as dog bone-shaped specimens with an overall length of 115 mm with the narrow region measuring 3 mm (thickness)×7.5 mm (width)×33 mm (length). Compression testing samples were fabricated as rectangular specimens measuring 25 mm (height)×6 mm (width)×8 mm (length). The average cross sectional area was determined from three locations along the specimen length using digital calipers (Digimatic IP67 Coolant-Proof Caliper; Mitutoyo American Corporation, Aurora, Ill.). A Model 5944 test system equipped with a 2 kN load cell (Instron Corp., Norwood, Mass.) was used for tensile testing whereas an ElectroPuls E10000 test system (Instron Corp., Norwood, Mass.) was used for compressive, creep and cyclic testing. Compression tests were performed using a 10 kN load cell whereas creep and cyclic tests incorporated a 250 N load cell. Strain was determined using an extensometer (Model: 3442-0064-050-ST, Gauge length: 16.3 mm, Epsilon Technology Corp, Jackson, Wyo.).

For tensile testing, QHM polymer samples were preloaded to 5 N and subsequently uniaxially loaded at a rate of 0.65 mm per second until failure. This displacement rate corresponds to a strain rate of approximately 1% strain per second during loading in the initial region of the linear response. For QHM polymer samples that did not fail (break) before 50% strain, the extensometer was removed and testing was continued until failure. Tensile strength at yield or break was defined as tensile stress at which QHM polymer samples yielded (Slope where the stress-strain curve equals zero) or failed, respectively. Tensile strength at break was reported for samples that did not yield. Tensile modulus was defined as the initial linear slope of the stress-strain curve and calculated from 0% to 1% strain. Tensile strain at yield or break was defined as the strain at which QHM polymer samples yielded or failed, respectively. Tensile strain at break were reported for samples that did not yield. Failure strain for QHM polymer samples that did not break before 50% strain was calculated using the machine readout of grip separation.

For compressive testing, QHM polymer samples were preloaded to 10 N and then uniaxially loaded at a strain rate of 1% per second until failure. Compressive strength was defined as the maximum compressive stress achieved during the test as QHM polymer samples failed by buckling. Compressive modulus was defined as the initial linear slope of the stress-strain curve and calculated from 1% to 2% strain. Compressive strain at maximum stress was defined as the strain at which maximum compressive stress was achieved during the test.

For static creep tensile testing, QHM polymer samples were loaded in tension to 3 MPa (which was estimated[39, 40, 46] to be 75% of the maximum stress generated by supraspinatus muscle) for 30 min. Specimens were then rapidly unloaded to 0 MPa and recovery was monitored for 10 min. Static creep was defined as the difference in strain between the initial and final time points during the 30 min hold at 3 MPa. Creep recovery was defined as the difference in strain after the 30 min hold at 3 MPa and the 10 min recovery period at 0 MPa. Creep rate was determined from the linear slope of the strain-time curve between 10 min and 30 min loading at 3 MPa.

For cyclic tensile testing, QHM polymer samples were loaded from 0.2 to 3 MPa for 10,000 cycles at 1 Hz. The lower loading limit of 0.2 MPa was selected as an estimate of the passive tension generated by the supraspinatus muscle[45]. The dynamic, storage and loss modulus as well as tan δ were calculated at various time points during cyclic loading using WaveMatrix software (Instron Corp., Norwood, Mass.). The dynamic modulus was defined as the ratio of the stress range to strain range of the hysteresis loop for a given loading cycle. The storage modulus was defined as the dynamic modulus multiplied by the cosine of the loss angle. The loss modulus was defined as the dynamic modulus multiplied by the sine of the loss angle. Tan δ was defined as the ratio of the loss modulus to the storage modulus. Cyclic creep was defined as the difference in strain at 3 MPa between cycle 10 and cycle 10,000.

Differential Scanning Calorimetry (DSC)

DSC was performed using a Q100 instrument (TA Instruments, New Castle, Del.) under nitrogen atmosphere and analyzed with Universal Analysis software (TA Instruments, New Castle, Del.). QHM polymer samples were crushed with a hammer to obtain samples weighing 10-20 mg and sealed in an aluminum pan. QHM polymer samples were subjected to cool-heat-cool-heat treatment over a temperature range of −40° C. to 100° C. The first run started from room temperature cooling to −40° C., holding isothermally for 5 min, followed by heating from −40° C. to 100° C. and holding isothermally at 100° C. for 5 min. The second run started from 100° C. cooling to −40° C., holding isothermally for 5 min, followed by heating from −40° C. to 100° C. Heating or cooling was performed at a rate of 20° C. $min^{-1}$. The glass transition temperature ($T_g$) was measured at the midpoint of the transition process from the second run.

Finite Element Analysis (FEA)

Linear static FEA of a mechanically-graded specimen containing a single bonded interface was performed using SolidWorks Simulation (Dassault Systemes, Waltham, Mass.). While simplistic, a single interface was simulated since gradients can be approximated by a continuous series of discrete intervals. Moreover, this setup facilitated ease of comparison with photoelastic tensile testing. Due to symmetry, a quarter model was developed with similar geometry to QHM polymer samples used for tensile testing. The dimensions were 10×3×1.5 mm (overall length×half-width× half-thickness). The 10 mm overall length was selected to analyze the loading distribution in the vicinity of the interface. Roller boundary conditions were modeled along the mid-planes of the model (right and back faces). An additional roller boundary condition was applied to the bottom face of the model to prevent vertical (y axis) displacement. A uniform tensile stress (10 MPa) was applied to the model's top face to simulate a physiologically-relevant load close to the tensile strength of supraspinatus tendon[39].

The model mesh was created using second-order tetrahedral elements varying in size from 0.125 mm away from the interface down to 0.005 mm along the periphery of the interface. Due to the stress singularity at the interface, convergence of the model was not reached with further mesh refinement. The elastic moduli and Poisson's ratio were defined using linear elastic isotropic material models. A Poisson's ratio of 0.3 and an elastic modulus of 0.5 GPa were used for the top rectangular cuboid while a Poisson's ratio of 0.3 and elastic moduli between 0.5 GPa to 10 GPa were used for the bottom rectangular cuboid to study the effect of different elastic moduli on non-uniform, mechanically-graded specimens. The magnitude and von Mises stress distribution were determined for the different combinations of elastic moduli and Poisson's ratio.

Photoelasticity Tensile Testing

Figure 8:
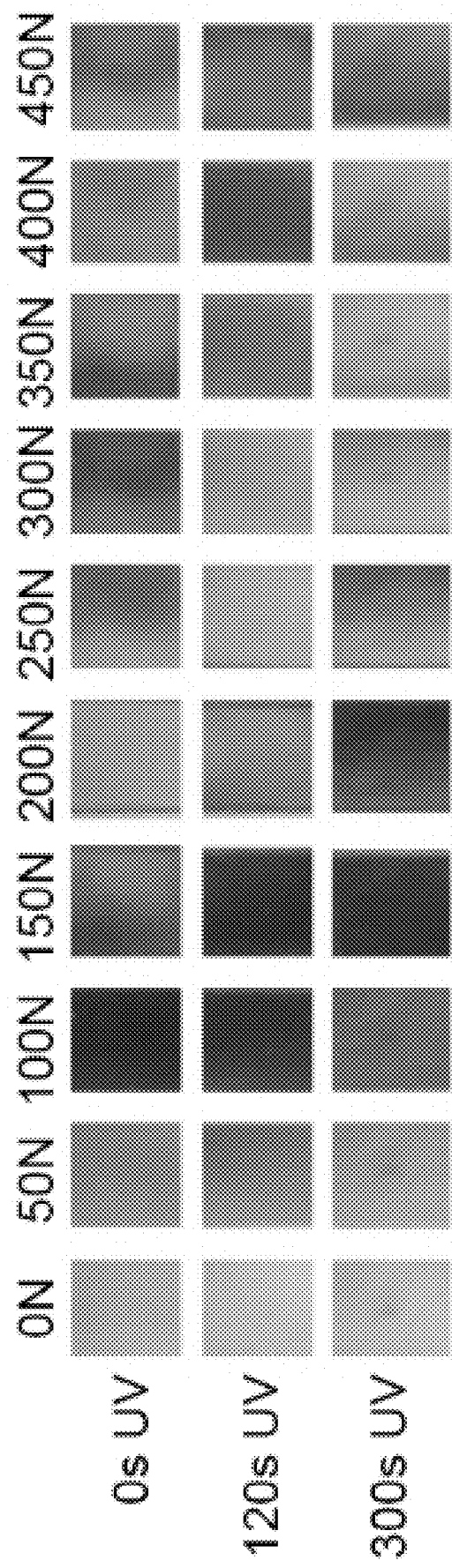
FIG. 8 shows photoelastic tensile color inference chart. Top row shows 0 s UV QHM polymer. Middle row shows 120 s UV QHM polymer. Bottom row shows 300 s UV QHM polymer (n=3).

Photoelastic tensile testing was performed as previously described with minor modifications[47]. Specimens (2.2 cm×12.7 cm×0.6 cm) consisting of either uniform, non-graded QHM polymer samples (90 s UV, 120 s UV or 300 s UV) or non-uniform, mechanically-graded QHM polymer samples containing a single interface (90 s:120 s UV or 90 s:300 s UV) were fabricated. These dimensions were used to produce a wide QHM polymer sample to increase reproducibility by reducing the impact of a curved meniscus at the edges of the mold. While simplistic, a single interface was tested since gradients can be approximated by a continuous series of discrete intervals. Also, this setup facilitated ease of comparison with FEA simulations. Non-uniform, mechanically-graded QHM polymer samples were fabricated by varying UV exposure to different halves of the same specimen. The average cross sectional area of QHM polymer samples was determined from three locations along the specimen gauge length using digital calipers. Photoelastic tensile testing was performed on a custom setup consisting of a Model 5944 test system (Instron Corp., Norwood Mass.) with the QHM polymer sample mounted in-between two left-handed, circularly polarized films (Edmund Optics Inc., Barrington, N.J.). The films were oriented such that their polarizing axes were approximately 90 degrees relative to each other. The setup was backlit with a light box (Universal Medical Inc.,Norwood, Mass.) and images of the photoelastic tensile testing were acquired using a Canon PowerShot S95 camera (Canon Inc., Melville, N.Y.). Uniform, non-graded QHM polymer samples were uniaxially loaded at constant loads (0 to 500 N at intervals of 50 N) and used to construct a tensile-color interference chart (FIG. 8). This chart quantified stress distributions in non-uniform, mechanically-graded QHM polymer samples with gradually-graded (90:120 s UV) and steeply-graded (90 s:300 s UV) interfaces. The 0 s UV QHM polymers were not used in these experiments as their high flexibility resulted in necking deformations at the interface of mechanically-graded samples, posing difficulties in obtaining accurate stress and strain measurements due to the local decrease in cross sectional area.

Porosity Measurements

Mercury intrusion porosity measurements was performed on QHM polymer samples (circular discs approximately 1 cm in diameter) by Micromeritics analytical services (Micromeritics, Norcross, Ga.).

Surface Profile Measurements

Surface profiling was performed using a Veeco Dektak 150 Profilometer (Veeca Instruments Inc., Plainview, N.Y.) equipped with a 25 µm diameter stylus tip. Line profiles (1 mm) were obtained at a resolution of 28 nm per QHM polymer sample (circular discs approximately 1 cm in diameter).

Contact Angle Measurements

Contact angle measurements were performed by pipetting 1 µL of deionized water onto QHM polymer samples (circular discs approximately 1 cm in diameter) followed by imaging using a Canon PowerShot S95 camera at room temperature. Contact angle measurements were determined using ImageJ software (http://imagej.nih.gov/ij/, National Institutes of Health, Bethesda, Md.).

Fibrin Coating

QHM polymer samples were double-coated with fibrin as previously described with minor modifications[18,19,29-32,48-50]. Briefly, QHM polymer samples were incubated with 1 mg/mL fibrinogen (Enzyme Research Laboratories, South Bend, Ind.) in 10 mM sodium phosphate, pH 7.4 (Thermo Fisher Scientific, Waltham, Mass.) overnight. The following day, QHM polymer samples were washed with phosphate-buffered saline (PBS; Life Technologies, Carlsbad, Calif.) to remove unbound fibrinogen and fibrin-coated via incubation with 4 U/mL thrombin (Enzyme Research Laboratories, South Bend, Ind.) for 2 h at 37° C. Following this, QHM polymer samples were washed with three times in PBS and three times in deionized water. Subsequently, the fibrin coating step was repeated. Fibrin-coated QHM polymer samples were air-dried in a laminar flow hood and stored at 4° C. prior to use. Fibrin-coating was monitored using Alexa Fluor®-conjugated fibrinogen (Life Technologies, Carlsbad, Calif.) on QHM polymer samples (circular discs approximately 1 cm in diameter). Fluorescence images were acquired on an inverted Zeiss AxioObserver Z1 microscope (Carl Zeiss Microimaging, Thornwood, N.Y.) equipped with an X-Cite® Series 120Q metal halide lamp, appropriate filters and an AxioCam MRm camera (Carl Zeiss Microimaging, Thornwood, N.Y.). The thickness of the fibrin films was previously estimated to be approximately 20 nm[19,48].

Growth Factor Preparation and Use

Recombinant human bone morphogenetic protein-2 (BMP-2; Medtronic, Minneapolis, Minn.), fibroblast growth factor-2 (FGF-2; Peprotech, Rockyhill, N.J.) and growth and differentiation factor-7 (GDF-7; Sino Biological Inc., Beijing, China) were reconstituted according to manufacturer's instructions to 1 to 2 mg/mL, aliquoted and stored at −80° C. Prior to use, growth factors were freshly diluted to the desired concentration in 10 mM sodium phosphate, pH 7.4.

Growth Factor Printing

Growth factor printing was performed as previously described[18,19,29-32,48]. Briefly, growth factors were freshly diluted to the desired concentration in 10 mM sodium phosphate, pH 7.4. To ensure sterile conditions, the printhead was washed with 70% ethanol and sterile deionized water. To minimize non-specific growth factor binding to the walls of the inkjet, the printhead was incubated with 100 μg/mL bovine serum albumin (BSA; Santa Cruz Biotechnology Inc, Santa Cruz, Calif.) for 5 min and washed with 10 mM sodium phosphate buffer, pH 7.4. Subsequently, the growth factor was loaded into the printhead, and biopatterned onto fibrin-coated QHM polymer samples. The concentration of biopatterned growth factors can be modulated by overprinting, which was achieved by varying the number of times a growth factor was deposited in the same (x,y) location. Alternatively, fibrin-coated QHM polymer samples were handprinted by manually depositing 0.5-3 μL of growth factor using a micropipette. After printing, fibrin-coated QHM polymer samples were allowed to dry and stored at 4° C. For in vitro studies, growth factor-biopatterned, fibrin-coated QHM polymer samples were incubated in PBS for 5 min followed by serum-free DMEM with 1% penicillin-streptomycin (PS; Life Technologies, Carlsbad, Calif.) overnight at 37° C. to wash off unbound growth factor prior to cell seeding. For in vivo studies, fibrin-coated QHM polymer samples were further incubated with 1 μg/mL aprotinin overnight (Sigma Aldrich, St. Louis, Mo.) after fibrin coating, allowed to dry and stored at 4° C. prior to growth factor-printing.

Growth Factor Immobilization

The surface concentration of growth factor present on fibrin-coated QHM polymer samples (circular discs approximately 1 cm in diameter) were measured using fluorescently-labeled growth factors as previously described with minor modifications[29,48,49]. Where necessary, buffer exchange was performed using Amicon Ultra Centrifugal Filters with a 10,000 molecular weight cut-off (Millipore Corporation, Billerica, Mass.). BMP-2 and FGF-2 were fluorescently-labeled with Amine-Reactive Dylight 650 NETS-ester Conjugation kit (Pierce Biotechnology Inc., Rockford, Ill.) according to the manufacturer's instructions. Unbound dye was removed using dye removal columns (Pierce Biotechnology Inc., Rockford, Ill.). The degree of labeling was monitored using an Eppendorf Biophotometer spectrophotometer (Eppendorf, Hamburg, Germany). To perform desorption measurements, 0.5 μL of growth factors at various concentrations were handprinted onto fibrin-coated QHM polymer samples, allowed to dry for 1 h at 37° C. and fluorescently-imaged prior to incubation in PBS for 5 min. Subsequently, PBS was aspirated and fibrin-coated QHM polymer samples were fluorescently-imaged. This step was repeated for a total of three times to monitor growth factor desorption from fibrin-coated QHM polymer samples in between successive PBS washes. Fluorescence images were acquired on an inverted Zeiss AxioObserver Z1 microscope equipped with an X-Cite® Series 120Q metal halide lamp, appropriate filters and an AxioCam MRm camera. Fluorescence images were quantified by calculating the average pixel intensity in Adobe Photoshop 7.0 (Adobe Systems, San Jose, Calif.).

Cell Culture

Multi-potent mouse C3H10T1/2 fibroblasts (ATTC, Manassas, Va.) and mouse C2C12 myoblasts (ATTC, Manassas, Va.) were grown in Dulbecco's Modified Eagle's Media (DMEM; Life Technologies, Carlsbad, Calif.), 10% fetal bovine serum (FBS; Life Technologies, Carlsbad, Calif.) and 1% PS. All cells were kept at 37° C., 5% $CO_2$ in a humidified incubator. These cells were used as they serve as surrogate models of mesenchymal and muscle-derived stem cells, which are practical sources for cell-based regenerative medicine. Hoechst staining (Anaspec, Fremont, Calif.) determined that cell cultures were free of mycoplasma contamination.

Cell Attachment

Cell attachment was performed using C3H10T1/2 cells, which were seeded at a density of $1.875 \times 10^4$ cells per $cm^2$ into 24 well plates containing tissue culture-grade polystyrene (TCPS), low cell attachment polystyrene and low cell attachment polystyrene with QHM polymer sample (circular discs approximately 1 cm in diameter) in DMEM, 10% FBS and 1% PS media. After 2 h, wells were rinsed with PBS to remove unattached cells and incubated with 0.5 mL of 0.25% Trypsin-EDTA (Life Technologies, Carlsbad, Calif.) for 15 min. Subsequently, DMEM, 10% FBS and 1% PS media were added to a final volume of 1 mL and cells were counted using a Beckman Coulter Z2 Particle Counter (Beckman Coulter Inc., Pasadena, Calif.). To enable comparison among groups, cell attachment numbers were normalized by the available surface area.

Cell Viability

Cell viability was measured using live/dead staining (Life Technologies, Carlsbad, Calif.) according to the manufacturer's instructions. Cells were seeded into 24 well plates containing uncoated and fibrin-coated QHM polymer samples (circular discs approximately 1 cm in diameter) at a density of $1.0 \times 10^4$ cells per $cm^2$ overnight in DMEM, 10% FBS and 1% PS media (Day 0). Media were changed every 48 h and live/dead staining was performed on Day 5 using 2 μM calcein AM and 4 μM ethidium homodimer-1. Unstained and 70% methanol-fixed cells groups were included as controls. Fluorescence images were acquired on an inverted Zeiss AxioObserver Z1 microscope equipped with an X-Cite® Series 120Q metal halide lamp, appropriate filters and an AxioCam MRm camera.

Cell Proliferation

Cell proliferation was measured using C2C12 cells, which were seeded at a density of $1.0 \times 10^4$ cells per $cm^2$ into 24 well plates containing TCPS and low cell attachment polystyrene with QHM polymer sample (circular discs approximately 1 cm in diameter) in DMEM, 10% FBS and 1% PS media overnight (Day 1). The following day (Day 2), media were changed to DMEM, 10% FBS and 1% PS media. Media were changed every 48 h. 70% ethanol-fixed cells were included as a negative control. Cells were counted every 48 h (Days 1, 3 and 5) using a Beckman Coulter Z2 Particle Counter.

ALP Staining

ALP activity was detected according to the manufacturer's instructions (Sigma Aldrich, St. Louis, Mo.) as previously described with minor modifications[18,19].

For studies on the effect of Young's moduli on osteoblast differentiation (using uniform QHM polymer samples), C2C12 cells were seeded into 24 well plates containing uncoated QHM polymer samples (circular discs approximately 1 cm in diameter) at a density of $7.47 \times 10^4$ cells per $cm^2$ overnight in DMEM, 10% FBS and 1% PS media. The following day (Day 0), the media were changed to DMEM, 10% FBS, 1% PS, 100 ng/mL BMP-2 and 0.3% DMSO (With BMP-2 and DMSO) or DMEM, 10% FBS, 1% PS, 100 ng/mL BMP-2 and 25 µM blebbistatin (Selleck Chemicals, Houston, Tex.; With BMP-2 and blebbistatin). Media were changed every 48 h. ALP staining was performed at 4, 8 and 14 days. ALP inhibitory index was defined as the ratio of ALP activity for blebbistain-treated cells to DMSO-treated cells—a value of 1.0 indicated no inhibition while a value of 0.0 indicated complete inhibition.

For studies on the effect of Young's moduli on osteoblast differentiation (using 0 s:300 s UV mechanically-graded QHM polymer samples), C2C12 cells were seeded into 24 well plates containing uncoated QHM polymer samples (rectangular specimens measuring approximately 0.5 cm×1 cm) at a density of $7.47 \times 10^4$ cells per $cm^2$ overnight in DMEM, 10% FBS and 1% PS media. The following day (Day 0), the media were changed to DMEM, 10% FBS, 1% PS, 100 ng/mL BMP-2. Media were changed every 48 h. ALP staining were performed at 3 days post-seeding.

For studies on the effect of BMP-2-biopatterning on osteoblast differentiation, C2C12 and C3H10T1/2 cells were seeded into 24 well plates containing BMP-2-biopatterned on fibrin-coated QHM polymer samples (circular discs approximately 1 cm in diameter) at a density of $7.47 \times 10^4$ cells per $cm^2$ in DMEM, 10% FBS, 1% PS media with 1 µg/mL aprotinin (Sigma Aldrich, St. Louis, Mo.). Media were changed every 48 h. ALP staining was performed at 6 days post-seeding.

At designated time points, cells were fixed for 1 min in 3.7% formaldehyde and samples were incubated with ALP stain for 1 h. Color images of samples were acquired using an inverted Zeiss AxioObserver Z1 microscope equipped with an AxioCam ICC color camera and a Nikon D70 Digital camera (Nikon Corp., Tokyo, Japan). Where required, the ALP-stained images were quantified by calculating the average pixel intensity in Adobe Photoshop 7.0 as previously described[18,19].

von Kossa Staining von Kossa staining was performed according to the manufacturer's instructions (American MasterTech Scientific Inc., Lodi, Calif.). Cells were seeded into 24 well plates containing fibrin-coated QHM polymer samples (circular discs approximately 1 cm in diameter) at a density of $7.47 \times 10^4$ cells per $cm^2$ overnight in DMEM, 10% FBS, 1% PS and 1 µg/mL aprotinin media. The following day (Day 0), the media were changed to DMEM, 10% FBS, 1% PS and 1 µg/mL aprotinin (Control media) or DMEM, 10% FBS, 1% PS, 10 mM β-glycerophosphate (Sigma Aldrich, St. Louis, Mo.), 50 µg/mL ascorbic acid (Sigma Aldrich, St. Louis, Mo.), 100 ng/mL BMP-2 and 1 µg/mL aprotinin (Osteogenic media). Media were changed every 72 h. After 27 days, cells were fixed for 30 min in 10% neutral buffered formalin (Thermo Fisher Scientific, Waltham, Mass.), washed in PBS and von Kossa staining was performed. Samples were incubated in 5% silver nitrate and exposed to UV light for 10 min (OmniCure Series 2000 UV system equipped with a collimating adapter, at a distance of 60 cm from the light source, irradiance of 4 Watts per $cm^2$). Color images of samples were acquired using a Nikon D70 Digital camera (Nikon Corp., Tokyo, Japan).

Immunofluorescence Staining

Immunofluorescence staining was performed as previously described with minor modifications[18,19].

For in vitro studies not involving QHM polymers, C2C12 cells were seeded into 24 well plates at a density of $7.47 \times 10^4$ cells per $cm^2$ in DMEM, 10% FBS, 1% PS media. The following day (Day 0), the media were changed to DMEM, 10% FBS, 1% PS with 0, 50 or 100 ng/mL FGF-2. Media were changed every 48 h. Cells were fixed in 4% paraformaldehyde (Electron Microscopy Sciences, Hatfield, Pa.) for 15 min and TENOMODULIN or TENASCIN C staining was performed at 3 days post-seeding.

For studies on the effect of Young's moduli on osteoblast or tenocyte differentiation (using uniform or 0 s:300 s UV mechanically-graded QHM polymer samples), C2C12 cells were seeded into 24 well plates containing uncoated QHM polymer samples (circular discs approximately 1 cm in diameter or rectangular specimens measuring approximately 0.5 cm×1 cm) at a density of $7.47 \times 10^4$ cells per $cm^2$ overnight in DMEM, 10% FBS and 1% PS media. The following day (Day 0), the media were changed to DMEM, 10% FBS, 1% PS, 100 ng/mL FGF-2 (for tenocyte differentiation) or DMEM, 10% FBS, 1% PS, 100 ng/mL BMP-2 (for osteoblast differentiation). Media were changed every 48 h. SCX staining was performed at 3 days post-seeding. RUNT-RELATED TRANSCRIPTION FACTOR-2 (RUNX-2) or OSTEOCALCIN (OCN) staining was performed at 4 days post-seeding.

For in vitro growth factor-biopatterning studies, C2C12 cells were seeded into 24 well plates containing FGF-2-biopatterned on fibrin-coated QHM polymer samples (circular discs approximately 1 cm in diameter) at a density of $7.47 \times 10^4$ cells per $cm^2$ in DMEM, 10% FBS, 1% PS media with 1 µg/mL aprotinin (Sigma Aldrich, St. Louis, Mo.). Media were changed every 48 h. Cells were fixed in 4% paraformaldehyde for 15 min and SCX staining was performed at 3 days post-seeding.

For in vivo studies, antigen retrieval was performed on rehydrated tissue sections in IHC-Tek Epitope retrieval buffer (IHC World LLC, Ellicott City, Md.) at 85-95° C. for 10-30 min.

Samples were permeabilized with 0.2% Triton X-100 (Sigma Aldrich, St. Louis, Mo.), washed three times in wash buffer (PBS and 0.1% BSA) and blocked with 10% donkey serum (Jackson Immunoresearch, West Gove, Pa.) for 1 h at room temperature. Cells were washed with wash buffer and incubated with rabbit anti-RUNX2 (4 µg/mL; sc-10758, Santa Cruz Biotechnology Inc, Santa Cruz, Calif.), rabbit anti-OCN (4 µg/mL; sc-30045, Santa Cruz Biotechnology Inc, Santa Cruz, Calif.), rabbit anti-SCX (10 µg/mL; ab58655, Abcam, Cambridge, Mass.), rabbit anti-TENOMODULIN primary antibody (10 µg/mL; ab203676, Abcam, Cambridge, Mass.) or rabbit anti-TENASCIN C (4 µg/mL; sc-20932, Santa Cruz Biotechnology Inc, Santa Cruz, Calif.) overnight at 4° C. Cells were then rinsed three times with wash buffer (5 min each) and incubated with Cy3- or Alexa 647-labeled donkey anti-rabbit secondary antibody (15 µg/mL; Jackson Immunoresearch, West Gove, Pa.) for 1 h at room temperature. Lastly, cells were rinsed five times with wash buffer (5 min each) and fluorescence images were acquired on an inverted Zeiss AxioObserver Z1 microscope equipped with an X-Cite® Series 120Q metal halide lamp, appropriate filters and an AxioCam MRm camera.

Mouse Subcutaneous Implantation

Mouse subcutaneous surgeries were performed in accordance with the guidelines established by Stanford University's Administrative Panel on Laboratory Animal Care. Wild-type C57BL-6J mice (Charles River Laboratories, Wilmington, Mass.) between 8 and 12 weeks of age (20-30 g) were used in this study. All mice were maintained in the Stanford Animal Facility, with a 12:12 h light-dark cycle and free access to standard laboratory food and water. Mice were anesthetized by inhalation with isoflurane (4% for induction, 2% for maintenance, Abbott Laboratories, Chicago) as well as administered 0.05 mg/kg Buprenorphine (Hospira Inc., Lake Forest, Ill.) and 25 mg/kg Cefazolin (Thermo Fisher Scientific, Waltham, Mass.) as an analgesic and anti-infective, respectively. Grafts (Square specimens 6×6×1 mm) were comprised of 0 s UV and 300 s UV QHM polymer regions (each measuring 3×3×1 mm) biopatterned with 1) no growth factor, 2) 3 µg FGF-2 on 0 s UV QHM polymer region and 3 µg BMP-2 on 300 s UV QHM polymer region or 3) 3 µg GDF-7 on 0 s UV QHM polymer region and 3 µg BMP-2 on 300 s UV QHM polymer region. Under sterile conditions, a 2.5 cm skin incision was made and grafts were sutured subcutaneously to the skin using 3-0 Nylon sutures (Oasis, Med-Vet International, Mettawa, Ill.) in a bilateral manner. Subsequently, the skin was re-approximated and closed with 3-0 Nylon sutures. All mice recovered on a heating pad. At 2 weeks post-surgery, samples were harvested. Grafts were assigned to mice in a non-randomized fashion to avoid potential growth factor-crosstalk. Blinded group allocation was not performed.

Harvested samples were fixed in 4% paraformaldehyde overnight and stored in 70% ethanol until further processing. Samples were decalcified for 2 weeks in 10% EDTA (Sigma Aldrich, St. Louis, Mo.). Samples were subsequently subjected to a graded ethanol dehydration series (two washes in 70% ethanol, two washes in 85% ethanol, two washes in 95% ethanol and two washes in 100% ethanol; 30 mins each) followed by xylene infiltration (two washes in 50% xylene in ethanol and two washes in 100% xylene; 30 min each) and then paraffin infiltration at 60° C. (one wash in 50% paraffin in xylene for 1 h, three washes in 100% paraffin for 20 min each and 100% paraffin overnight). Subsequently, samples were embedded in paraffin blocks and sectioned at 6-8 µm intervals using a Leica rotary microtome (RM 2255, Leica Biosystems Inc., Buffalo Grove, Ill.). Prior to staining, sections were de-paraffinized using two washes in xylene (3 min each) and rehydrated using a graded ethanol series (two washes in 100% ethanol, two washes in 95% ethanol, one wash in 85% ethanol, one wash in 70% ethanol and one wash in de-ionized water; 3 min each).

Samples were subsequently processed for immunofluorescence or histological staining. Histological staining for Hematoxylin and Eosin (H&E), tartrate-resistant acid phosphatase (TRAP) as well as Lillie Modification of Mason's Trichrome (Tri) were performed according to manufacturer's instructions (Electron Microscopy Sciences, Hatfield, Pa.). Images of samples were acquired using either an inverted Zeiss AxioObserver Z1 microscope equipped with an AxioCam ICC color camera or an upright Zeiss Axioimager polarized microscope (Pol; Carl Zeiss Microimaging, Thornwood, N.Y.) equipped with a Zeiss Axiocam 506 color camera (Carl Zeiss Microimaging, Thornwood, N.Y.).

Degradation Studies

Degradation studies were performed on QHM polymer samples (circular discs approximately 1 cm in diameter) under aqueous, alkaline, acidic and oxidizing conditions. QHM polymer samples with a mass of approximately 150 mg were weighed using a Mettler Toledo XS105 Dual Range weigh balance (Mettler Toledo International, Columbus, Ohio) and placed in 1.5 mL of the following solutions at 37° C. for 4 h, 1 week, 2 weeks, 4 weeks or 8 weeks: (1) Hank's buffered salt solution (HBSS; Mediatech Inc, Manassas, Va.), (2) 5 N sodium hydroxide, (3) 2 N hydrochloric acid (EMD Chemicals, Billerica, Mass.) and (4) 30% hydrogen peroxide (Thermo Fisher Scientific, Waltham, Mass.). No media change were performed. These conditions potentially approximated normal and chronic tissue microenvironments as well as potential foreign body reaction towards biomaterials. At each time point, wet weights were recorded, supernatants containing degradation products were collected and QHM polymer samples were processed to record dry weights. To obtain dried specimens, QHM polymer samples were washed in deionized water for 1 h followed by a series of graded ethanol washes (20% ethanol, 50% ethanol, 80% ethanol and 100% ethanol; 10 min each) and placed under low vacuum in a desiccating chamber overnight. Degradation was determined by calculating the percentage of remaining mass at each time point. Swelling ratios at the 4 h time point were determined by calculating the mass difference between wet and dry weights and subsequently dividing the result by the dry weight.

Supernatants from the HBSS groups at 8 weeks were used for determining cell proliferation and differentiation in the presence of degradation products. HBSS supernatants from degradation studies were diluted in DMEM, 10% FBS and 1% PS media at a ratio of 1:9 to yield DMEM media containing degradation products. Dilution was necessary since QHM polymer samples were incubated in HBSS for an extended duration without media change (8 weeks) and a relatively low degradation solution to QHM polymer ratio (10:1) was used. A 1:9 dilution of HBSS supernatant to DMEM media was chosen to maintain cell culture media at pH 7.4. C2C12 cells were seeded into 48 well plates at a density of $3.75 \times 10^4$ cells per $cm^2$ overnight. The following day (Day 0), media were changed to DMEM media containing degradation products. Cells were counted every 24 h using a Beckman Coulter Z2 Particle Counter. Cell differentiation was assessed using phase-contrast images acquired on an inverted Zeiss AxioObserver Z1 microscope equipped with an AxioCam MRm camera.

Statistical Analysis.

All experiments were performed with at least 3 replicates per condition. Sample sizes were estimated to detect a group mean difference of 50%±1 to 2 standard deviations with a power $(1-\beta)$ of 0.8 and $\alpha=0.05$ (http://powerandsamplesize.com/Calculators/Compare-k-Means/1-Way-ANOVA-Pairwise). To determine statistical significance for multiple comparisons, one-way analysis of variance followed by Tukey's Honestly Significant Difference post hoc test was performed using SYSTAT 12 software (Systat Software Inc., Richmond, Calif.). For data that did not satisfy both normality and equal variance assumptions, Welch's analysis of variance followed by Games-Howell post hoc test was performed using IBM SPSS Statistics 23 software (SPSS Inc., Chicago, Ill.). A p value≤0.05 was considered statistically significant.

It should be understood that various alternatives to the embodiments of the invention described herein may be employed in practicing the invention. It is intended that the scope of the invention, methods and structures within the scope of the invention includes equivalents.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1 Lu, H. H. & Thomopoulos, S. Functional attachment of soft tissues to bone: Development, healing, and tissue engineering. *Annual review of biomedical engineering* 15, 201-226, (2013).
2 Qu, D., Mosher, C., Boushell, M. & Lu, H. Engineering complex orthopaedic tissues via strategic biomimicry. *Annals of biomedical engineering* 43, 697-717, (2014).
3 Galatz, L. M., Gerstenfeld, L., Heber-Katz, E. & Rodeo, S. A. Tendon regeneration and scar formation: The concept of scarless healing. *Journal of orthopaedic research* 33, 823-831, (2015).
4 Longo, U. G. et al. Histopathology of the supraspinatus tendon in rotator cuff tears. *American journal of sports medicine* 36, 533-538, (2008).
5 Fukubayashi, T. & Ikeda, K. Follow-up study of gore-tex artificial ligament—special emphasis on tunnel osteolysis. *Journal of long-term effects of medical implants* 10, 267-277, (2000).
6 Kim, S. J., Kim, S. H., Lee, S. K., Seo, J. W. & Chun, Y. M. Arthroscopic repair of massive contracted rotator cuff tears: Aggressive release with anterior and posterior interval slides do not improve cuff healing and integrity. *Journal of bone and joint surgery* 95, 1482-1488, (2013).
7 Gartsman, G. M. *Shoulder arthroscopy.* 2nd edn. (W. B. Saunders, 2009).
8 Walton, J. R., Bowman, N. K., Khatib, Y., Linklater, J. & Murrell, G. A. Restore orthobiologic implant: Not recommended for augmentation of rotator cuff repairs. *Journal of bone and joint surgery* 89, 786-791, (2007).
9 Andarawis-Puri, N., Flatow, E. L. & Soslowsky, L. J. Tendon basic science: Development, repair, regeneration, and healing. *Journal of orthopaedic research* 33, 780-784, (2015).
10 Chaudhury, S., Holland, C., Thompson, M. S., Vollrath, F. & Carr, A. J. Tensile and shear mechanical properties of rotator cuff repair patches. *Journal of shoulder and elbow surgery* 21, 1168-1176, (2011).
11 Chin, L. et al. Characterization of and host response to tyramine substituted-hyaluronan enriched fascia extracellular matrix. *Journal of materials science.* 22, 1465-1477, (2011).
12 Liu, W. et al. Generation of electrospun nanofibers with controllable degrees of crimping through a simple, plasticizer-based treatment. *Advanced materials* 27, 2583-2588, (2015).
13 Makris, E. A., Responte, D. J., Paschos, N. K., Hu, J. C. & Athanasiou, K. A. Developing functional musculoskeletal tissues through hypoxia and lysyl oxidase-induced collagen cross-linking. *Proceedings of the national academy of sciences USA* 111, E4832-4841, (2014).
14 McCarron, J. A., Milks, R. A., Chen, X., Iannotti, J. P. & Derwin, K. A. Improved time-zero biomechanical properties using poly-l-lactic acid graft augmentation in a cadaveric rotator cuff repair model. *Journal of shoulder and elbow surgery* 19, 688-696, (2010).
15 Caliari, S. R. & Harley, B. A. C. Structural and biochemical modification of a collagen scaffold to selectively enhance msc tenogenic, chondrogenic, and osteogenic differentiation. *Advanced healthcare materials* 3, 1086-1096, (2014).
16 Li, X. et al. Nanofiber scaffolds with gradations in mineral content for mimicking the tendon-to-bone insertion site. *Nano letters* 9, 2763-2768, (2009).
17 Spalazzi, J. P. et al. in *Annual International Conference Proceedings of the IEEE Engineering in Medicine and Biology Society.* 525-528.
18 Ker, E. D. et al. Engineering spatial control of multiple differentiation fates within a stem cell population. *Biomaterials* 32, 3413-3422, (2011).
19 Ker, E. D. et al. Bioprinting of growth factors onto aligned sub-micron fibrous scaffolds for simultaneous control of cell differentiation and alignment. *Biomaterials* 32, 8097-8107, (2011).
20 Lamplot, J. D. et al. Distinct effects of platelet-rich plasma and bmp13 on rotator cuff tendon injury healing in a rat model. *American journal of sports medicine* 42, 2877-2887, (2014).
21 Lee, J. Y. et al. Bmp-12 treatment of adult mesenchymal stem cells in vitro augments tendon-like tissue formation and defect repair in vivo. *PLoS one* 6, e17531, (2011).
22 Wolfman, N. M. et al. Ectopic induction of tendon and ligament in rats by growth and differentiation factors 5, 6, and 7, members of the tgf-beta gene family. *Journal of clinical investigation* 100, 321-330, (1997).
23 Chen, X. et al. Scleraxis-overexpressed human embryonic stem cell-derived mesenchymal stem cells for tendon tissue engineering with knitted silk-collagen scaffold. *Tissue engineering Part A* 20, 1583-1592, (2013).
24 Gulotta, L. V., Kovacevic, D., Packer, J. D., Deng, X. H. & Rodeo, S. A. Bone marrow-derived mesenchymal stem cells transduced with scleraxis improve rotator cuff healing in a rat model. *American journal of sports medicine* 39, 1282-1289, (2011).
25 Hoffmann, A. et al. Neotendon formation induced by manipulation of the smad8 signalling pathway in mesenchymal stem cells. *Journal of clinical investigation* 116, 940-952, (2006).
25 Otabe, K. et al. Transcription factor mohawk controls tenogenic differentiation of bone marrow mesenchymal stem cells in vitro and in vivo. *Journal of orthopaedic research* 33, 1-8, (2014).
27 Phillips, J. E. & Garcia, A. J. Retroviral-mediated gene therapy for the differentiation of primary cells into a mineralizing osteoblastic phenotype. *Methods in molecular biology* 433, 333-354, (2008).
28 Barber, F. A. Biodegradable shoulder anchors have unique modes of failure. *Arthroscopy* 23, 316-320, (2007).
29 Miller, E. D. et al. Inkjet printing of growth factor concentration gradients and combinatorial arrays immobilized on biologically-relevant substrates. *Combinatorial chemistry and high throughput screening* 12, 604-618, (2009).
30 Phillippi, J. A. et al. Microenvironments engineered by inkjet bioprinting spatially direct adult stem cells toward muscle- and bone-like subpopulations. *Stem cells* 26, 127-134, (2008).
31 Cooper, G. M. et al. Inkjet-based biopatterning of bone morphogenetic protein-2 to spatially control calvarial bone formation. *Tissue engineering. Part A* 16, 1749-1759, (2010).

32 Smith, D. M. et al. Precise control of osteogenesis for craniofacial defect repair: The role of direct osteoprogenitor contact in bmp-2-based bioprinting. *Annals of plastic surgery* 69, 485-488, (2012).

33 Mercado-Pagan, A. E. et al. Synthesis and characterization of novel elastomeric poly(d,l-lactide urethane) maleate composites for bone tissue engineering. *European polymer journal* 49, 3337-3349, (2013).

34 Silverstein, R. M., Webster, F. X. & Kiemle, D. J. *Spectrometric identification of organic compounds*. 7th edn. (John Wiley & Sons, 2005).

35 Kim, S., Kang, Y., Mercado-Pagan, A. E., Maloney, W. J. & Yang, Y. In vitro evaluation of photo-crosslinkable chitosan-lactide hydrogels for bone tissue engineering. *Journal of biomedical materials research Part B* 102, 1393-1406, (2014).

36 Edom-Vovard, F., Schuler, B., Bonnin, M. A., Teillet, M. A. & Duprez, D. Fgf4 positively regulates scleraxis and tenascin expression in chick limb tendons. *Developmental biology* 247, 351-366, (2002).

37 Engler, A. J., Sen, S., Sweeney, H. L. & Discher, D. E. Matrix elasticity directs stem cell lineage specification. *Cell* 126, 677-689, (2006).

38 Mather, I. I. I. R. C. et al. The societal and economic value of rotator cuff repair. *Journal of bone and joint surgery* 95, 1993-2000, (2013).

39 Itoi, E. et al. Tensile properties of the supraspinatus tendon. *Journal of orthopaedic research* 13, 578-584, (1995).

40 Matsuhashi, T. et al. Tensile properties of a morphologically split supraspinatus tendon. *Clinical anatomy* 27, 702-706, (2014).

41 Wall, J. C., Chatterji, S. K. & Jeffery, J. W. Age-related changes in the density and tensile strength of human femoral cortical bone. *Calcified tissue international* 27, 105-108, (1979).

42 Yuehuei, A. & Robert, D. in *Mechanical testing of bone and the bone-implant interface* (CRC Press, 1999).

43 Bruin, P., Meeuwsen, E. A., van Andel, M. V., Worst, J. G. & Pennings, A. J. Autoclavable highly cross-linked polyurethane networks in ophthalmology. *Biomaterials* 14, 1089-1097, (1993).

44 Wang, H. & Brown, H. R. Self-initiated photopolymerization and photografting of acrylic monomers. *Macromolecular rapid communications* 25, 1095-1099, (2004).

45 Hersche, O. & Gerber, C. Passive tension in the supraspinatus musculotendinous unit after long-standing rupture of its tendon: A preliminary report. *Journal of shoulder and elbow surgery* 7, 393-396, (1998).

46 Meyer, D., Hoppeler, H. & Gerber, C. Structure and contractile force of the supraspinatus muscle is correlated with the results of rotator cuff reconstruction. *Journal of bone and joint surgery, British volume* 90-B, 293, (2008).

47 Murphy, E. B. The return of photoelastic stress measurements: Utilizing birefringence to monitor damage and repair in healable materials. *Journal of materials chemistry* 21, 1438-1446, (2011).

48 Campbell, P. G., Miller, E. D., Fisher, G. W., Walker, L. M. & Weiss, L. E. Engineered spatial patterns of fgf-2 immobilized on fibrin direct cell organization. *Biomaterials* 26, 6762-6770, (2005).

49 Miller, E. D., Fisher, G. W., Weiss, L. E., Walker, L. M. & Campbell, P. G. Dose-dependent cell growth in response to concentration modulated patterns of fgf-2 printed on fibrin. *Biomaterials* 27, 2213-2221, (2006).

50 Miller, E. D. et al. Spatially directed guidance of stem cell population migration by immobilized patterns of growth factors. *Biomaterials* 32, 2775-2785, (2011).

51 Cai, K. et al. Inkjet printing of laminin gradient to investigate endothelial cellular alignment. *Colloids and surfaces B* 72, 230-235, (2009).

52 Marieb, E. N. *Human anatomy and physiology*. 5th edn. (Benjamin Cummings, 1999).

53 McNeill, A. R. Elastic energy stores in running vertebrates. *American zoologist* 24, 85-94, (1984).

54 Genin, G. M. et al. Functional grading of mineral and collagen in the attachment of tendon to bone. *Biophysical journal* 97, 976-985, (2009).

55 Moffat, K. L. et al. Characterization of the structure-function relationship at the ligament-to-bone interface. *Proceedings of the national academy of sciences USA* 105, 7947-7952, (2008).

56 Schwartz, A. G., Pasteris, J. D., Genin, G. M., Daulton, T. L. & Thomopoulos, S. Mineral distributions at the developing tendon enthesis. *PLoS one* 7, e48630, (2012).

57 Benjamin, M. & Ralphs, J. R. Fibrocartilage in tendons and ligaments—an adaptation to compressive load. *Journal of anatomy* 193 (Pt 4), 481-494, (1998).

58 Benjamin, M. et al. Where tendons and ligaments meet bone: Attachment sites ('entheses') in relation to exercise and/or mechanical load. *Journal of anatomy* 208, 471-490, (2006).

59 Liu, Y., Birman, V., Chen, C., Thomopoulos, S. & Genin, G. M. Mechanisms of bimaterial attachment at the interface of tendon to bone. *Journal of engineering materials and technology* 133, 011006, (2011).

60 Tan, T. et al. Mechanical properties of functionally graded hierarchical bamboo structures. *Acta biomaterialia* 7, 3796-3803, (2011).

61 Qin, Z. & Buehler, M. J. Impact tolerance in mussel thread networks by heterogeneous material distribution. *Nature communications* 4, 2187, (2013).

62 Mehrali, M. et al. Dental implants from functionally graded materials. *Journal of biomedical materials research Part A* 101, 3046-3057, (2013).

63 Al-Jassir, F., Fouad, H. & Alothman, O. In vitro assessment of function graded (fg) artificial hip joint stem in terms of bone/cement stresses: 3d finite element (fe) study. *Biomedical engineering online* 12, 5, (2013).

64 Van der Biest, O., Anne, G., Vanmeensel, K. & Vleugels, J. in *Advanced biomaterials* 323-356 (John Wiley & Sons, Inc., 2010).

65 Bartlett, N. W. et al. Soft robotics. A 3d-printed, functionally graded soft robot powered by combustion. *Science* 349, 161-165, (2015).

66 Longo, U. G., Berton, A., Khan, W. S., Maffulli, N. & Denaro, V. Histopathology of rotator cuff tears. *Sports medicine and arthroscopy* 19, 227-236, (2011).

67 Moffat, K. L., Wang, I. N., Rodeo, S. A. & Lu, H. H. Orthopedic interface tissue engineering for the biological fixation of soft tissue grafts. *Clinical sports medicine* 28, 157-176, (2009).

68 Yang, P. J. & Temenoff, J. S. Engineering orthopedic tissue interfaces. *Tissue engineering Part B* 15, 127-141, (2009).

69 Lu, H. H., Subramony, S. D., Boushell, M. K. & Zhang, X. Tissue engineering strategies for the regeneration of orthopedic interfaces. *Annals of biomedical engineering* 38, 2142-2154, (2010).

70 Lichtwark, G. A. & Wilson, A. M. Is achilles tendon compliance optimised for maximum muscle efficiency during locomotion? *Journal of biomechanics* 40, 1768-1775, (2007).

71 Lichtwark, G. A. & Wilson, A. M. Optimal muscle fascicle length and tendon stiffness for maximising gastrocnemius efficiency during human walking and running. *Journal of theoretical biology* 252, 662-673, (2008).

72 Sano, H. et al. Degeneration at the insertion weakens the tensile strength of the supraspinatus tendon: A comparative mechanical and histologic study of the bone-tendon complex. *Journal of orthopaedic research* 15, 719-726, (1997).

73 Belcher, H. J. C. R. & Zic, R. Adverse effect of porcine collagen interposition after trapeziectomy: A compartive study. *Journal of hand surgery: British and European volume* 26, 159-164, (2001).

74 Derwin, K. A., Baker, A. R., Spragg, R. K., Leigh, D. R. & Iannotti, J. P. Commercial extracellular matrix scaffolds for rotator cuff tendon repair. Biomechanical, biochemical, and cellular properties. *Journal of bone and joint surgery* 88, 2665-2672, (2006).

75 Malcarney, H. L., Bonar, F. & Murrell, G. A. C. Early inflammatory reaction after rotator cuff repair with a porcine small intestine submucosal implant: A report of 4 cases. *American journal of sports medicine* 33, 907-911, (2005).

76 Sclamberg, S. G., Tibone, J. E., Itamura, J. M. & Kasraeian, S. Six-month magnetic resonance imaging follow-up of large and massive rotator cuff repairs reinforced with porcine small intestinal submucosa. *Journal of shoulder and elbow surgery* 13, 538-541, (2004).

77 Soler, J. A., Gidwani, S. & Curtis, M. J. Early complications from the use of porcine dermal collagen implants (permacol) as bridging constructs in the repair of massive rotator cuff tears. A report of 4 cases. *Acta orthopaedica Belgica* 73, 432-436, (2007).

78 Alfredo Uquillas, J., Kishore, V. & Akkus, O. Genipin crosslinking elevates the strength of electrochemically aligned collagen to the level of tendons. *Journal of the mechanical behavior of biomedical materials* 15C, 176-189, (2012).

79 Younesi, M., Islam, A., Kishore, V., Anderson, J. M. & Akkus, O. Tenogenic induction of human mscs by anisotropically aligned collagen biotextiles. *Advanced functional materials* 24, 5762-5770, (2014).

80 Inui, A. et al. Application of layered poly (l-lactic acid) cell free scaffold in a rabbit rotator cuff defect model. *Sports medicine, arthroscopy, rehabilitation, therapy and technology* 3, 29, (2011).

81 Inui, A. et al. Regeneration of rotator cuff tear using electrospun poly(d,l-lactide-co-glycolide) scaffolds in a rabbit model. *Arthroscopy* 28, 1790-1799, (2012).

82 Spalazzi, J. P. et al. In vivo evaluation of a multiphased scaffold designed for orthopaedic interface tissue engineering and soft tissue-to-bone integration. *Journal of biomedical materials research Part A* 86, 1-12, (2008).

83 Spalazzi, J. P., Doty, S. B., Moffat, K. L., Levine, W. N. & Lu, H. H. Development of controlled matrix heterogeneity on a triphasic scaffold for orthopedic interface tissue engineering. *Tissue engineering* 12, 3497-3508, (2006).

84 Xie, J. et al. "Aligned-to-random" nanofiber scaffolds for mimicking the structure of the tendon-to-bone insertion site. *Nanoscale* 2, 923-926, (2010).

85 Xie, J., Ma, B., Michael, P. L. & Shuler, F. D. Fabrication of nanofiber scaffolds with gradations in fiber organization and their potential applications. *Macromolecular bioscience* 12, 1336-1341, (2012).

86 Smith, M. J. et al. Comparison of a novel bone-tendon allograft with a human dermis-derived patch for repair of chronic large rotator cuff tears using a canine model. *Arthroscopy* 28, 169-177, (2012).

87 Ramalingam, M. et al. Nanofiber scaffold gradients for interfacial tissue engineering. *Journal of biomaterials applications* 27, 695-705, (2013).

88 Beason, D. P. et al. Fiber-aligned polymer scaffolds for rotator cuff repair in a rat model. *Journal of shoulder and elbow surgery* 21, 245-250, (2012).

89 Spencer, E. E., Jr. et al. Interobserver agreement in the classification of rotator cuff tears using magnetic resonance imaging. *American journal of sports medicine* 36, 99-103, (2008).

90 Szycher, M. *Szycher's handbook of polyurethanes* 2nd edn. (CRC Press, 2012).

91 St. John, K. R. The use of polyurethane materials in the surgery of the spine: A review. *Spine journal* 14, 3038-3047, (2014).

92 Ker, R. F. Dynamic tensile properties of the plantaris tendon of sheep (ovis aries). *Journal of experimental biology* 93, 283-302, (1981).

93 Nagasawa, K., Noguchi, M., Ikoma, K. & Kubo, T. Static and dynamic biomechanical properties of the regenerating rabbit achilles tendon. *Clinical biomechanics (Bristol, Avon)* 23, 832-838, (2008).

94 Bogy, D. B. The plane solution for joined dissimilar elastic semistrips under tension. *Journal of applied mechanics* 42, 93-98, (1975).

95 Xu, L. R., Kuai, H. & Sengupta, S. Dissimilar material joints with and without free-edge stress singularities: Part i. A biologically inspired design. *Experimental mechanics* 44, 608-615, (2004).

96 Xu, L. R. & Sengupta, S. Dissimilar material joints with and without free-edge stress singularities: Part ii. An integrated numerical analysis. *Experimental mechanics* 44, 616-621, (2004).

97 Guo, Y. et al. Mechanical strain promotes osteoblast ecm formation and improves its osteoinductive potential. *Biomedical engineering online* 11, 80, (2012).

98 Androjna, C., Spragg, R. K. & Derwin, K. A. Mechanical conditioning of cell-seeded small intestine submucosa: A potential tissue-engineering strategy for tendon repair. *Tissue engineering* 13, 233-243, (2007).

99 Popov, C. et al. Mechanical stimulation of human tendon stem/progenitor cells results in upregulation of matrix proteins, integrins and mmps, and activation of p38 and erk1/2 kinases. *Biomed central molecular biology* 16, 6, (2015).

100 Morais, D. S., Torres, J., Guedes, R. M. & Lopes, M. A. Current approaches and future trends to promote tendon repair. *Annals of biomedical engineering* 43, 2025-2035, (2015).

101 Caliari, S. R. & Harley, B. A. C. The effect of anisotropic collagen-gag scaffolds and growth factor supplementation on tendon cell recruitment, alignment, and metabolic activity. *Biomaterials* 32, 5330-5340, (2011).

102 Kovacevic, D. et al. Calcium-phosphate matrix with or without tgf-beta3 improves tendon-bone healing after rotator cuff repair. *American journal of sports medicine* 39, 811-819, (2011).

103 Zhao, S. et al. Effect of the interposition of calcium phosphate materials on tendon-bone healing during repair of chronic rotator cuff tear. *American journal of sports medicine* 42, 1920-1929, (2014).

104 Mihara, S., Fujita, T., Ono, T., Inoue, H. & Kisimoto, T. Rotator cuff repair using an original iliotibial ligament with a bone block patch: Preliminary results with a 24-month follow-up period. *Journal of shoulder and elbow surgery*, In Press, (2016).

105 Kim, H. J. et al. The effect of platelet rich plasma from bone marrow aspirate with added bone morphogenetic protein-2 on the achilles tendon-bone junction in rabbits. *Clinics in orthopedic surgery* 3, 325-331, (2011).

106 Lee, K. W., Lee, J. S., Jang, J. W., Shim, Y. B. & Lee, K. I. Tendon-bone interface healing using an injectable rhbmp-2-containing collagen gel in a rabbit extra-articular bone tunnel model. *Journal of tissue engineering and regenerative medicine*, In Press, (2015).

107 Kabuto, Y. et al. Stimulation of rotator cuff repair by sustained release of bone morphogenetic protein 7 using a gelatin hydrogel sheet. *Tissue engineering Part A* 21, 2025-2033, (2015).

108 Peterson, D. R. et al. Evaluation of a collagen-coated, resorbable fiber scaffold loaded with a peptide basic fibroblast growth factor mimetic in a sheep model of rotator cuff repair. *Journal of shoulder and elbow surgery* 24, 1764-1773, (2015).

109 Tang, J. B., Chen, C. H., Zhou, Y. L., McKeever, C. & Liu, P. Y. Regulatory effects of introduction of an exogenous fgf2 gene on other growth factor genes in a healing tendon. *Wound repair and regeneration* 22, 111-118, (2014).

110 Tokunaga, T. et al. Fgf-2 stimulates the growth of tenogenic progenitor cells to facilitate the generation of tenomodulin-positive tenocytes in a rat rotator cuff healing model. *American journal of sports medicine* 43, 2411-2422, (2015).

111 Zhang, C. et al. Bfgf- and capp-loaded fibrin clots enhance the bioactivity of the tendon-bone interface to augment healing. *American journal of sports medicine*, In Press, (2016).

112 Seeherman, H. J. et al. Rhbmp-12 accelerates healing of rotator cuff repairs in a sheep model. *Journal of bone and joint surgery* 90, 2206-2219, (2008).

113 Shen, H., Gelberman, R. H., Silva, M. J., Sakiyama-Elbert, S. E. & Thomopoulos, S. Bmp12 induces tenogenic differentiation of adipose-derived stromal cells. *PLoS one* 8, e77613, (2013).

114 Tokunaga, T. et al. Local application of gelatin hydrogel sheets impregnated with platelet-derived growth factor bb promotes tendon-to-bone healing after rotator cuff repair in rats. *Arthroscopy* 31, 1482-1491, (2015).

115 Wang, W. et al. Induction of transient tenogenic phenotype of high density cultured human dermal fibroblasts. *Connective tissue research* 56, 288-299, (2015).

116 Lipner, J. et al. In vivo evaluation of adipose derived stromal cells delivered with a nanofiber scaffold for tendon-to-bone repair. *Tissue engineering Part A* 21, 2766-2774, (2015).

117 Zhang, C. et al. Well-aligned chitosan-based ultrafine fibers committed teno-lineage differentiation of human induced pluripotent stem cells for achilles tendon regeneration. *Biomaterials* 53, 716-730, (2015).

118 Phillips, J. E., Burns, K. L., Le Doux, J. M., Guldberg, R. E. & Garcia, A. J. Engineering graded tissue interfaces. *Proceedings of the national academy of sciences USA* 105, 12170-12175, (2008).

119 Pelled, G. et al. Smad8/bmp2-engineered mesenchymal stem cells induce accelerated recovery of the biomechanical properties of the achilles tendon. *Journal of orthopaedic research* 30, 1932-1939, (2012).

120 Theiss, F. et al. Use of biomimetic microtissue spheroids and specific growth factor supplementation to improve tenocyte differentiation and adaptation to a collagen-based scaffold in vitro. *Biomaterials* 69, 99-109, (2015).

121 Chen, B. et al. Tissue engineering of tendons: A comparison of muscle-derived cells, tenocytes, and dermal fibroblasts as cell sources. *Plastic and reconstructive surgery* 137, 536e-544e, (2016).

122 Blau, H. M. et al. Plasticity of the differentiated state. *Science* 230, 758-766, (1985).

123 Huard, J. et al. Human myoblast transplantation: Preliminary results of 4 cases. *Muscle and nerve* 15, 550-560, (1992).

124 Wright, W. E., Sassoon, D. A. & Lin, V. K. Myogenin, a factor regulating myogenesis, has a domain homologous to myod. *Cell* 56, 607-617, (1989).

125 Zhao, C. et al. Spontaneous and specific myogenic differentiation of human mesenchymal stem cells on polyethylene glycol-linked multi-walled carbon nanotube films for skeletal muscle engineering. *Nanoscale* 7, 18239-18249, (2015).

126 Manolagas, S. C., Burton, D. W. & Deftos, L. J. 1,25-dihydroxyvitamin d3 stimulates the alkaline phosphatase activity of osteoblast-like cells. *Journal of biological chemistry* 256, 7115-7117, (1981).

127 Manolagas, S. C., Spiess, Y. H., Burton, D. W. & Deftos, L. J. Mechanism of action of 1,25-dihydroxyvitamin d3-induced stimulation of alkaline phosphatase in cultured osteoblast-like cells. *Molecular and cellular endocrinology* 33, 27-36, (1983).

128 Asonova, S. N. & Migalkin, N. S. [use of masson's trichrome method for staining decalcified bone tissue]. *Arkhiv patologii* 58, 66-67, (1996).

129 Bromage, T. G. et al. Circularly polarized light standards for investigations of collagen fiber orientation in bone. *Anatomical record Part B* 274B, 157-168, (2003).

130 Puchtler, H. & Meloan, S. N. Demonstration of phosphates in calcium deposits: A modification of von kossa's reaction. *Histochemistry* 56, 177-185, (1978).

131 Blumer, M. J. et al. Role of tartrate-resistant acid phosphatase (trap) in long bone development. *Mechanisms of development* 129, 162-176, (2012).

132 Brent, A. E. & Tabin, C. J. Fgf acts directly on the somitic tendon progenitors through the ets transcription factors pea3 and erm to regulate scleraxis expression. *Development* 131, 3885-3896, (2004).

133 Cserjesi, P. et al. Scleraxis: A basic helix-loop-helix protein that prefigures skeletal formation during mouse embryogenesis. *Development* 121, 1099-1110, (1995).

134 Shukunami, C., Takimoto, A., Oro, M. & Hiraki, Y. Scleraxis positively regulates the expression of tenomodulin, a differentiation marker of tenocytes. *Developmental biology* 298, 234-247, (2006).

135 Riley, G. P., Harrall, R. L., Cawston, T. E., Hazleman, B. L. & Mackie, E. J. Tenascin-c and human tendon degeneration. *American journal of pathology* 149, 933-943, (1996).

136 Tang, Q. M. et al. Fetal and adult fibroblasts display intrinsic differences in tendon tissue engineering and regeneration. *Scientific reports* 4, 5515, (2014).

137 Wen, J. H. et al. Interplay of matrix stiffness and protein tethering in stem cell differentiation. *Nature materials* 13, 979-987, (2014).

138 Yang, C., Tibbitt, M. W., Basta, L. & Anseth, K. S. Mechanical memory and dosing influence stem cell fate. *Nature materials* 13, 645-652, (2014).

139 Taipale, J. & Keski-Oja, J. Growth factors in the extracellular matrix. *Federation of American societies for experimental biology journal* 11, 51-59, (1997).

140 Wildemann, B., Kadow-Romacker, A., Pruss, A., Haas, N. P. & Schmidmaier, G. Quantification of growth factors in allogenic bone grafts extracted with three different methods. *Cell and tissue banking* 8, 107-114, (2007).

141 Deakin, M. et al. Suture strength and angle of load application in a suture anchor eyelet. *Arthroscopy* 21, 1447-1451, (2005).

142 Cobaleda Aristizabal, A. F., Sanders, E. J. & Barber, F. A. Adverse events associated with biodegradable lactide-containing suture anchors. *Arthroscopy* 30, 555-560, (2014).

143 Randelli, P., Bak, K. & Milano, G. State of the art in rotator cuff repair. *Knee surgery, sports traumatology, arthroscopy* 23, 341-343, (2015).

144 Joo Han, O., Byung Wook, S. & Tae-Yon, R. Two cases of biodegradable suture anchor displacement diagnosed with ultrasonography following arthroscopic rotator cuff repair. *Clinics in shoulder and elbow*, In Press, (2015).

145 Bostman, O. M. & Pihlajamaki, H. K. Adverse tissue reactions to bioabsorbable fixation devices. *Clinical orthopaedics and related research* 371, 216-227, (2000).

146 Glueck, D., Wilson, T. C. & Johnson, D. L. Extensive osteolysis after rotator cuff repair with a bioabsorbable suture anchor: A case report. *American journal of sports medicine* 33, 742-744, (2005).

147 Schneider, L. A., Korber, A., Grabbe, S. & Dissemond, J. Influence of ph on wound-healing: A new perspective for wound-therapy? *Archives of dermatological research* 298, 413-420, (2007).

148 Anderson, J. M., Rodriguez, A. & Chang, D. T. Foreign body reaction to biomaterials. *Seminars in immunology* 20, 86-100, (2008).

The invention claimed is:

1. A polyurethane comprising: a reaction product of (i) a polyol, wherein the polyol further comprises a tertiary amine, (ii) a polyisocyanate, and (iii) an acrylate selected from the group consisting of methyl acrylate, ethyl acrylate, methyl methacrylate, acrylic anhydride, methacrylic anhydride, acrylamide, methacrylamide, acrylic acid, and methacrylic acid.

2. The polyurethane of claim 1, wherein the polyol is selected from the group consisting of N,N,N',N'-tetrakis(2-hydroxypropyl)ethylenediamine, triethanol amine, triisopropanolamine, 1-[N,N-bis(2-hydroxyethyl)amino]-2-propanol, and 4-[N,N-bis(2-hydroxyethyl)amino]benzaldehyde.

3. The polyurethane of claim 1, wherein the polyisocyanate is selected from the group consisting of isophorone diisocyanate, methylene dicyclohexyl diisocyanate, 2,4-diisocyanatotoluene, 4,4'-methylene bis-(cyclohexylisocyanate), hexamethylene diisocyanate, biuret of hexamethylene diisocyanate, hexamethylene diisocyanate isocyanuratetrimer, hexamethylene diisocyanate uretdione, poly(hexamethylene diisocyanate), isophorone diisocyanate trimer, 1,3cyclohexane bis(methylisocyanate), and 2,2,4,-trimethyl hexamethylene diisocyanate.

4. A polyurethane comprising: a reaction product of (i) a polyol, wherein the polyol further comprises a tertiary amine, (ii) a polyisocyanate, and (iii) an acrylate, wherein the polyol comprises N,N,N',N'-tetrakis(2-hydroxypropyl) ethylenediamine, the polyisocyanate comprises hexamethylene diisocyanate, and the acrylate comprises methacrylic anhydride.

5. A polyurethane biomaterial comprising: a reaction product of a polyol, a polyisocyanate, and an acrylate, wherein the polyurethane has a gradient of mechanical properties through photocrosslinking such that a first end of the biomaterial is crosslinked at a higher degree than a second end.

6. The polyurethane of claim 5, wherein the polyol is selected from the group consisting of glycerol, erythritol, threitol, arabitol, Xylitol, ribitol, pentaerythritol, dipentaerythritol, mannitol, sorbitol, galactitol, iditol, volemitol, fucitol, inositol, maltitol, lactitol, isomalt, maltotritol, maltotetraitol, polyglycitol, polymeric triols, ethylene oxide triols, polycaprolactone triols, polycarbonate triols, polymeric tetrols, polycaprolactone tetrols, 1,1,1-tris(hydroxymethyl) ethane and 1,1,1-tris(hydroxymethyl)propane.

7. The polyurethane of claim 5, wherein the polyol and the acrylate are combined as a single agent.

8. The polyurethane of claim 7, wherein the single compound is selected from pentaerythritol triacrylate or glycerol 1,3 diglycerolate diacrylate.

9. The polyurethane biomaterial of claim 5, wherein the first end and the second end have a tensile strength in a range of from about 4.0 to about 170.0 MPa, a tensile modulus in a range of from about 0.6 to about 29.0 GPa, a compressive strength in a range of from about 58 to about 213 MPa, and a compressive modulus in a range of from about 1.5 to about 34.3 GPa.

10. The polyurethane biomaterial of claim 9, wherein the first end and the second end have a tensile strength in a range of from about 12 to about 74 MPa, a tensile modulus in a range of from about 0.6 to about 2.7 GPa, a compressive strength in a range of from about 58 to about 121 MPa, and a compressive modulus in a range of from about 1.5 to about 3.1 GPa.

11. The polyurethane biomaterial of claim 5, wherein the first end has a tensile strength of from about 66 to about 170.0 MPa, a tensile modulus of from about 11 to about 29.0 GPa, a compressive strength of from about 167 to about 213 MPa, and a compressive modulus of from about 14.7 to about 34.3 GPa.

12. The polyurethane biomaterial of claim 5, wherein the second end having a tensile strength of from about 4 to about 22 MPa and a tensile modulus of from about 0.2 to about 0.6 GPa.

13. A method of making a polyurethane biomaterial, comprising:
mixing a polyol, a polyisocyanate, and an acrylate to form a polyurethane pre-mixture;
degassing the polyurethane pre-mixture under vacuum;
transferring the polyurethane pre-mixture to a mold;
reacting the polyurethane pre-mixture under vacuum or in an inert atmosphere to form an intermediate material;
UV-curing the intermediate material by exposure to UV light;
placing the intermediate material under pressure in an inert atmosphere; and
heat-curing the intermediate material to form the polyurethane.

14. The method of claim 13, further comprising applying a mask to control the exposure to UV light when forming the intermediate material, wherein the mask comprises a translucent/semi-transparent material.

15. The method of claim 14, further comprising moving the mask gradually along a length of the polyurethane pre-mixture during the curing.

16. The method of claim 14, wherein the mask provides levels of shade during the curing to allow varying a degree of exposure to UV light to the polyurethane pre-mixture to create a gradient of mechanical properties similar to bone at one end of the biomaterial and similar to tendon at another end of the biomaterial.

\* \* \* \* \*